US006635811B1

(12) United States Patent
Flintham et al.

(10) Patent No.: US 6,635,811 B1
(45) Date of Patent: Oct. 21, 2003

(54) PRE-HARVEST SPROUTING

(75) Inventors: John Ellis Flintham, Norfolk (GB);
Michael Denis Gale, Norfolk (GB);
Michael John Holdsworth, Bristol (GB); John R. Lenton, Bristol (GB)

(73) Assignee: Plant Bioscience Limited, Norwick (GB)

( * ) Notice: Subject to any disclaimer, the term of this patent is extended or adjusted under 35 U.S.C. 154(b) by 0 days.

(21) Appl. No.: 09/508,824

(22) PCT Filed: Sep. 18, 1998

(86) PCT No.: PCT/GB98/02835

§ 371 (c)(1),
(2), (4) Date: May 17, 2000

(87) PCT Pub. No.: WO99/15667

PCT Pub. Date: Apr. 1, 1999

(30) Foreign Application Priority Data

Sep. 19, 1997 (GB) .............................................. 9720060

(51) Int. Cl.$^7$ ............................ A01H 1/00; A01H 5/00; E12P 21/06; C12N 15/00; C12N 15/82; C07H 15/29

(52) U.S. Cl. .................... 800/320.3; 800/278; 800/290; 800/298; 800/320; 435/69.1; 435/320.1; 435/468; 536/23.6

(58) Field of Search ................................. 800/290, 298, 800/278, 320, 320.3; 435/320.1, 419, 468, 69.1; 536/23.6

(56) References Cited

PUBLICATIONS

Jones et.al.; Identification and analysis of proteins that interact with the Avena Fatua homologue of the maize transcription factor VIVIPAROUS 1, 2000, Plant Journal 21(2): 133–142.*
Stone et.al.; LEAFY COTYLEDON2 encodes a B3 domain transcription factor that induces embryo development, 2001, PNAS, vol. 98, No. 20: 11806–11811.*
Burgess et.al.; Possible Dissociation of the Heparin–binding and Mitogenic Activities of Heparin–binding . . . of a Single Lysine Residue, 1990, The Journal of Cell Biology, vol. 111:2129–2138.*
Hill et.al.; Functional analysis of Conserved Histidines in ADP–Glucose Pyrophosphorylase from Escherichia, 1998, Biochemical and Biophysical Research Comm. 244: 573–577.*
Bowie et.al.; Deciphering the Message in Protein Sequences: Tolerance to amino Acid Substitutions, 1990, Science, vol. 247: 1306–1310.*
Lazar et.al.; Transforming Growth Factor: Mutation of Aspartic 47 and Leucine 48 Results in Different Biological Activities, 1988, Molecular and Cellular Biology, vol. 8, No. 3: 1247–1252.*

Broun et.al.; Catalytic Plasticity of Fatty Acid Modification Enzymes Underlying Chemical Diversity of Plant Lipids, 1998, Science vol. 282: 1315–1317.*
Wilson, W.A. et al., "Poaceae Sequence Analysis: Cloning of a Vivipary–1 Homolog from Genomic Barley DNA Via PCR"; Poster Abstracts, P184, PAGA V (1997).
McCarty, D.R. et al., "The Viviparous–1 Developmental Gene of Maize Encodes a Novel Transcriptional Activator"; Cell, 66:895–905 (1991).
McCarty, D.A. et al., "Molecular Analysis of viviparous–1: An Abscisic Acid–Insensitive Mutant of Maize"; The Plant Cell, 1:523–532 (1989).
Derera, N.F., "Breeding for Preharvest Sprouting Tolerance" in Preharvest Field Sprouting in Cereals at Chapter 6, pp. 112–128 (Derera, N.F., ed., CRC Press, Boca Raton, FL 1989).
Mares, D.J. et al., "Preharvest Sprouting Damage and Sprouting Tolerance: Assay Methods and Instrumentation" in Preharvest Field Sprouting in Cereals at Chapter 7, pp. 129–170 (Derera, N.F., ed., CRC Press, Boca Raton, FL 1989).
Giraudat, J. et al., "Isolation of the Arabidopsis AB13 Gene by Positional Cloning"; The Plant Cell, 4: 1251–1261 (1992).
Cadle, M.M. et al., "Mapping of abscisic acid responsive genes and vp1 to chromosomes in wheat and Lophopyrum elongatum"; Genome, 37: 129–132 (1994).
Holdsworth, M., "Dormancy–Related Expression of the Wild Oat (Avena Fatua) Homolog of the Maize Gene Viviparous 1 (VP 1)." Japan (1995) [Abstract].
Jones, H.D. et al., "Embryo dormancy in wild oat (Avena fatua) is correlated with expression of the VP1 homologue."; Journal of Experimental Botany, P5.10 (1997) [Abstract].
McKibbin, R. et al., "Analysis of the molecular control of pre–harvest sprouting in wheat."; Journal of Experimental Botany, P5.32 (1997) [Abstract].

* cited by examiner

Primary Examiner—Elezabeth F. McElwain
Assistant Examiner—Stuart F. Baum
(74) Attorney, Agent, or Firm—Dann, Dorfman, Herrell and Skillman

(57) ABSTRACT

The invention relates to materials and methods which may be used in the detection and manipulation of Pre-Harvest Sprouting (PHS) and other dormancy-related phenotypes in plants. Specifically disclosed are oat and wheat VP1 homologues (afVP1 and taVP1 respectively) plus also variants, particularly alleles of these. The sequence and mapping data provided can be used in plant breeding and/or in molecular-biology based methods to improve e.g. wheat varieties. Also disclosed are primers which are specific for orthologues, alleles or wheat-genomes plus methods of using these. Vectors, cells and transgenic plants are also provided, as are related products and methods of use.

9 Claims, 23 Drawing Sheets

Figure 1:
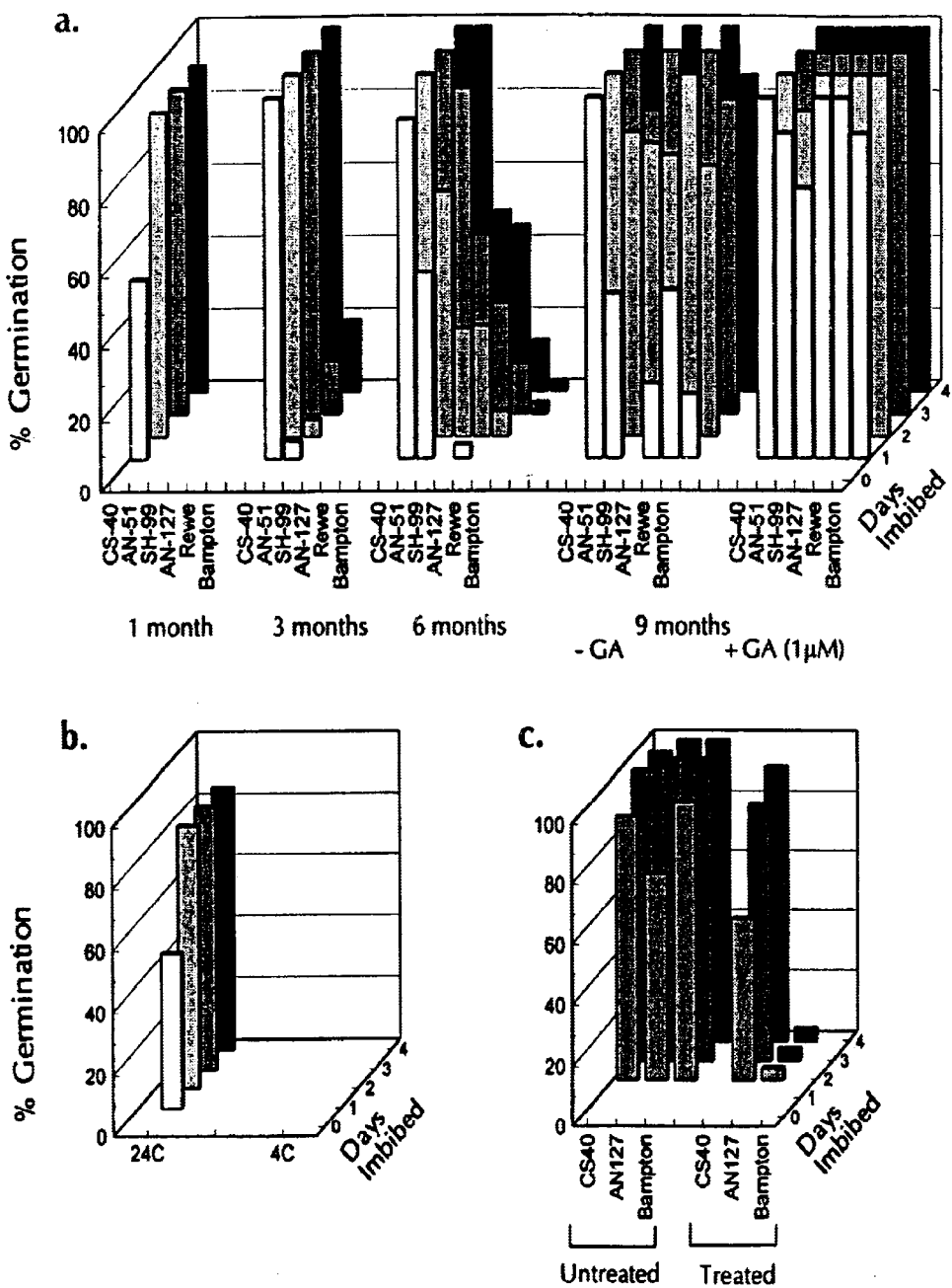

Figure 2
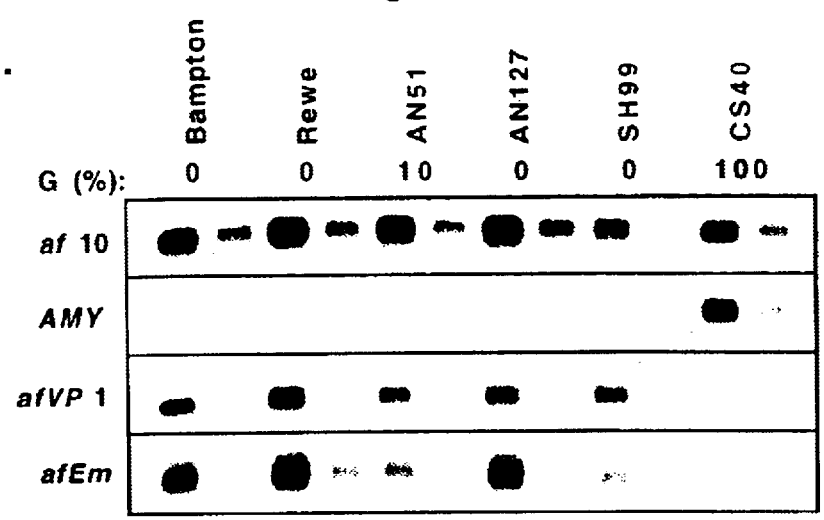
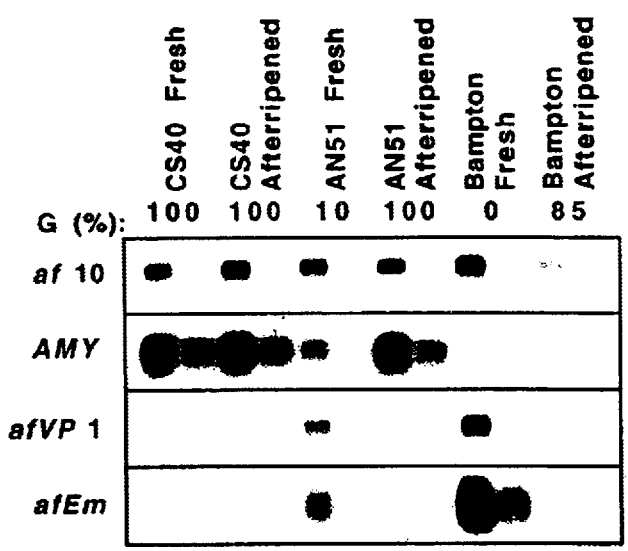
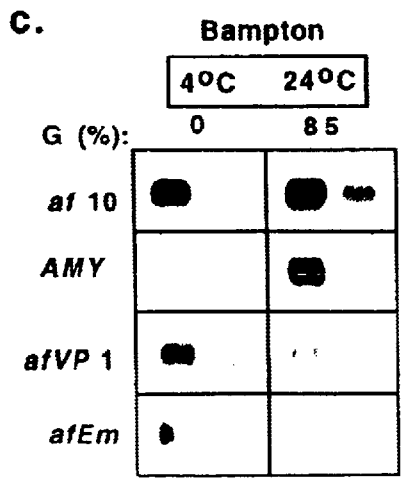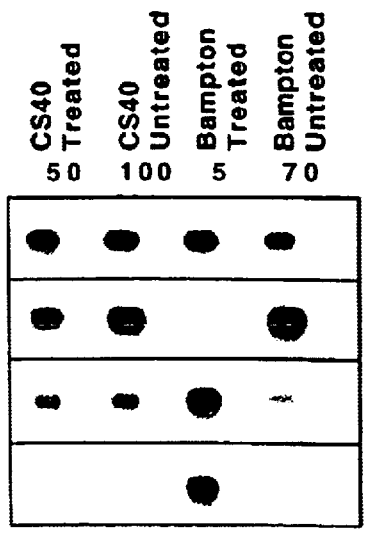

Figure 4(a)

```
   1 GCACACCCCT TCTTCCCTCC TTCCCTCCCT CCCTCCTCCT GCCTTCCCTT TGCATGGACG
  61 CCTCCGCCGG CTCCTCGCCG CCGCCGCACT CGCAGGAGAA CCCGCCCAAG CACGGTGGAG
 121 GCCGCGGGAA GCGTGCGGGG GAGATCCGGA AGGGAGAGGC GGCCACGGCG GATGACTTTA
 181 TGTTCGCGGA AGATACCTTC CCGTCCCTCC CGGATTTCCC TTGCCTCTCC TCCCGTTCAA
 241 GCTCCACCTT CTCCTCCTCA TCCTCCTCCA ACTCATCCAG CACCCACGCC GCCGCGGGAC
 301 GCGGCGTGGC CGTTGTCGCG GACGCCCGAA GGCGCCTCGG GGAGCCCTCC GATCCTGCTG
 361 CCGCGGGGGA CGATGACGTG CTCGACGACA TCGACGAGCT GCTCAACTCT GCCACGCTCT
 421 CCGACTCCAT GCCCTGGGAG GACGAGCCGC TCTTCCCCGA CGACGTTGGC ATGATGATAG
 481 AGGACGCCAT CTCCCACCAG CCGCCCGCCA CGGGCCACCG CGGAGCCAGG AACGCTGCAT
 541 CATCGGAGGC GGCTGCTGGT GGTGGTGGAC AGGATTCCTC GTCGGCGGAC GACCTGCCGC
 601 GGTTCTTCAT GGAGTGGCTG ACGAACAACC GCGACTGCAT CTCCGCCGAG GACCTCCGCA
 661 GCATCCGCCT CCGCCGCTCG ACCATCGAGG CCGCGGCGGC GCGGCTCGGT GGAGGGCGGC
 721 AGGGCACCAT GCAGCTGCTC AAGCTCATCC TCACATGGGT GCAGAACCAC CATCTGCAGA
 781 AGAAGCGCGC CCGCGTCGAC GACGAGCTCC CAGCCCCGG CGCAAACCCG GGTTACGAGT
 841 TCCCCGCGGA GACAGTTGCC CCCGCCACAT CCTGGCTCAT GCCCTACCAA CAAGCTTATG
 901 GAAGAGAGGC GATCTACCCG AACGCCGCCG CCACCGGGCA GTACCCATTC CAGCAGGGCG
 961 GCAGCACGAG CAGCGTGGTG GTGAGCAGCC AGCCGTTCTC CCCGCCGGCG CCGGTGGCCG
1021 ACATGCAGGC GGCGAACATG CCCTGGCCGC AGCAGTACGC GGCGTTCCCC GGCGCTGCGC
1081 CATACCCGAT GCCGCCGCCG CAGCCGTTGG CGGCGGCCGG ATTCGGCGTG TGCCCGCAGC
1141 CCTTGGCCGG GGTGAAGCCG TCGGCGAGCA AGGAGGCCCG GAAGAAGCGT ATGGCGAGGC
1201 AGCGCCGCCT CTCCTGCCTG CAGCATCAGC GGAGCCAGCA GCTGAATCTG GGCCAGATCC
1261 AGAACGCCAT GATCCATCCG CAGCAGGAGG TGCCGTTCTC TCCCCGCTCC GCGCACTCGG
1321 TGCCTGTCTC ACCGCCGTCG CCCGGCGGCT GGTGCGGGCT CTGGCCGCCG CCCTCCGTCC
1381 AAGTCCAGGG CCAGGGCCAA CTCATGGTCC CGAATCCGCT GTCGACAAAG CCCAGTTCCT
1441 CCTCGAGGCA GAAGGCGCAG AAACCCTCGC CGGACGCAGG AGCAAGACCG CCGTCGTCCG
1501 GCGCGCAGCA GGGTGCGAAG CCGGGGGCGG ACAAGAATCT GCGGTTTCTG CTGCAGAAGG
1561 TGCTGAAGCA GAGCGACGTC GGCGCCCTCG GCCGCATCGT GCTCCCCAAA GAAGCGGAGA
1621 CGCACCTGCC GGAGCTCAAG ACGAGGGACG GCATCTCCAT CCCCATGGAG GACATCGGCA
1681 CCTCTCGGGT CTGGAGCATG CGGTACCGGT TTTGGCCTAA CAACAAGAGC AGAATGTATC
1741 TCCTTGAGAA CACTGGGGAC TTTGTTCGCT CAAACGAGCT GCAGGAGGGC GACTTCATCG
1801 TGATTTACTC AGATGTCAAG TCGGGCAAAT ATCTGATACG TGGTGTGAAG GTAAGACCGC
1861 CGCAGGATCT AGCGAAGCAG AAGCATGGCA GTCTAGAGAA AGGCAGCACC TCAGATGCGA
1921 TGCCCTGCGC TGAAGACGGT GGCGCCGAGG CAGGCGGCTG CAAGGGGAAG TCTCCGCACG
1981 GCGTTAGGCG GTCTCGCCAG GAGGCTGCGT CCATGAACCA GATGGCGGTG AGCATCTGAA
2041 AGAACAGCCC TAGACGATCC ACCATTGAAG ACTTAGCTAG CTCGTGTATA CATGATGTTG
2101 ATGATCAAAT CGATCTCTGG CACCGTTGTA TTATCCGTAG TACTCTAGCC CTAGGGATGG
2161 TTATATATTA AAGTAGCTAT CAGTCCGATG TGACGACTAA AGAATGCATG GTTTGGTTCG
2221 TTAAAACCCT GTAACCCTGT ACATGCATGA ACATAATAAC TTATTTGTCG TGTCAATTCG
2281 TCTAACAAGC AGACTAGTTC CTGCCGTAAA AAAAAAAAA AAAA
```

Figure 4(b)

Figure 6A

```
1                                               A-TT-CTC---G-----GGA----------CC---C-CC-GA-GC---CA--GAGGC-GCC--TC-GGCG-G-GCC--CCACGC       45
                                                * ** *** *** *    *           **  *  ** *** ** *  ***** *** ******

46   CGCAGCGCCCGGGGGCAGGCGGGGCGCTTCCGACAAGCAGCGG-CAGCAGG----------------------------------------------------------------       93
     ********* *************************************

94   ------------------------------------------------------------------------------------------------                                     93

94   ------------------------------------------------------------------------GTGCGAGGAC--CC--GGCGGGGCGGCCG                                118
                                                                             ************ ** *****************

119  GCGGGCAGGA--GACAAGAACCC--GCGGTTCCTGCTGCAGAAGTGCTCAAGCAG--AGCGAGTCGGAACC--TCGG--CCGGCATCGTGCTCCCCAAAAAGGA                              212
     **********  ************ ********************************* *************** ************ ************* **

213  AGCGGGAGACTCACCTGCGGA--GCTCAAGACGGGGACGGCATCTC--GATCCCCA--TTGAGG-ACATCGGCACAT-----------CTC                                          286
     ********************   *************************  ****** ***  ********** *****           *
```

Figure 6B

```
287 AGATTTTGGCCCAACAACAAGA-GCAGAATGTA--TCTTCTAGAGAA-CACTGGTGACTTTGTTCGG-TCGAAT-AGCTGCAGGAGG-GTGATTTCATCG        379
    ************************ ** * ************ ** *************************
380 TGCTTTAC---TCTGATGTCAAGTC--GGCAAATATCT---AT-C-C-GGCGTGAAGGTGAGAGCGCA--ACAGGATCTAGCCAAGCACAA--AATGCCAGT--   466
    ********* *************** *** *  ****  ************  *** * ******
467 ---CCAGAGAAAGGCGGGGCTTCC------TGAA--G-CGGGGCGGGAGAAGAC--GGCGGCTGC-AGGAGAAGCCCCCCACGGGCGTCCGGCGATCTCGCCAGGA    555
       *** *  **** *****   ***    ***  **    * ***  * * ** **************************
556 GGCCGGCCTCCATGAACCAGATGGC-GGTGAGCATC-TGAAAATGAGCA-GCTCGCC---GTCCGATCCACCATTGAA-GA-TCAGT-TAGCT-AGCTCAAGT     646
    ***************************  **** **  *  *********** *  *********
647 ATACCC--TTGA-TGATGATCAAAT--CGATC-TCTCGTT-TA-GATCCGTGCTTC-G-GT-A-TGCTGTAGCCCTA-GTTAGGGATGATGATACTAAAGT       734
    ****  ** *** * ************  ** *** ** * ******** *  ***  ** ***********
735 A-CTA-TCGGTCAGATGTGAC-CT-AA-AATGCATGGTCCGTGCTGTT-AACC-GTAT-AA-GCTGTAACCCTT-T-T----AAAAAAAAAAAAAAAA           817
    ****                ********     *          *
```

Figure 8A

```
clone 5 seq         1                                                                                      0
clone 6 seq         1                                                                                      0
clone 9 seq 7/8     1                                                                                      0
tavpl (clone 10)    1 GGCACGAGGACGACTTCATGTTCGGCACGATACCTTCCCGGGACTTCCCTTGCCTCTCCGGTGAGCTCCACCTTCTCCTCCTCGTC 100 clone 5 seq         1                                                                                      0
clone 6 seq         1                                                                                      0
clone 9 seq 7/8     1                                                                                      0
tavpl             101 GTCTTCCAACTCTCCAGGGCTTCACCCGCGCCGTTGGGGGCAGCGGCGCGGGGCCGAGAGTGCGGCGCGGCCGTCCGAGCCTGCCCGAGGGCCCGGG 200 clone 5 seq         1                                                                                      0
clone 6 seq         1                                                                                      0
clone 9 seq 7/8     1                                                                                      0
tavpl             201 GACGGGATGGAGGACCTCTCCGACATCGACCACCTGCTCACTGCTGGATCTTCGCATCAATCAACGAGGAGCTCCCTTGGGACGAGCCGCTCTTCCCCGAGGTCG 300 clone 5 seq         1                                                                                      0
clone 6 seq         1                                                                                      0
clone 9 seq 7/8     1                                                                                      0
tavpl             301 GGATGATGCTGGAGGACTTCATCTCCGAGCAGCAGTTGCAACTCCGGGCGCCCACGCCGGAGAACGGGGTCCATGCGGCTGCTGGTGG 400 clone 5 seq         1                                                                                      0
clone 6 seq         1                                                                                      0
clone 9 seq 7/8     1                                                                                      0
tavpl             401 AGGAGAGGATGCCTTCATGGGTGGCGGCACGGGGAGCCGCGGGGAGCGGCCTTCTTCATGGAGTGGCTCAAGAACAACCGCGACTGCAATC 500
```

Figure 8B

Figure 8C

```
Clone 5 seq    213  TCCGCTGTCGACGAAGTCCAATTCCTCCAAGGCAGAAGCAGAGCAGCCCTCCCGGCGGCCGCCTCCCGGGCGGCCGCCGCCACGCCGCCAG    312
Clone 6 seq    263  TCCGCTGTCGACGAAGTCCAATTCCTCCGAGGCAGAAGCAGAGCAGCCCTCCCGGGATGCAGAGCAGCCGCCGCCGCCACGCCGCCAGCAG    362
Clone 9 seq 7/8 772 TCCGCTGTCGACGAAGTCCAATTCCTCCGAGGCAGAAGCAGAGCAGCCCTCCCGGCGGCCG-GCCGCCACGCCAGCAG                870
tavp1         1301 TCCGCTGTCGACGAAGTCCAATTCCTCCAAGGCAGAAGCAGAGCAGCCCTCCCGGGCGGCCGCCGCCACGCCGCCAG                1400
                    ******************************* *********** ****

Clone 5 seq    313  CGCCCGGGGCAGGCGGCGGCCTTCCGACAAGCAGCGGCAGG                                                   355
Clone 6 seq    363  CGCCCGGGGCAGGCGGCGGCCTTCCGACAAGCAGCGGCAGG                                                   405
Clone 9 seq 7/8 871 CGCCCGGGGCAGGCGGCGGCCTTCCGACAAGCAGTGCAGCAGTCCATGATGCAGAACACCTCTTGCCATCATCGATCGATCCGCATAGA    970
tavp1         1401 CGCCCGGGGCAGGCGGCGGCCTTCCGACAAGCAGTGCAGCAGTCCATGATGCAGAACACCTCTTGCCATCATCGATCGATCCGCATAGA   1500
                    ***************************

Clone 5 seq    356  ---                                                                                         355
Clone 6 seq    406  ---                                                                                         405
Clone 9 seq 7/8 971 ATCACAAGCCATTGCTCCCCAAATAAGTGTGGTACATCGTAACGTAAGAGACGCACATGCTGTCCAGCATCCATCCCGCATCGATGAA   1070
tavp1         1501 ATCACAAGCCATTGCTCCCCAAATAAGTG                                                               1529

Clone 5 seq    356  ---                                                                                         388
Clone 6 seq    406  ---                                                                                         438
Clone 9 seq 7/8 1071 TCACAAGCCATTGCTCCCCTGCACGGTGAATTGCGTTTCTCAACGAGTTCCGTGCATGCGCCAGGTCGAGGAGCGCGGCGCGCGGCGGCAG 1170
tavp1         1530 ---                                                                                         1562
                                                    **************

Clone 5 seq    389  GAGACAAGAACCCGCGGTTCCTGCTGCAGAGAGGTGCTCAAGCAGAGCAGCCCTCGGGCCGCCATCGTCCCCAAA---GAAGCGGAGACTCA 485
Clone 6 seq    439  GAGACAAGAACCCGCGGTTCCTGCTGCAGAGAGGTGCTCAAGCAGAGCAGCCCTCGGGCCGCCATCGTCCCCAAA---GAAGCGGAGACTCA 535
Clone 9 seq 7/8 1171 GAGACAAGAACCCGCGGTTCCTGCTGCAGAGAGGTGCTCAAGCAGAGCAGCCCTCGGGCCGCCATCGTCCCCAAAAAAGGAAGCGGAGACTCA 1270
tavp1         1563 GAGACAAGAACCCGCGGTTCCTGCTGCAGAGAGGTGCTCAAGCAGAGCAGCCCTCGGGCCGCCATCGTCCCCAAA---GAAGCGGAGACTCA 1659
                    *************************************************************************    *************

Clone 5 seq    486  CCTGCCGGAGCTCAAGACGGGGACGGCCATCTCGATCCCATTGAGGACATCGGCACATCTCAG---ATTTTGGCCCAACAAC            565
Clone 6 seq    536  CCTGCCGGAGCTCAAGACGGGGACGGCCATCTCGATCCCATTGAGGACATCGGCACATCTCAG---ATTTTGGCCCAACAAC            635
Clone 9 seq 7/8 1271 CCTGCCGGAGCTCAAGACGGGGACGGCCATCTCGATCCCATTGAGGACATCGGCACATCTCAGTGTGGAGCATGGGTACCGATTTTGGCCCAACAAC 1370
tavp1         1660 CCTGCCGGAGCTCAAGACGGGGACGGCCATCTCGATCCCATTGAGGACATCGGCACATCTCAGTGTGGAGCATGGGTACCGATTTTGGCCCAACAAC 1739
                    ****************************************************************      ****************
```

Figure 8D

```
Clone 5 seq      566  AAGAGCAGAATGTATCTTC-TAGAGAACACTGGTTGTTCGGTGACTTTGTTCATGTGTGCTTTACTCTGATGTCAAGTCG  664
Clone 6 seq      636  AAGAGCAGAATGTATCTTC-TAGAGAACACTGGTTGTTCGGTGACTTTGTTCATGTGTGCTTTACTCTGATGTCAAGTCG  735
Clone 9 seq 7/8 1371  AAGAGCAGAATGTATGTTG-TGGAGAACACTGGTTGTTCGGTGACTTTGTTCATGTGTGCTTTACTCTGATGTCAAGTCG  1469
tavp1           1740  AAGAGCAGAATGTATCTTC-TAGAGAACACTGGTTGTTCGGTGACTTTGTTCATGTGTGCTTTACTCTGATGTCAAGTCG  1838
                      ************* ** * ************************************************************

Clone 5 seq      665  GGCAAATATCTGATACGGGGCGGCGTGAAGGTGAGAGCCGCAACAGAATCTAGCCAAGCACAAGAATGCCAGTCCGACGAAGG  764
Clone 6 seq      736  GGCAAATATCTGATACGGGGCGGCGTGAAGGTGAGAGCCGCAACAGAATCTAGCCAAGCACAAGAATGGCAGTCCGACGAAGG  835
Clone 9 seq 7/8 1470  GGCAAATATCTGATACGGGGCGGCGTGAAGGTAAGAGCCGCAACAGAATCTAGCCAAGCACAAGAATGGCAGTCCGACGAAGG  1569
tavp1           1839  GGCAAATATCTGATACGGGGCGGCGTGAAGGTGAGAGCCGCAACAGAATCTAGCCAAGCACAAGAATGCCAGTCCGACGAAGG  1938
                      ******************************** *********************************** ************

Clone 5 seq      765  CGGGCGGGAGAAGACGGCCGGCTCGCAAGGAGAAGCCCCCCACTCGTCCGGATCTCGCCAGGAGGCCGCCTCCATGAACCAGATGGCGTGAGCATCTG  864
Clone 6 seq      836  CGGGCGGCAGAAGACGGCGGCTGGTTGCAAAGAAGTCTCCGCACGGTGTCCGGATCTCGCCAGGAGGCCGCCTCCATGAACCAGATGGCGTGAGCATCTG  935
Clone 9 seq 7/8 1570  CGGGCGGCAGAAGACGGCGGCTGGTTGCAAAGAAGTCTCCGCACGGTGTCCGGATCTCGCCAGGAGGCCGCCTCCATGAACCAGATGGCGTGAGCATCTG  1669
tavp1           1939  CGGGCGGGAGAAGACGGCCGGCTCGCAAGGAGAAGCCCCCCACCCGTCCGGATCTCGCCAGGAGGCCGCCTCCATGAACCAGATGGCGTGAGCATCTG  2038
                      ******* ********** ** ** *  *  ** ** *** * ** ************************************************

Clone 5 seq      865  AAATGAGCAGGCTCGC--CGTCCGATCCAC-ATTGAAGACTCAGTTAGCTAGCTCAAGTATACCCGTTGATGATGATCAAATCGATCTCCGTTCTATGA  961
Clone 6 seq      936  AAATGAGCAGGCTCGCTCGGCGCGGTCCGATCCCGCCATTGAAGACT-ACTTAGCTAGCTCAAGTATACCTGTTGATGATGATCAAATCGATCTCCGTTCTATGA  1034
Clone 9 seq 7/8 1670  AAATGAGCAGGCTCGCTCGGCGCGGTCCGATCCGCCATTGAAGACT-ACTTAGCTAGCTCAAGTATACCTGTTGATGATGATCAAATCGATCTCCGTTCTATGA  1768
tavp1           2039  AAATGAGCAGGCTCGC--CGTCCGATCCACCGTCCGGCGGTCCGATCCGCCATTGAAGACTCAGTTAGCTAGCTCAAGTATACCCGTTGATGATGATCAAATCGATCTCCGTTCTATGA  2136
                      ****************   *           *   ******* *  ************************** *************************

Clone 5 seq      962  TCCGTGCTTCCGTTCCGTTCGTTACTGCTGTGTAGCCCTAGTTAGGGATGATGATACTAAAGTAGCTATCGGTCAGATGTCAGATGTTGAGCGTCAGATGGTCCGTGCTGTT  1061
Clone 6 seq     1035  TCCGTGCTTCCGTTCCGTTCGTTACTGCTGTGTAGCCCTAGTTAGGGATGGATGATACTAAAGTAGCTATCGGTCAGATGTCAGATGTCAGATGTCAGATGTCAGATGTTGACGCTGAAGATGTCCGTGCTGTT  1134
Clone 9 seq 7/8 1769  TCCGTGCTTCCGTTCCGTTCGTTACTGCTGTGTAGCCCTAGTTAGGGATGGATGATACTAAAGTAGCTATCGGTCAGATGTCAGATGTTGACGCTGAAGATGTCCGTGCTGTT  1868
tavp1           2137  TCCGTGCTTCCGTTCCGTTCGTTACTGCTGTGTAGCCCTAGTTAGGGATGATGATACTAAAGTAGCTATCGGTCAGATGTCAGATGTTGACGCTGAAGATGTCCGTGCTGTT  2236
                      ************************************************* ******************** ************************

Clone 5 seq     1062  AAACCTGTATAAAGGCTGTAACCCTTCTGTACATGCATGAACATACCCTTA----------AAAAAAAAAAAAAAAAAAAAA                   1133
Clone 6 seq     1135  AAACCTGTATAAAG-TGTAA--CCTTCTGTTAAAAAAAAAAAAAAAAAAAA                                                    1185
Clone 9 seq 7/8 1869  AAACCTGTATAAAGGCTGTAACCCTTCTGTAAAAAAAAAAAAAAAAAAA                                                       1916
tavp1           2237  AAACCTGTATAAAGGCTGTAACCCTTCTGTACATGCATGAACATACCCCTATTTGTTGTGTGTCCCTAAAAAAAAAAAAAAAAAAAAAA           2332
                      ************** *****  ******** *       *       *       * * *
```

Northern analysis of *afVP* 1 RNA expression in Wheat Leaf Tissue from Transformed and Untransformed (control) plants:

Figure 10(a)

```
GGCACGAGGACGACTTCATGTTCGCGCACGATACCTTCCCGGCCCTCCCGGACTTCCCTTGCCT
CTCCTCGCCGTCGAGCTCCACCTTCTCCTCCTCGTCGTCTTCCAACTCCTCCAGCGCCTTCACC
CGCGCCGTGGGGGCAGGCGGGCGCGGGGGCGAGAGTGCGCGCGGCGAGCCGTCCGAGCCTGCCG
CGGCCGGGGACGGGATGGACGACCTCTCCGACATCGACCACCTGCTCGACTTCGCATCCATCAA
CGAGGACGTCCCTTGGGACGACGAGCCGCTCTTCCCCGACGTCGGGATGATGCTGGAGGACGTC
ATCTCCGAGCAGCAGCAGTTGCAACCTCCGGCGGGCCACGGCACGGCCGGGAGAACGGCGTCGC
ATGCGGCTGCTGGTGGAGGAGAGGATGCCTTCATGGGTGGCGGCGGCACGGGGAGCGCGGCGGA
CGACCTGCCGCGCTTCTTCATGGAGTGGCTCAAGAACAACCGCGACTGCATCTCGGCCGAGGAC
CTCCGCAGCATCCGCCTCCGTCGATCCACCATCGAGGCCGCGGCCGCGCGCCTCGGTGGGGGC
GCCAGGGCACCATGCAGCTGCTCAAGCTCATCCTCACCTGGGTGCAGAACCACCACCTGCAGAA
GAAGCGCCCCCGCGTCGGCGCCATGGATCAGGAGGCGCTGCCGGCAGGAGGCCAGCTCCCTAGC
CCCGGCGCAAACCCCGGCTACGAATTCCCCGCGGAGACGGGTGCCGCCGCTGCCACATCTTGGA
TTCCCTACCAGGCCTTCTCGCCAACTGGATCCTACGGCGGCGAGGCGATCTACCCGTTCCAGCA
GGGCTGCAGCACGAGCAGCGTGGGCGTGAGCAGCCAGCCGTTCTCCCCGCCGGCGGCGCCCGAC
ATGCACGCCGGGGCCTGGCCGCTGCAGTACGCGGCGTTCGTCCCAGCTGGGGCCACATCCGCAG
GCACTCAAACATACCCGATGCCGCCGCCGGGGGCCGTGCCGCAGCCGTTCGCGGCCCCCGGATT
CGCCGGGCAGTTCCCGCAGCGGATGGAGCCGGCGGCGACCAGGGAGGCCCGGAAGAAGAGGATG
GCGAGGCAGCGGCGCCTGTCGTGCCTGCAGCAGCAGCGGAGCCAGCAGCTGAATCTGAGCCAGA
TCCAAACCGGCGGCTTCCCTCAAGAGCCATCCCCCCGCGCGGCGCACTCGGCGCCGGTCACGCC
GCCGTCGTCTGGCTGGGGAGGCCTCTGGACGCAACAAGCCGTCCAGAGCCAGCCCCATGGCCAG
CTCATGGTCCAGGTCCCGAATCCGCTGTCGACGAAGTCCAATTCCTCAAGGCAGAAGCAGCAAA
AACCCTCGCCGGACGCAGCAGCGAGGCCGCCCTCCGGCGGCGCCGCCACGCCGCAGCGCCCGGG
GCAGGCGGCGGCTTCCGACAAGCAGCGGCAGCAGGTGCATGCATGCACGAACACCTCTTGCCAT
CCATCCATCGATCGCCATCCCGCATAGAATCACAAGCCATTGCTCCCCAAATAAGTGGTGCGAG
GACGCCGGCGGCGGCGCCGGCGGCAGGAGACAAGAACCCGCGGTTCCTGCTGCAGAAGGTGCTC
AAGCAGAGCGACGTCGGAACCCTCGGCCGCATCGTGCTCCCCAAAGAAGCGGAGACTCACCTGC
CGGAGCTCAAGACGGGGACGGCATCTCGATCCCCATTGAGGACATCGGCACATCTCAGATTTT
GGCCCAACAACAAGAGCAGAATGTATCTTCTAGAGAACACTGGTGACTTTGTTCGGTCGAATGA
GCTGCAGGAGGGTGATTTCATCGTGCTTTACTCTGATGTCAAGTCGGGCAAATATCTGATACGC
GGCGTGAAGGTGAGAGCGCAACAGGATCTAGCCAAGCACAAGAATGCCAGTCCAGAGAAAGGCG
GGGCGTCCGACGTGAAGGCGGGCGGAGAAGACGGCGGCTGCAAGGAGAAGCCCCCCCACGGCGT
CCGGCGATCTCGCCAGGAGGCCGCCTCCATGAACCAGATGGCGGTGAGCATCTGAAATGAGCAG
GCTCGCCGTCCGATCCACCATTGAAGACTCAGTTAGCTAGCTCAAGTATACCCGTTGATGATGA
TCAAATCGATCTCTCGTTCTATGATCCGTGCTTCCGTGTACTGCTGTAGCCCTAGTTAGGGATG
ATGATACTAAAGTAGCTATCGGTCAGATGTGACGCTGAAGAATGCATGGTCCGTGCTGTTAAAC
CTGTATAAAGGCTGTAACCCTTCTGTACATGCATGAACATACCCTTATTTGTTGTGTGTTGTCC
TCCTAAAAAAAAAAAAAAAAAAAAAAAAA
``` taVP1

Figure 10(b)

```
GTCCAGAGCCAGCCCCATGGCCAGCTCATGGTCCAGGTCCCGAATCCGCTGTCGACGAAGTCCA
ATTCCTCAAGGCAGAAGCAGCAAAAACCCTCGCCGGACGCAGCAGCGAGGCCGCCCTCCGGCGG
CGCCGCCACGCCGCAGCGCCCGGGGCAGGCGGCGGCTTCCGACAAGCAGCGGCAGCAGGGTGCG
AGGACGCCGGCGGCGGCGCCGGCGGCAGGAGACAAGAACCCGCGGTTCCTGCTGCAGAAGGTGC
TCAAGCAGAGCGACGTCGGAACCCTCGGCCGCATCGTGCTCCCCAAAGAAGCGGAGACTCACCT
GCCGGAGCTCAAGACGGGGGACGGCATCTCGATCCCCATTGAGGACATCGGCACATCTCAGGTG
TGGAGCATGCGATTTTGGCCCAACAACAAGAGCAGAATGTATCTTCTAGAGAACACTGGTGACT
TTGTTCGGTCGAATGAGCTGCAGGAGGGTGATTTCATCGTGCTTTACTCTGATGTCAAGTCGGG
CAAATATCTGATACGCGGCGTGAAGGTGAGAGCGCAACAGGATCTAGCCAAGCACAAGAATGCC
AGTCCAGAGAAAGGCGGGGCGTCCGACGTGAAGGCGGGCGGAGAAGACGGCGGCTGCAAGGAGA
AGCCCCCCCACGGCGTCCGGCGATCTCGCCAGGAGGCCGCCTCCATGAACCAGATGGCGGTGAG
CATCTGAAATGAGCAGGCTCGCCGTCCGATCCACCATTGAAGACTCAGTTAGCTAGCTCAAGTA
TACCCGTTGATGATGATCAAATCGATCTCTCGTTCTATGATCCGTGCTTCCGTGTACTGCTGTA
GCCCTAGTTAGGGATGATGATACTAAAGTAGCTATCGGTCAGATGTGACGCTGAAGAATGCATG
GTCCGTGCTGTTAAACCTGTAAAAGAAAAAAAAAAAAAAAGAAAAAGAAAAAAAAAA
```

Clone 2

Figure 10(c)

```
TGGTCGCAGCATGCCGTCCAGGGCCAGCCCCATGGCCAGCTCATGGTCCAGGTTCCGAATCCGC
TGTCGACGAAGTCCAATTCCTCGAGGCAGAAGCAGCAAAAACCCTCGCCGGATGCAGCAGCGAG
GCCGCCCTCCGGCGGCGCCGCCACGCAGCAGCGCCCGGGGCAGGCGGCGGCTTCCGACAAGCAG
CGGCAGCAGGGTGCGAGGACGCCGGCGGCGGCGCCGGCGGCAGGAGACAAGAACCTGCGGTTCC
TGCTGCAGAAGGTGCTCAAGCAGAGCGACGTCGGAACCCTCGGCCGCATCGTGCTCCCCAAAAA
GGAAGCGGAGACTCACCTGCCGGAGCTCAAGACGGGGGACGGCATCTCGATCCCCATTGAGGAC
ATCGGCACATCTCAGGTGTGGAGCATGCGGTACCGATTTTGGCCCAACAACAAGAGCAGAATGT
ATCTTCTGGAGAACACTGGAGACTTTGTTCGGTCGAATGAGCTGCAGGAGGGTGATTTCATCGT
GCTTTACTCTGATGTCAAGTCGGGCAAATATCTGATACGCGGCGTGAAGGTAAGAGCGCAACAG
GATCTAGCCAAGCACAAGAATGGCAGTCCAGAGAAAGGTGGGGCGTCCGACGCGAAGGCGGGCG
CAGAAGACGGTGGTTGCAAAGAGAAGTCTCCGCACGGTGTCCGGCGATCTCGCCAGGAGGCCGC
CTCCATGAACCAGATGGCCGTGAGCATCTGAAATGAGCAGGCTCGCGCGGTCCGATCCCCATT
GAAGACTACTTAGCTAGCTCAAGTATACCTGTTGATGATGATCAAATCGATCTCCCGTTCTATG
ATCCGTGCTTCCGTGTACTGCTGTAGCCCTAGTTAGGGATGGTGATACTAAAGTAGCTATCGGT
CAGATGTGACGCTGAAGAATGCATGGTCCGTGCTGTTAAACCTGTATAAAGGCTGTAACCCTTC
TGTAAAAAAAAAAAAAAAAAAAAAAAAAAAAAAAAAAAAAAAA
```

Clone 3

Figure 10(d)

```
GGCACGAGCCGCAGCGGATGGAGCCGGCGGCGACCAGGGAGGCCCGGAAGAAGAGGATGGCGAG
GCAGCGGCGCCTGTCGTGCCTGCAGCAGCAGCGGAGCCAGCAGCTGAATCTGAGCCAGATCCAA
ACCGGCGGCTTCCCTCAAGAGCCATCCCCCGCGCGGCGCACTCGGCGCCGGTCACGCCGCCGT
CGTCTGGCTGGGGAGGCCTCTGGACGCAACAAGCCGTCCAGAGCCAGCCCCATGGCCAGCTCAT
GGTCCAGGTCCCGAATCCGCTGTCGACGAAGTCCAATTCCTCAAGGCAGAAGCAGCAAAAACCC
TCGCCGGACGCAGCAGCGAGGCCGCCCTCCGGCGGCGCCGCCACGCCGCAGCGCCCGGGGCAGG
CGGCGGCTTCCGACAAGCAGCGGCAGCAGGGTGCGAGGACGCCGGCGGCGGCGCCGGCGGCAGG
AGACAAGAACCCGCGGTTCCTGCTGCAGAAGGTGCTCAAGCAGAGCGACGTCGGAACCCTCGGC
CGCATCGTGCTCCCCAAAAAGGAAGCGGAGACTCACCTGCCGGAGCTCAAGACGGGGGACGGCA
TCTCGATCCCCATTGAGGACATCGGCACATCTCAGATTTTGGCCCAACAACAAGAGCAGAATGT
ATCTTCTAGAGAACACTGGTGACTTTGTTCGGTCGAATGAGCTGCAGGAGGGTGATTTCATCGT
GCTTTACTCTGATGTCAAGTCGGGCAAATATCTGATACGCGGCGTGAAGGTGAGAGCGCAACAG
GATCTAGCCAAGCACAAGAATGCCAGTCCAGAGAAAGGCGGGGCGTCCGACGTGAAGGCGGGCG
GAGAAGACGGCGGCTGCAAGGAGAAGCCCCCCCACGGCGTCCGGCGATCTCGCCAGGAGGCCGC
CTCCATGAACCAGATGGCGGTGAGCATCTGAAATGAGCAGGCTCGCCGTCCGATCCACCATTGA
AGACTCAGTTAGCTAGCTCAAGTATACCCGTTGATGATGATCAAATCGATCTCTCGTTCTATGA
TCCGTGCTTCCGTGTACTGCTGTAGCCCTAGTTAGGGATGATGATACTAAAGTAGCTATCGGTC
AGATGTGACGCTGAAGAATGCATGGTCCGTGCTGTTAAACCTGTATAAAGGCTGTAACCCTTCT
GTAAAAAAAAAAAAAAAAAAAA
```

Clone 4

Figure 10(e)

```
GGCACGAGGCGGCGCCTGTCGTGCCTGCAGCAGCAGCGGAGCCAGCAGCTGAATCTGAGCCAGA
TCCAAACCGGCGGCTTCCCTCAAGAGCCATCCCCCCGCGCGGCGCACTCGGCGCCGGTCACTCC
GCCGTCGTCTGGCTGGGGAGGCCTCTGGACGCAACAAGCCGTCCAGAGCCAGCCCCATGGCCAG
CTCATGGTCCAGGTCCCGAATCCGCTGTCGACGAAGTCCAATTCCTCAAGGCAGAAGCAGCAAA
AACCCTCGCCGGACGCAGCAGCGAGGCCGCCCTCCGGCGGCGCCGCCACGCCGCAGCGCCCGGG
GCAGGCGGCGGCTTCCGACAAGCAGCGGCAGCAGGGTGCGAGGACGCCGGCGGCGGCGCCGGCG
GCAGGAGACAAGAACCCGCGGTTCCTGCTGCAGAAGGTGCTCAAGCAGAGCGACGTCGGAACCC
TCGGCCGCATCGTGCTCCCCAAAGAAGCGGAGACTCACCTGCCGGAGCTCAAGACGGGGGACGG
CATCTCGATCCCCATTGAGGACATCGGCACATCTCAGATTTTGGCCCAACAACAAGAGCAGAAT
GTATCTTCTAGAGAACACTGGTGACTTTGTTCGGTCGAATGAGCTGCAGGAGGGTGATTTCATC
GTGCTTTACTCTGATGTCAAGTCGGGCAAATATCTGATACGCGGCGTGAAGGTGAGAGCGCAAC
AGGATCTAGCCAAGCACAAGAATGCCAGTCCAGAGAAAGGCGGGGCGTCCGACGTGAAGGCGGG
CGGAGAAGACGGCGGCTGCAAGGAGAAGCCCCCCACGGCGTCCGGCGATCTCGCCAGGAGGCC
GCCTCCATGAACCAGATGGCGGTGAGCATCTGAAATGAGCAGGCTCGCCGTCCGATCCACCATT
GAAGACTCAGTTAGCTAGCTCAAGTATACCCGTTGATGATGATCAAATCGATCTCTCGTTCTAT
GATCCGTGCTTCCGTGTACTGCTGTAGCCCTAGTTAGGGATGATGATACTAAAGTAGCTATCGG
TCAGATGTGACGCTGAAGAATGCATGGTCCGTGCTGTTAAACCTGTATAAAGGCTGTAACCCTT
CTGTACATGCATGAACATACCCTTAAAAAAAAAAAAAAAAAAAAAAA
```

Clone 5

Figure 10(f)

```
CGCAGCGGATGGAACCGGCGGCGACCAGGGAGGCCCGGAAGAAGAGGATGGCGAGGCAGCGGCG
CCTGTCGTGCCTGCAGCAGCAGCGGAGCCAGCAGCTGAATCTGAGCCAGATCCAAAGCGGCGGC
TTCCCTCAAGAACCATCCCCCCGCGCGGCGCACTCGGCGCCGGTCACGCCGCCCTCTTCCGGCT
GGGGAGGCCTCTGGTCGCAGCATGCCGTCCAGGGCCAGCCCCATGGCCAGCTCATGGTCCAGGT
TCCGAATCCGCTGTCGACGAAGTCCAATTCCTCGAGGCAGAAGCAGCAAAAACCCTCGCCGGAT
GCAGCAGCGAGGCCGCCCTCCGGCGGCGCCGCCACGCAGCAGCGCCCGGGGCAGGCGGCGGCTT
CCGACAAGCAGCGGCAGCAGGGTGCGAGGACGCCGGCGGCGGCGCCGGCGGCAGGAGACAAGAA
CCTGCGGTTCCTGCTGCAGAAGGTGCTCAAGCAGAGCGACGTCGGAACCCTCGGCCGCATCGTG
CTCCCCAAAGAAGCGGAGACTCACCTGCCGGAGCTCAAGACGGGGGACGGCATCTCGATCCCCA
TTGAGGACATCGGCACATCTCAGGTGTGGAGCATGCGGTACCGATTTTGGCCCAACAACAAGAG
CAGAATGTATCTTCTGGAGAACACTGGAGACTTTGTTCGGTCGAATGAGCTGCAGGAGGGTGAT
TTCATCGTGCTTTACTCTGATGTCAAGTCGGGCAAATATCTGATACGCGGCGTGAAGGTAAGAG
CGCAACAGGATCTAGCCAAGCACAAGAATGGCAGTCCAGAGAAAGGTGGGGCGTCCGACGCGAA
GGCGGGCGCAGAAGACGGTGGTTGCAAAGAGAAGTCTCCGCACGGTGTCCGGCGATCTCGCCAG
GAGGCCGCCTCCATGAACCAGATGGCCGTGAGCATCTGAAATGAGCAGGCTCGCGCGGTCCGAT
CCCCCATTGAAGACTACTTAGCTAGCTCAAGTATACCTGTTGATGATGATCAAATCGATCTCCC
GTTCTATGATCCGTGCTTCCGTGTACTGCTGTAGCCCTAGTTAGGGATGGTGATACTAAAGTAG
CTATCGGTCAGATGTGACGCTGAAGAATGCATGGTCCGTGCTGTTAAACCTGTATAAAGGCTGT
AACCCTTCTGTTAAAAAAAAAAAAAAAAAAAAAAA
```

Clone 6

Figure 10(g)

```
GGCACGAGCCACCATCGAGGCCGCGGCCGCGCGCCTCGGTGGGGGGCGCCAGGGCACCATGCAG
CTGCTCAAGCTCATCCTCACCTGGGTGCAGAACCACCACCTGCAGAAGAAGCGCCCCGCGTCG
GCGCCATGGATCAGGAGGCGCCGCCGGCAGGAGGCCAGCTCCCCAGCCCCGGCGCAAACCCCGG
CTACGAATTCCCCGCGGAGACGGGTGCCGCCGCTAACACATCTTGGATGCCCTACCAGGCCTTC
TCGCCAACTGGATCCTACGGCGGCGAGGCGATCTACCCGTTCCAGCAGGGCTGCAGCACGAGCA
GCGTGGCCGTGAGCAGCCAGCCGTTCTCCCCGCCGGCGGCGCCCGACATGCACGCCGGGGCCTG
GCCGCTTCAGTACGCGGCGTTCGTCCCAGCTGGGGCCACATCCGCAGGCACTCAAACATACCCG
ATGCCGCCGCCGGGGGCCGTGCCGCAGCCGTTCGCGGCCCCCGGATTCGCCGGGCAGTTCCCGC
AGCGGATGGAACCGGCGGCGACCAGGGAGGCCCGGAAGAAGAGGATGGCGAGGCAGCGGCGCCT
GTCGTGCCTGCAGCAGCAGCGGAGCCAGCAGCTGAATCTGAGCCAGATCCAAAGCGGCGGCTTC
CCTCAAGAACCATCCCCCGCGCGGCGCACTCGGCGCCGGTCACGCCGCCCTCTTCCGGCTGGG
GAGGCCTCTGGTCGCAGCATGCCGTCCAGGGCCAGCCCCATGGCCAGCTCATGGTCCAGGTTCC
GAATCCGCTGTCGACGAAGTCCAATTCCTCGAGGCAGAAGCAGCAAAAACCCTCGCCGGATGCA
GCAGCGAGGCCGCCCTCCGGCGGCGCCGCCACGCAGCAGCGCCCGGGGCAGGCGGCGGCTTCCG
ACAAGCAGCGGCAGCAGGTGCATGCATGCACGAACACCTCTTGCCATCCATCCATCGATCGCCA
TCCCGCATAGAATCACAAGCCATTGCTCCCCAAATAAGTGTGCGTACATCGTAAGAGACGCACA
TCGCTGTCCAGCGATAGGATATCCCCGCATCGCCATCCCGCATAGAATCACAAGCCATTGCTCC
CCTGCACGGTGAATTGCGTTTCTCAACGAGGTTCCGTGCATGCGCGCAGGGTGCGAGGACGCCG
GCGGCGGCGCCGGCGGCAGGAGACAAGAACCTGCGGTTCCTGCTGCAGAAGGTGCTCAAGCAGA
GCGACGTCGGAACCCTCGGCCGCATCGTGCTCCCCAAAAAGGAAGCGGAGACTCACCTGCCGGA
GCTCAAGACGGGGGACGGCATCTCGATCCCCATTGAGGACATCGGCACATCTCAGGTGTGGAGC
ATGCGGTACCGATTTTGGCCCAACAACAAGAGCAGAATGTATCTTCTGGAGAACACTGGAGACT
TTGTTCGGTCGAATGAGCTGCAGGAGGGTGATTTCATCGTGCTTTACTCTGATGTCAAGTCGGG
CAAATATCTGATACGCGGCGTGAAGGTAAGAGCGCAACAGGATCTAGCCAAGCACAAGAATGGC
AGTCCAGAGAAAGGTGGGCGTCCGACGCGAAGGCGGGCGCAGAAGACGGTGGTTGCAAAGAGA
AGTCTCCGCACGGTGTCCGGCGATCTCGCCAGGAGGCCGCCTCCATGAACCAGATGGCCGTGAG
CATCTGAAATGAGCAGGCTCGCGCGGTCCGATCCCCCATTGAAGACTACTTAGCTAGCTCAAGT
ATACCTGTTGATGATGATCAAATCGATCTCCCGTTCTATGATCCGTGCTTCCGTGTACTGCTGT
AGCCCTAGTTAGGGATGGTGATACTAAAGTAGCTATCGGTCAGATGTGACGCTGAAGAATGCAT
GGTCCGTGCTGTTAAACCTGTATAAAGGCTGTAACCCTTCTGTAAAAAAAAAAAAAAAAAA
```

Clone 9

Figure 11

Assignment of *Vp1* cDNA clones to the 3A and 3D genomes of Chinese Spring

PRE-HARVEST SPROUTING

TECHNICAL FIELD

The present invention relates to materials and methods which may be used in the detection and manipulation of Pre-Harvest Sprouting (PHS) and other dormancy-related phenotypes in plants. The present invention also relates to materials and methods for use in plant breeding—in particular to molecular-biology based methods for generating, identifying, characterising or manipulating genetic variation which affects the PHS and other dormancy related traits.

PRIOR ART

Pre-Harvest Sprouting (PHS)

Pre-Harvest Sprouting (PHS) of non-dormant grains is a major limiting factor in achieving consistent bread making quality of UK wheat. Average annual losses due to PHS in the UK wheat crop have been estimated at some £17 million, but the problem is erratic and is much more severe in cool, damp seasons. Variation in the degree of sprouting damage from year to year makes this problem difficult to select against in conventional breeding programmes.

VP1 in Maize and Other Species

Previous work in other plant species has shown that the VIVIPAROUS 1 gene is a major regulator of embryo maturation in maize. Thus McCarty et al (1989) in The Plant Cell 1, 523–532 disclosed that vp1 mutants in maize were abscisic acid (ABA) insensitive, and demonstrated its role in controlling the developmental responses associated with the maturation phase of seed formation. VP1 mutants were shown to germinate precociously. Similarly McCarty et al (1991) in Cell 55, 895–905 disclosed that VP1 encoded 73 kDa transcription factor.

Giraudat et al (1992) in The Plant Cell 4, 1251–1261 showed that Arabidopsis ABI3 mutants had altered seed development & germination. The predicted gene product was similar to VP1 protein. These results and others show that ABI 3/VP1 function as developmental regulators during the maturation stage of embryogenesis by regulating transcription of sets of genes that determine the embryonic phenotype in preparation for desiccation of the seed prior to shedding.

A VP1 homolog in rice has also been isolated (Hattori et al (1994) Plant Molecular Biology 24, 805–810). Similarly in Abstract, Poster No P184 "Poaceae sequence analysis: cloning of a VP-1 homolog from genomic barley DNA via PCR", at the Plant and Animal Genome V Conference in San Diego, USA, January 1997, Wilson & Sorrells disclosed the use of conserved primers to pick out vp1 homologs in Barley.

Wilson speculated that a wheat VP1 homolog may be obtainable by comparison with maize, rice and barley sequences, and (on the basis of comparison with these species) that the R locus may contain a wheat VP1 homolog.

Interestingly, earlier work by Cadle et al (1994) in Genome 37, 129–132 had already shown that the maize vp1 from McCarty didn't hybridise strongly to wheat DNA and could not therefore be used as a probe to map the wheat gene, although various ABA-inducible genes were mapped successfully.

Dormancy

Other recent studies of the genetics of the transition from embryogenesis to germination in maize and Arabidopsis show that mutation of GA (gibberellic acid) and ABA synthesis and sensitivity can alter dormancy levels (Koornneef and Karssen, 1994). For example, whereas the Arabidopsis mutation ga 1 causes a loss of germination due to GA deficiency, aba/abi mutations (that affect ABA synthesis and perception respectively) cause a loss of dormancy (and in strong alleles, loss of viability) because embryos fail to develop desiccation tolerance during maturation (for example alleles of abi 3, Ooms et al., 1993).

It has been suggested that PHS in wheat is the result of the lack of induction of dormancy during embryo development (Gale and Lenton 1987). As is known to those skilled in the art, dormancy is one of two possible developmental states which mature seeds may show following desiccation and shedding (the other being germination). Embryo dormancy develops during late embryogenesis, and results in a lack of germination. Following imbibition of the mature shed seed it results in an inactive phase of plant growth during which development is deferred, although the embryo still maintains a high metabolic activity. Dormancy of mature imbibed seeds occurs even under environmental conditions that would favour germination, indicating that the process is not simply a lack of correct conditions. During dormancy, cells within the mature embryo are maintained in an arrested state, and nuclear DNA values obtained from A. fatua embryos indicate that the cell-cycle is held in G1 and DNA replication does not occur during imbibed dormancy (Elder and Osborne 1993). Dormancy is probably an evolutionary strategy that allows survival of seeds through adverse conditions, and dispersal of seed germination through time. Dormancy is therefore a very important phase of plant development required both for the inhibition of germination prior to completion of embryogenesis, and for the pre-germinative survival of mature seeds. It is also an important agronomic trait, with the market value of wheat being determined, inter alia, by its Hagberg Falling Number, which measures the degree to which some germination-related processes have progressed (discussed in relation to plant breeding hereinafter).

Seeds of the persistent weed A. fatua can show very high levels of embryo dormancy (Simpson 1978).

Embryos with primary dormancy go through a time and environment sensitive process of after-ripening in the dry seed, that is manifested by loss of dormancy in the imbibed seed (Mayer and Poljakoff-Mayber 1989). Dormancy can subsequently be reimposed on after-ripened dry embryos under specific environmental conditions ('induced' or 'secondary' dormancy). These features indicate that signals perceived by the dry seed influence developmental choices following imbibition, resulting in either dormancy or germination (Hilhorst and Karssen 1992). Recent work on the water status of embryos of A. fatua has demonstrated that individual enzymatic and non-enzymatic reactions, rather than metabolic processes control this dormancy/non-dormancy switch in the dry seed (Foley 1994). Others have proposed that the process may involve kinase-phosphatase interactions (Trewavas 1987).

Many studies have analysed the genetic control of embryo dormancy (Hilhorst and Karssen 1992). Results obtained from experiments with inbred lines of A. fatua have suggested that in this species dormancy may be controlled by three loci, two that promote dormancy (L1 and L2), and one that promotes after-ripening (E) (Jana et al., 1979, Jana et al. 1988). These dormancy genes have not been cloned or characterised, their existence was inferred from statistical analysis of segregation for dormancy phenotypes among the progeny from a cross between two different strains.

There is currently a requirement for materials and methods which have utility in the identification or molecular tagging of the genes responsible for PHS in wheat, or which could be used in the manipulation of the PHS trait in wheat or other plants.

Thus it can be seen that the provision of such materials or methods would provide a contribution to the art.

DISCLOSURE OF THE INVENTION

The present inventors have for the first time identified a gene from the oat Avena fatua which encodes a protein which has a high degree of similarity to known VP1/ABI 3 related transcription factors. The expression product of this gene has been termed afVP1.

By studying imbibed mature seeds, the expression of afVP1 has been correlated with the dormant phenotype (primary dormancy, secondary dormancy and after-ripening) in oat. In particular, the present inventors have demonstrated that wild oat has the potential for extremely high levels of dormancy in the mature dry seed, and that expression of afVP 1 is absolutely correlated to the dormant phenotype in imbibed mature seeds. This is the first demonstration of expression of a VP 1-homologue in a developmental situation other than embryogenesis. It indicates that afVP1 activity keeps mature seeds dormant, and inhibits germination— it can thus be used to maintain or impose sufficient intensity and duration of dormancy to avoid PHS before harvest.

In addition to establishing an important role for afVP1 in the control of after-ripening and both primary and secondary dormancy. The present inventors have also employed afVP1 to identify the hitherto unobtained wheat VP1 homolog (hereinafter taVP1) and map its genomic position. As will be discussed in more detail below, the information made available by the present invention has important and industrially applicable implications for the detection and manipulation of PHS and other dormancy related traits in plants, and especially PHS in wheat. In particular work done by the inventors indicates that the ability to keep mature seeds dormant, and inhibit germination, has been lost by the wheat VP 1 due to breeding since domestication which has favoured the evolution of a crippled wheat VP 1 that cannot impose high levels of dormancy (resistance to PHS) on the mature seed.

Introduction of the wild oat afVP 1 into wheat can therefore be used to induce higher levels of dormancy (and thus resistance to PHS) in wheat as afVP 1 compensates for the crippled function of wheat VP 1.

Thus in a first aspect of the present invention there is provided a nucleic acid molecule, encoding afVP1, and having the sequence set out in Seq ID No 1 (shown in FIG. 4 (a)). A further afVP1 sequence, differing slightly from Seq ID No 1, has been deposited in the EMBL database under accession number AFJ001140 after the priority date of the present application.

The existence of an oat homologue to maize VP1 was reported briefly in a poster by M. J. Holdsworth "Dormancy-related expression of the wild oat (Avena fatua) homolog of the maize gene Viviparous 1 (Vp1)". Abstract, Poster No.49, Seventh International Symposium on Pre-Harvest Sprouting in Cereals 1995, Abashiri, Japan, July 1995.

Some comments about its properties were made— however the precise means of cloning the homolog, its sequence, and specific applications for it, were not disclosed.

Additionally Jones et al in April 1997 disclosed that afVP1 was correlated with primary and secondary dormancy (see Jones et al (1997) J Exp Bot 48 (Suppl) 45). Once again no details about how afVP1 could be obtained, or particular applications for it, were disclosed.

The nucleic acid molecules and their encoded polypeptide products (see below) according to the present invention may be provided isolated and/or purified from their natural environment, in substantially pure or homogeneous form, or free or substantially free of nucleic acid or genes of the species of interest or origin other than the sequence encoding a polypeptide with the required function. Nucleic acid according to the present invention may include cDNA, RNA, genomic DNA and may be wholly or partially synthetic.

The term "isolate" encompasses all these possibilities. Where a DNA sequence is specified, e.g. with reference to a figure, unless context requires otherwise the RNA equivalent, with U substituted for T where it occurs, is encompassed.

By virtue of its demonstrated properties, the nucleic acid of the first aspect may has utility, inter alia, in producing transformed crop plants having desirable primary or secondary dormancy, or after-ripening, properties, and in particular may be resistant to PHS.

In a further (second) aspect of the invention there is disclosed variants of the sequence provided, which may for instance be mutants or other derivatives, or naturally occurring alleles (or other homologues, including orthologues) of the sequence.

In the case of mutants and derivatives, the variant encodes a product which is homologous to the sequence of Seq ID No 1, and preferably which retains a functional characteristic that the product encoded by the variant has the afVP1 activity.

By 'afVP1 activity' is meant the ability to act as a transcription factor which is capable of activating some or preferably all of the genes which are activated by afVP1 (e.g. Em, C1) and repressing genes which are repressed by afVP1 (e.g. alpha-amylase—see Hoeker et al 1995 for maize VP1 activity in this regard). This can be assayed either directly using e.g. a reporter gene system linked to any of these genes or their promoters. Alternatively it may be assayed by preparing transformed plants and assaying its phenotypic effects in vivo (i.e. alteration of dormancy as described above).

Methodology for such transformation is described in more detail hereinafter.

Methods for producing such mutants or derivatives based on the sequence provided, and for identifying alleles (or other homologs) and then assessing homology are discussed below, and form one part of this aspect of the invention.

In all cases the nucleic acid molecule which is the mutant or other derivative is ultimately generated either directly or indirectly (e.g. via one or more amplification or replication steps) from oat afVP1 (including alleles thereof), preferably from a nucleic acid molecule comprising all or part of sequence ID No 1.

Changes to a sequence, to produce a mutant or derivative, may be by one or more of addition, insertion, deletion or substitution of one or more nucleotides in the nucleic acid, leading to the addition, insertion, deletion or substitution of one or more amino acids in the encoded polypeptide. Specifically included are parts or fragments (however produced) corresponding to portions of the sequences provided, and which encode polypeptides having afVP1 activity.

Changes may be desirable for a number of reasons, including introducing or removing the following features:

restriction endonuclease sequences; other sites which are required for post translation modification; cleavage sites in the encoded polypeptide; motifs in the encoded polypeptide for post translational modification. All of these may assist in efficiently cloning and expressing an active polypeptide in recombinant form (as described below).

Other desirable mutation may be random or site directed mutagenesis in order to alter the activity (e.g. specificity) or stability of the encoded polypeptide. Particular regions of interest may be those which correspond to the regions of VP 1 which have been shown to function as either a transcriptional activation domain (amino acids 28–121, McCarty et al. 1991), or as a repressor domain (amino acids 238–375, Hoecker et al. 1995). Sections of these regions are highly conserved amongst all the VP 1 homologues (see FIG. 4, and discussion in the Examples) indicating that these sections may provide function to these regions. Comparison of the BR2 region, (shown previously to interact with other classes of transcription factors [Hill et al. 1996]), shows a high degree of similarity between afVP 1 and other homologues, indicating a conservation of function for this part of the protein. These comparisons (in terms of predicted amino acid structure) are shown in FIG. 4.

Those regions which differ from the corresponding parts of other VP1 s may also be of interest in that they may be responsible for the high dormancy demonstrated for oat.

Specifically embraced are derivatives which are truncated, or which have functional regions replaced with corresponding regions from other sources.

As is well-understood, homology at the amino acid level is generally in terms of amino acid similarity or identity.

Similarity allows for conservative variation, i.e. substitution of one hydrophobic residue such as isoleucine, valine, leucine or methionine for another, or the substitution of one polar residue for another, such as arginine for lysine, glutamic for aspartic acid, or glutamine for asparagine. As is well known to those skilled in the art, altering the primary structure of a polypeptide (in this case the afVP1 protein) by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptides conformation.

Also included are homologs generated from afVP1 having non-conservative substitutions. As is well known to those skilled in the art, substitutions to regions of a peptide which are not critical in determining its conformation may not greatly affect its activity because they do not greatly alter the peptide's three dimensional structure. In regions which are critical in determining the peptides conformation or activity such changes may confer advantageous properties on the polypeptide. Indeed, changes such as those described above may confer slightly advantageous properties on the peptide (e.g. altered stability, or DNA binding efficiency).

Similarity or homology (or identity, the terms are used synonymously) may be as defined and determined by the TBLASTN program, of Altschul et al. (1990) *J. Mol. Biol.* 215: 403–10, which is in standard use in the art, or, and this may be preferred, the standard program BestFit, which is part of the Wisconsin Package, Version 8, September 1994, (Genetics Computer Group, 575 Science Drive, Madison, Wis. USA, Wisconsin 53711) BestFit makes an optimal alignment of the best segment of similarity between two sequences. Optimal alignments are found by inserting gaps to maximize the number of matches using the local homology algorithm of Smith and Waterman.

Thus a mutant, derivative or allele (or other homolog) of the present invention shares homology with afVP1. Homology may be at the nucleotide sequence and/or amino acid sequence level. Preferably, the nucleic acid and/or encoded amino acid sequence shares homology with the coding sequence or the sequence encoded by the nucleotide sequence of Seq ID No 1, preferably at least about 50%, or 60%, or 70%, or 80% homology, most preferably at least about 90%, 95%, 96%, 97%, 98% or 99% homology.

Homology may be over the full-length of the relevant sequence shown herein, or may more preferably be over a contiguous sequence of about or greater than about 20, 25, 30, 33, 40, 50, 67, 133, 167, 200, 233, 267, 300, 333, 400, 450, 500, 550, 600 or more amino acids or codons, compared with the relevant amino acid sequence or nucleotide sequence as the case may be.

Thus a variant amino acid sequence in accordance with the present invention may include within the sequence shown in FIG. 4, a single amino acid change with respect to the sequence shown in FIG. 4, or 2, 3, 4, 5, 6, 7, 8, or 9 changes, about 10, 15, 20, 30, 40 or 50 changes, or greater than about 50, 60, 70, 80 or 90 changes. In addition to one or more changes within the afVP1 amino acid sequence shown in FIG. 4, a variant amino acid sequence may include additional amino acids at the C-terminus and/or N-terminus. Naturally, changes to the nucleic acid which make no difference to the encoded amino acid sequence (i.e. 'degeneratively equivalent') are included.

A further part of the present invention provides a method of identifying and cloning further afVP1 homologues or alleles from plant species which method employs a nucleotide sequence as described above.

As mentioned earlier, the present inventors have already used this method to identify a hitherto unidentified wheat VP1 homolog (termed taVP1)—this notwithstanding the failure of earlier workers (e.g. Cadle et al (1994)) who used maize VP1 to probe wheat. Nucleic acid molecules identified using this method form one part of the second aspect of the invention e.g. taVP1, as do mutants and derivatives of those genes.

The originally derived nucleotide sequences of various clones of taVP1 are shown in FIGS. 6 and 8.

Later sequences for the fully sequenced clone (designated taVP1—referred to as Seq ID No 2) and clones 2, 3, 4, 5, 6, and 9 are shown in FIGS. 10(*a*)–(*g*).

It is apparent the sequences shown that none of them encodes a full length protein i.e. they appear to be crippled to various degrees. This has important implications for improving dormancy in wheat, as regards molecular biology-based methods for transforming or breeding improved plants.

It may be noted that McKibbin et al, in a poster at SEB meeting in April 1997 reported using the wild oat homolog of VP1 in N-blots of wheat mRNA from various cultivars to demonstrate that expression levels of certain mRNAs were reduced in non-dormant phenotypes (see McKibbin et al (1997) J Exp Bot 48: (Suppl) 47). However no data regarding the sequence of the putative wheat (or oat) homolog(s) was presented.

When identifying homologs using the strategies below, if need be clones or fragments identified in the search can be extended to produce full length molecules. For instance if it is suspected that they are incomplete, the original DNA source (e.g. a clone library, poly(A)RNA extracted from embryos) can be revisited to isolate missing portions e.g. using sequences, probes or primers based on that portion which has already been obtained to identify other clones containing overlapping sequence.

In one embodiment, nucleotide sequence information provided herein may be used in a data-base (e.g. of ESTs) search to find homologous sequences, expression products of which can be tested for ability as described below.

In a further embodiment, a homolog or allele in accordance with the present invention is also obtainable by means of a method which includes:

(a) providing a preparation of nucleic acid, e.g. a genomic or cDNA library), (b) providing a nucleic acid molecule having a nucleotide sequence shown in or complementary to a nucleotide sequence shown in Seq ID No 1 preferably from within the coding sequence (i.e. encoding for the afVP1 amino acid sequence shown in FIG. 4), most preferably the probe used is distinctive or characteristic of afVP1 rather than other, known, VP1 analogs, (c) contacting nucleic acid in said preparation with said nucleic acid molecule under conditions for hybridisation of said nucleic acid molecule to any said gene or homologue in said preparation, and identifying said gene or homologue if present by its hybridisation with said nucleic acid molecule.

"Distinctive" or "characteristic" regions of afVP1 can be determined with reference to comparisons with know VP 1 homologues, for instance those shown in FIG. 4. Such regions and specific oligonucleotides are found away from the conserved regions which are described in more detail in Example 2 below, and will allow those skilled on the art to design probes and primers which will not hybridise with prior art sequences.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells.

Test nucleic acid may be provided from a cell as genomic DNA, cDNA or RNA, or a mixture of any of these, preferably as a library in a suitable vector. If genomic DNA is used the probe may be used to identify untranscribed regions of the gene (e.g. promoters etc.), such as is described hereinafter.

Preliminary experiments may be performed by hybridising under low stringency conditions. For probing, preferred conditions are those which are stringent enough for there to be a simple pattern with a small number of hybridisations identified as positive which can be investigated further.

It is well known in the art to increase stringency of hybridisation gradually until only a few positive clones remain. Suitable conditions would be achieved when a large number of hybridising fragments were obtained while the background hybridisation was low. Using these conditions nucleic acid libraries, e.g. cDNA libraries representative of expressed sequences, may be searched. Those skilled in the art are well able to employ suitable conditions of the desired stringency for selective hybridisation, taking into account factors such as oligonucleotide length and base composition, temperature and so on.

For instance, screening may initially be carried out under conditions, which comprise a temperature of about 37° C. or less, a formamide concentration of less than about 50%, and a moderate to low salt (e.g. Standard Saline Citrate ('SSC')=0.15 M sodium chloride; 0.15 M sodium citrate; pH 7) concentration.

Alternatively, a temperature of about 50° C. or less and a high salt (e.g. 'SSPE'=0.180 mM sodium chloride; 9 mM disodium hydrogen phosphate; 9 mM sodium dihydrogen phosphate; 1 mM sodium EDTA; pH 7.4). Preferably the screening is carried out at about 37° C., a formamide concentration of about 20%, and a salt concentration of about 5×SSC, or a temperature of about 50° C. and a salt concentration of about 2×SSPE. These conditions will allow the identification of sequences which have a substantial degree of homology (similarity, identity) with the probe sequence, without requiring the perfect homology for the identification of a stable hybrid e.g. 70% homology.

Suitable conditions include, e.g. for detection of sequences that are about 80–90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include amplification using PCR (see below), RN'ase cleavage and allele specific oligonucleotide probing. The identification of successful hybridisation is followed by isolation of the nucleic acid which has hybridised, which may involve one or more steps of PCR or amplification of a vector in a suitable host.

In a further embodiment, hybridisation of nucleic acid molecule to an allele or homologue may be determined or identified indirectly, e.g. using a nucleic acid amplification reaction, particularly the polymerase chain reaction (PCR). PCR requires the use of two primers to specifically amplify target nucleic acid, so preferably two nucleic acid molecules with sequences characteristic of afVP1 are employed. However, if RACE is used (see below) only one such primer may be needed.

PCR techniques for the amplification of nucleic acid are described in U.S. Pat. No. 4,683,195 and Saiki et al.

*Science* 239: 487–491 (1988). References for the general use of PCR techniques include Mullis et al, Cold Spring Harbor Symp. Quant. Biol., 51:263, (1987), Ehrlich (ed), PCR technology, Stockton Press, N.Y., 1989, Ehrlich et al, *Science*, 252:1643–1650, (1991), "PCR protocols; A Guide to Methods and Applications", Eds. Innis et al, Academic 795 Press, New York, (1990).

Prior to any PCR that is to be performed, the complexity of a nucleic acid sample may be reduced where appropriate by creating a cDNA library for example using RT-PCR or by using the phenol emulsion reassociation technique (Clarke et al. (1992) NAR 20, 1289–1292) on a genomic library.

Thus a method involving use of PCR in obtaining nucleic acid according to the present invention may include:

(a) providing a preparation of plant nucleic acid, (b) providing a pair of nucleic acid molecule primers useful in (i.e. suitable for) PCR, at least one said primers having a sequence shown in or complementary to a sequence shown in Seq ID No 1 as described in above, (c) contacting nucleic acid in said preparation with said primers under conditions for performance of PCR, (d) performing PCR and determining the presence or absence of an amplified PCR product. The presence of an amplified PCR product may indicate identification of a gene of interest or fragment thereof.

Thus the methods of the invention may include hybridisation of one or more (e.g. two) probes or primers to target nucleic acid. Where the nucleic acid is double-stranded DNA, hybridisation will generally be preceded by denaturation to produce single-stranded DNA. The hybridisation may be as part of a PCR procedure, or as part of a probing procedure not involving PCR. An example procedure would be a combination of PCR and low stringency hybridisation. A screening procedure, chosen from the many available to those skilled in the art, is used to identify successful hybridisation events and isolated hybridised nucleic acid.

An oligonucleotide for use in probing or PCR may be about 30 or fewer nucleotides in length (e.g. 18, 21 or 24). Generally specific (i.e. "distinctive" or "characteristic") primers are upwards of 14 nucleotides in length. For optimum specificity and cost effectiveness, primers of 16–24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length.

Some preferred oligonucleotides have a corresponding to bases 1 to 892 or 600 to 892 of Seq ID No 1. Primers may correspond to 1398 to 1417 or 2272 to 2290 of Seq ID No 1 (which is 1410–1429 and 2285–2302 on the afVP1 sequence deposisted on the EMBL database under accession number AFJ001140).

In a further (third) aspect of the present invention, the nucleic acid described above is in the form of a recombinant and preferably replicable vector.

"Vector" is defined to include, inter alia, any plasmid, cosmid, phage or Agrobacterium binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in both the actinomycetes and related species and in bacteria and/or eucaryotic (e.g. higher plant, mammalian, yeast or fungal cells).

A vector including nucleic acid according to the present invention need not include a promoter or other regulatory sequence, particularly if the vector is to be used to introduce the nucleic acid into cells for recombination into the genome.

However, in a preferred embodiment, the nucleic acid in the vector is under the control of (operably linked to) an appropriate promoter or other regulatory elements for expression in a host cell such as a microbial, e.g. bacterial, or plant cell. In the case of genomic DNA, this may contain its own promoter or other regulatory elements and in the case of cDNA this may be under the control of an appropriate promoter or other regulatory elements for expression in the host cell.

By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

Generally speaking, those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual*: 2nd edition, Sambrook et al, 1989, Cold Spring Harbor Laboratory Press.

Many known techniques and protocols for manipulation of nucleic acid, for example in preparation of nucleic acid constructs, mutagenesis (see above), sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference. Specific procedures and vectors previously used with wide success upon plants are described by Bevan (Nucl. Acids Res. 12, 8711–8721 (1984)) and Guerineau and Mullineaux (1993) (Plant transformation and expression vectors. In: Plant Molecular Biology Labfax (Croy RRD ed) Oxford, BIOS Scientific Publishers, pp 121–148).

If desired, selectable genetic markers may be used consisting of chimaeric genes that confer selectable phenotypes such as resistance to antibiotics such as kanamycin, hygromycin, phosphinotricin, chlorsulfuron, methotrexate, gentamycin, spectinomycin, imidazolinones and glyphosate.

Thus this aspect of the invention provides a gene construct, preferably a replicable vector, comprising a promoter operatively linked to a nucleotide sequence provided by the present invention, such as the afVP1 gene shown in Seq ID No 1, a homologue thereof (e.g. taVP1), or any active mutant, derivative or allele thereof.

Suitable promoters include the Cauliflower Mosaic Virus 35S (CaMV 35S) gene promoter that is expressed at a high level in virtually all plant tissues (Benfey et al, 1990a and 1990b); the cauliflower meri 5 promoter that is expressed in the vegetative apical meristem as well as several well localised positions in the plant body, e.g. inner phloem, flower primordia, branching points in root and shoot (Medford, 1992; Medford et al, 1991) and the Arabidopsis thaliana LEAFY promoter that is expressed very early in flower development (Weigel et al, 1992).

Another strong promoter is the rice actin promoter. Also advantageous in the present context is the ubiquitin promoter which is expressed strongly in embryos (see Christenson & Quail (1996) Transgenic Research 5: 2133–2218.

Previous work in Arabidopsis has shown that constitutive expression of ABI 3 causes no negative effects on plant growth, and so expression of afVP 1 throughout a plant (e.g. wheat) may not have negative side effects on wheat plant growth.

However the promoter may include one or more sequence motifs or elements conferring developmental and/or tissue-specific regulatory control of expression. Other regulatory sequences may be included, for instance as identified by mutation or digest assay in an appropriate expression system or by sequence comparison with available information, e.g. using a computer to search on-line databases.

Thus in another embodiment of this aspect of the present invention, there is provided a gene construct, preferably a replicable vector, comprising an inducible promoter operably linked to a nucleotide sequence provided by the present invention, such as the afVP1 gene, a homolog from another plant species, e.g. a wheat taVP1, or any mutant, or allele thereof.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level which brings about the desired phenotype.

A suitable inducible promoter is the GST-II-27 gene promoter which has been shown to be induced by certain chemical compounds which can be applied to growing plants. The promoter is functional in both monocotyledons and dicotyledons. It can therefore be used to control gene expression in a variety of genetically modified plants, including field crops such as canola, sunflower, tobacco, sugarbeet, cotton; cereals such as wheat, barley, rice, maize, sorghum; fruit such as tomatoes, mangoes, peaches, apples, pears, strawberries, bananas, and melons; and vegetables such as carrot, lettuce, cabbage and onion. The GST-II-27 promoter is also suitable for use in a variety of tissues, including roots, leaves, stems and reproductive tissues.

Other advantageous promoters may be those which function at particular developmental stages (e.g. embryogenesis)—for instance the Em promoter, or the taVP1 wheat promoter which is discussed hereinafter.

In a fourth aspect the present invention also provides methods comprising introduction of such a construct into a plant cell and/or induction of expression of a construct within a plant cell, by application of a suitable stimulus, an effective exogenous inducer.

The vectors described above may be introduced into hosts by any appropriate method e.g. conjugation, mobilisation, transformation, transfection, transduction or electoporation.

However, when introducing a chosen gene construct into a cell, certain considerations must be taken into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material either will or will not occur. Finally, as far as plants are concerned the target cell type must be such that cells can be regenerated into whole plants (see below).

Plants transformed with the DNA segment containing the sequence may be produced by standard techniques which are already known for the genetic manipulation of plants. DNA can be transformed into plant cells using any suitable technology, such as a disarmed Ti-plasmid vector carried by Agrobacterium exploiting its natural gene transfer ability (EP-A-270355, EP-A-0116718, NAR 12(22) 8711–87215 1984), particle or microprojectile bombardment (US 5100792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614 Gelvin Debeyser—see attached) other forms of direct DNA uptake (DE 4005152, WO 9012096, US 4684611), liposome mediated DNA uptake (e.g. Freeman et al. *Plant Cell Physiol*. 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv*. 9: 1–11.

Agrobacterium transformation is widely used by those skilled in the art to transform dicotyledonous species. Recently, there has been substantial progress towards the routine production of stable, fertile transgenic plants in almost all economically relevant monocot plants (Toriyama, et al. (1988) *Bio/Technology* 6, 1072–1074; Zhang, et al. (1988) *Plant Cell Rep.* 7, 379–384; Zhang, et al. (1988) *Theor Appl Genet* 76, 835–840; Shimamoto, et al. (1989) *Nature* 338, 274–276; Datta, et al. (1990) *Bio/Technology* 8, 736–740; Christou, et al. (1991) *Bio/Technology* 9, 957–962; Peng, et al. (1991) International Rice Research Institute, Manila, Philippines 563–574; Cao, et al. (1992) *Plant Cell Rep.* 11, 585–591; Li, et al. (1993) *Plant Cell Rep.* 12, 250–255; Rathore, et al. (1993) *Plant Molecular Biology* 21, 871–884; Fromm, et al. (1990) *Bio/Technology* 8, 833–839; Gordon-Kamm, et al. (1990) *Plant Cell* 2, 603–618; D'Halluin, et al. (1992) *Plant Cell* 4, 1495–1505; Walters, et al. (1992) *Plant Molecular Biology* 18, 189–200; Koziel, et al. (1993) *Biotechnology* 11, 194–200; Vasil, I. K. (1994) *Plant Molecular Biology* 25, 925–937;

Weeks, et al. (1993) *Plant Physiology* 102, 1077–1084; Somers, et al. (1992) *Bio/Technology* 10, 1589–1594; WO92/14828). In particular, Agrobacterium mediated transformation is now emerging also as an highly efficient alternative transformation method in monocots (Hiei et al. (1994) *The Plant Journal* 6, 271–282).

Particularly of interest on the present case is the fact that the generation of fertile transgenic plants has been achieved in the cereals rice, maize, wheat, oat, and barley (reviewed in Shimamoto, K. (1994) *Current Opinion in Biotechnology* 5, 158–162.; Vasil, et al. (1992) *Bio/Technology* 10, 667–674; Vain et al., 1995, *Biotechnology Advances* 13 (4): 653–671; Vasil, 1996, *Nature Biotechnology* 14 page 702).

Microprojectile bombardment, electroporation and direct DNA uptake are preferred where Agrobacterium is inefficient or ineffective. Alternatively, a combination of different techniques may be employed to enhance the efficiency of the transformation process, eg bombardment with Agrobacterium coated microparticles (EP-A-486234) or microprojectile bombardment to induce wounding followed by co-cultivation with Agrobacterium (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants*, Vol I, II and III, *Laboratory Procedures and Their Applications*, Academic Press, 1984, and Weissbach and Weissbach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

Thus this aspect of the present invention includes a method of transforming a plant cell involving introduction of a vector comprising the afVP1 sequence (or a mutant or derivative thereof) into a plant cell and causing or allowing recombination between the vector and the plant cell genome to introduce the sequence of nucleotides into the genome.

In a fifth aspect of the invention, there is disclosed a host cell containing nucleic acid or a vector according to the present invention, especially a plant or a microbial cell.

The invention further encompasses a host cell transformed with nucleic acid or a vector according to the present invention, especially a plant or a microbial cell, and most preferably a crop plant e.g. wheat. Within the cell, the nucleic acid may be incorporated within the chromosome. There may be more than one heterologous nucleotide sequence per haploid genome.

Thus in one embodiment of the invention there is provided a plant cell having incorporated into its genome nucleic acid, particularly heterologous nucleic acid, as provided by the present invention, under operative control of a regulatory sequence for control of expression. The coding sequence may be operably linked to one or more regulatory sequences which may be heterologous or foreign to the gene, such as not naturally associated with the gene for its expression. The nucleic acid according to the invention may be placed under the control of an externally inducible gene promoter to place expression under the control of the user.

The term "heterologous" is used broadly in this aspect to indicate that the gene/sequence of nucleotides in question have been introduced into said cells of the plant or an ancestor thereof, using genetic engineering, i.e. by human intervention. A heterologous gene (e.g. authentic afVP1) may replace an endogenous equivalent gene (e.g. taVP1; i.e. one which normally performs the same or a similar function) or the inserted sequence may be additional to the endogenous gene or other sequence. The heterologous (or exogenous or foreign) nucleic acid may be non-naturally occurring in cells of that type, variety or species. Thus the heterologous nucleic acid may comprise a coding sequence of or derived from a particular type of plant cell or species or variety of plant, placed within the context of a plant cell of a different type or species or variety of plant. A further possibility is for a nucleic acid sequence to be placed within a cell in which it or a homolog is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression.

In the transgenic plant cell (i.e. transgenic for the nucleic acid in question) the transgene may be on an extra-genomic vector or incorporated, preferably stably, into the genome.

A plant may be regenerated from one or more transformed plant cells described above. Such plants form a sixth aspect of the invention.

A plant according to the present invention may be one which does not breed true in one or more properties. Plant varieties may be excluded, particularly registrable plant varieties according to Plant Breeders' Rights. it is noted that a plant need not be considered a "plant variety" simply because it contains stably within its genome a transgene, introduced into a cell of the plant or an ancestor thereof.

In addition to a plant, the present invention provides any clone of such a plant, seed, selfed or hybrid progeny is and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, offspring, clone or descendant.

Particularly embraced are the seeds or grains of a transformed plant as described above, and also products (e.g. human and animal foodstuffs) derived from or containing such seeds or grains.

In a seventh aspect, the invention provides a method of influencing or affecting the dormancy characteristics of a plant, preferably the viviparous or PHS phenotype of a plant, including the step of causing or allowing expression of a heterologous nucleic acid sequence, as discussed in relation to the first and second aspects of the invention, within cells of the plant.

This aspect particularly provides a method of including expression from nucleic acid Seq ID No 1 or 2, or a mutant, allele or derivative of those sequences, within cells of a plant (thereby producing the encoded polypeptide), following an earlier step of introduction of the nucleic acid into a cell of the plant or an ancestor thereof. The method may employ the vectors of the third aspect.

In the present invention, expression (or over-expression or endogenous sequences) may be achieved by introduction of the nucleotide sequence in a "sense" orientation. Thus, the present invention provides a method of the method including causing or allowing expression of the product (polypeptide or nucleic acid transcript) encoded by heterologous nucleic acid according to the invention from that nucleic acid within cells of the plant.

The complete sequence corresponding to the coding sequence of afVP1 need not be used. For example fragments (i.e. active derivatives or mutants) of sufficient length may be used.

The sequence employed may be about 500 nucleotides or less, possibly about 400 nucleotides, about 300 nucleotides, about 200 nucleotides, or about 100 nucleotides. It may be possible to use oligonucleotides of much shorter lengths, 14–23 nucleotides, although longer fragments, and generally even longer than about 500 nucleotides are preferable where possible, such as longer than about 600 nucleotides, than about 700 nucleotides, than about 800 nucleotides, than about 1000 nucleotides or more.

Down-regulation of expression of a target gene (e.g. a homolog identified in accordance with the second aspect of the invention such as taVP1—Seq ID No 2) may be achieved using anti-sense technology or "sense regulation" ("co-suppression").

For instance, if it is desired to suppress dormancy (i.e. enhance PHS or 'malting') then the nucleic acids of the present invention (e.g. taVP1, afVP1, other derivatives) may be used for this purpose in accordance with standard procedures for anti-sense or sense suppression.

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724–726; Zhang et al, (1992) *The Plant Cell* 4, 1575–1588, English et al., (1996) *The Plant Cell* 8, 179–188. Antisense technology is also reviewed in Bourque, (1995), *Plant Science* 105, 125–149, and Flavell, (1994) *PNAS USA* 91, 3490–3496.

An alternative is to use a copy of all or part of the target gene inserted in sense, that is the same, orientation as the target gene, to achieve reduction in expression of the target gene by co-suppression. See, for example, van der Krol et al., (1990) *The Plant Cell* 2, 291–299; Napoli et al., (1990) *The Plant Cell* 2, 279–289; Zhang et al., (1992) *The Plant Cell* 4, 1575–1588, and U. S. Pat. No. 5,231,020. Recent work indicates that foreign (non-endogenous) homologous sequences may be particularly effective at inducing gene silencing in targeted endogenous genes. See e.g. Matzke, M. A. and Matzke, A. J. M. (1995), *Trends in Genetics*, 11: 1–3). This sequence homology may involve promoter regions or coding regions of the silenced gene (Matzke, M. A. and Matzke, A. J. M. (1993) *Annu. Rev. Plant Physiol. Plant Mol. Biol.*, 44: 53–76, Vaucheret, H. (1993) *C. R. Acad. Sci. Paris*, 316: 1471–1483, Vaucheret, H. (1994), *C. R. Acad. Sci. Paris*, 317: 310–323, Baulcombe, D. C. and English, J. J. (1996), Current Opinion In Biotechnology, 7: 173–180, Park, Y-D., et al (1996), *Plant J.*, 9: 183–194.

Thus the sequences of the present invention may have utility when used in plant species different to those from which they were derived (e.g. barley). In an eight aspect, the present invention also encompasses the expression product of any of the nucleic acid sequences disclosed, particularly those of the first and second aspects, and methods of making the expression product by expression from encoding nucleic acid therefore under suitable conditions, which may be in suitable host cells.

Following expression, the product may be isolated from the expression system (e.g. microbial) and may be used as desired, for instance in formulation of a composition including at least one additional component.

Alternatively (and indeed preferably) the product may perform its function in vivo, in this context the function being to influence the dormancy characteristics of a plant, preferably the viviparous or PHS phenotype of a plant.

In an ninth aspect, purified or semi-purified afVP1 or taVP1 protein, or a fragment, mutant, derivative or other variant thereof, e.g. produced recombinantly by expression from encoding nucleic acid therefor, may be used to raise antibodies employing techniques which are standard in the art. Antibodies and polypeptides comprising antigen-binding fragments of antibodies may be used in identifying homologs from other species as discussed further below, and also in labelling proteins.

Methods of producing antibodies include immunising a mammal (e.g. human, mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, Nature 357: 80–82). Antibodies may be polyclonal or monoclonal. As an alternative or supplement to immunising a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibodies may have utility in testing for endogenous VP1-analog expression (especially taVP1 expression in wheat) as part of a dormancy/PHS assessment, as is discussed hereinafter.

Antibodies raised to a polypeptide or peptide can be used in the identification and/or isolation of homologous polypeptides, and then their encoding genes.

Thus, the present invention provides a method of identifying or isolating a polypeptide having one or more afVP1 (or taVP1 ) epitopes comprising screening candidate polypeptides with a polypeptide comprising the antigen-binding domain of an antibody (for example whole antibody or a fragment thereof) which is able to bind afVP1 (or taVP1 ) or a fragment or a derivative thereof or preferably has binding specificity for such a polypeptide.

Thus specific binding members such as antibodies and polypeptides comprising antigen binding domains of antibodies that bind and are preferably specific for afVP1 or taVP1 polypeptides or mutants or derivatives thereof represent part of the present invention, as do their use and methods which employ them.

Candidate polypeptides for screening may for instance be the products of an expression library created using nucleic acid derived from an plant of interest, or may be the product of a purification process from a natural source. A polypeptide found to bind the antibody may be isolated and then may be subject to amino acid sequencing. Any suitable technique may be used to sequence the polypeptide either wholly or partially (for instance a fragment of the polypeptide may be sequenced). Amino acid sequence information may be used in obtaining nucleic acid encoding the polypeptide, for instance by designing one or more oligonucleotides (e.g. a degenerate pool of oligonucleotides) for use as probes or primers in hybridization to candidate nucleic acid, or by searching computer sequence databases, as discussed further below.

The above description has generally been concerned with the coding parts of the afVP1 gene, and uses therefor. Also embraced within the present invention are untranscribed parts of that gene, or the taVP1 gene.

Thus a tenth aspect of the invention is a nucleic acid molecule encoding the promoter of the afVP1 gene or the taVP1 gene.

The promoter region may be readily identified using a probe or primer based on Seq ID No 1 or Seq ID no 2, as described in relation to earlier aspects. This can be used in the identification and isolation of a promoter from a genomic library containing DNA derived from a plant source. Techniques and conditions for such probing are well known in the art as is discussed above. Following probing, promoter activity is assessed using a test transcription system.

"Promoter activity" is used to refer to ability to initiate transcription. The level of promoter activity is quantifiable for instance by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridise with the mRNA and which are labelled or may be used in a specific amplification reaction such as the polymerase chain reaction.

Use of a reporter gene facilitates determination of promoter activity by reference to protein production. The reporter gene preferably encodes an enzyme which catalyses a reaction which produces a detectable signal, preferably a visually detectable signal, such as a coloured product. Many examples are known, including β-galactosidase and luciferase. β-galactosidase activity may be assayed by production of blue colour on substrate, the assay being by eye or by use of a spectro-photometer to measure absorbance. Fluorescence, for example that produced as a result of luciferase activity, may be quantitated using a spectrophotometer. Radioactive assays may be used, for instance using chloramphenicol acetyltransferase, which may also be used in non-radioactive assays. The presence and/or amount of gene product resulting from expression from the reporter gene may be determined using a molecule able to bind the product, such as an antibody or fragment thereof. The binding molecule may be labelled directly or indirectly using any standard technique.

Those skilled in the art are well aware of a multitude of possible reporter genes and assay techniques which may be used to determine promoter activity. Any suitable reporter/assay may be used and it should be appreciated that no particular choice is essential to or a limitation of the present invention.

Also embraced by the present invention is a promoter which is a mutant, derivative, or other homolog of the promoter identified as above. These can be generated or identified in similar manner to the derivatives discussed in the second aspect; they will share homology with the taVP1 or afVP1 promoters and retain promoter activity.

To find minimal elements or motifs responsible for tissue and/or developmental regulation, restriction enzyme or nucleases may be used to digest a nucleic acid molecule, or mutagenesis may be employed, followed by an appropriate assay (for example using a reporter gene such as luciferase) to determine the sequence required. Nucleic acid comprising these elements or motifs forms one part of the present invention.

In an eleventh aspect of the invention there is provided a nucleic acid construct, preferably an expression vector, including a promoter region or fragment, mutant, derivative or other homolog or variant thereof able to promote transcription as discussed above, operably linked to a heterologous gene, e.g. a coding sequence, which is preferably not the coding sequence with which the promoter is operably linked in nature.

The above aspects of the invention are concerned generally with methods and materials which have utility, inter alia, in manipulating PHS and/or other dormancy related traits (secondary and after-ripening) in crops, particularly wheat, by means of transformation.

However the identification of the wheat homolog taVP1 by the present inventors has also opened up the possibility of improved methods for generating plants having desirable characteristics as regards PHS and/or other dormancy related traits. These methods have as their basis the identification and molecular tagging of the taVP1 gene (using taVP1 cDNA as a probe in genomic southern blots) which has been achieved by the present inventors, as described below.

A plant breeding approach to improving the PHS properties of wheat has a number of advantages over transformation approaches, particularly as regards consumer confidence in the improved products and ease of regulatory approval.

Essentially, plant breeding is the process of bringing together new combinations of genes, from different parents, allowing them to reassort into recombinant genotypes carrying various mixtures of the original parental genes, then selecting individual progenies which carry genetic combinations superior to the original parents.

Dormancy is one of a number of characteristics described as "quantitative traits" (i.e. varies over a continuous range as opposed to a trait such as grain colour which is an "all or nothing", discontinuous character).

Quantitative traits (=QTs) are controlled by several/many genes (situated on the chromosomes at several/many Quantitative Trait Loci=QTLs); and by "environmental" variables including weather effects and experimental uncertainties of measurement. Breeding for desirable QTs thus demands the ability to effectively discriminate between genetic variants at a large number of QTLs, conventionally by using statistical techniques based on large samples and repeated trials.

Dormancy is a particularly difficult QT for the plant breeder because the effects of "error" variables are comparatively large, the trait itself is lost gradually during after-ripening, and experimental methods for testing dormancy are time/labour/material intensive. Since dormancy tests have to be carried out between one harvest and the next sowing (sometimes just a month or so), only limited time is available for empirical testing; for this reason wheat breeders usually defer dormancy testing until the later stages of a breeding programme when only a limited number of "elite" progenies have passed through earlier rounds of selection for other, more easily selectable characters. This has the effect of reducing the amount of control which the breeder can exercise over the genetic combinations of dormancy QTLs passing into his new varieties.

When selecting progeny, rather than use "direct" selection for dormancy (i.e. by measuring the trait itself), in which genetic combinations are unconsciously chosen on the basis of their statistical performance in empirical tests, it is possible to exploit "marker aided" selection, choosing progenies on the basis of discontinuous traits, each of which is simply controlled by genetic variants at a single (or small number) of genetic locus/loci. The conventional marker for dormancy in wheat is grain colour; it has been known for many years that red-seeded wheats tend to be more dormant than white-seeded wheats, and that grain colour is determined by dominant "red" versus recessive "white" alleles (gene variants) at three major gene loci. By discarding any white-seeded progenies (detected by visual inspection after steeping grains in dilute aqueous sodium hydroxide) wheat breeders aim to eliminate the undesirable lack of dormancy associated with this character.

Thus one approach to breeding for PHS resistance is disclosed by Derera NF (1989) in "Breeding for pre-harvest sprouting tolerance". pp111–128 in: NF Derera (Ed), "Pre-Harvest Field Sprouting in Cereals. CRC Press Inc." This gives some specific examples of breeding programmes which have been undertaken to produce new varieties with improved dormancy, including exploitation of red grain colour, breeding for dormancy in white-grained wheats, screening wheat genotypes for use as donors of dormancy genes in breeding, and a suggested scheme for dormancy breeding. The use of the Hagberg falling number test (to assess the viscosity of ground kernel material under moist and dry conditions) is also discussed as being a useful measure of sprouting resistance.

Another discussion of PHS is found in Mares D J (1989) "Pre-harvest sprouting damage and sprouting tolerance: assay methods and instrumentation." pp129–170 in the same volume as Derera (supra). This disclosed various methods used to select against sprouting. The Hagberg test, and its approval by various standardisation bodies, is also discussed. It is noted that an absence of sprouting damage (indicative of low PHS susceptibility) leads to high falling numbers (>400, generally 450–550).

The role of grain colour in dormancy, and its relationship with VP1, has been discussed in number of prior art papers.

For instance the poster by Wilson (described in the prior art section above) discussed the possible orthology of the Red grain locus in wheat to the maize VP-1 locus. Similarly Sorrells & Wilson (1997) Crop Science 37: 691–697 discusses the relationship between maize red pericarp colour (controlled by the Pi gene) nd VP1, and suggests that a (postulated) wheat VP1 homolog may express via a P homolog.

Unfortunately the association between grain redness and dormancy is not hard and fast: breeders of white-grained wheats (eg. Australia) or amber wheats (eg. durum) must resort to other QTLs, also it has been noted that red wheats vary widely in dormancy. The most dormant white wheats can be as dormant as the least dormant reds: within both colour groups there is a continuous spectrum of dormancy, the scores of red wheats are shifted to the more dormant end of the spectrum, but there is considerable overlap between the two groups. This makes it clear that grain colour is not the sole determinant of dormancy.

Thus it can be seen that further markers to assist in the assessment of PHS resistance and other dormancy-related traits would be beneficial in breeding improved cultivars.

Ideally such markers should be in as close genetic linkage with the QTL as possible, or even better that it have a direct effect on the QT (reducing or even better eliminating the possibility of recombination). Selecting particular alleles which are known to directly exert particular phentoypic effects is termed Direct Allele Selection ('DAS'). Additionally the QTL which is marked should be an important determinant of the QT score. Finally it should also be practicable. Molecular markers, which depend on variation (polymorphisms) in the sequences of bases, are particularly useful in this regard.

The present inventors have now mapped the chromosomal location of the novel taVp1 genes which they isolated.

Briefly, an RFLP polymorphism was identified between two parents of an F2 mapping population, then the alleles present in each individual of the population were determined. These genotypes at the taVp1 locus were then compared with the genotypes of the same individuals at other, genetically linked loci determined previously (Devos et al 1992). Two of the three taVp1 loci were mapped in this way (one on chromosome 3A, one on 3D); the third locus was detected on chromosome 3B by nullisomic analysis.

As with the grain colour genes, taVp1 copies reside at three loci on the long arms of chromosomes 3A, 3B and 3D respectively. The results were compared to the consensus wheat map of Gale et al 1995 [(M. D. Gale, M. D. Atkinson, C. N. Chinoy, R. L. Harcourt, J. Jia, Q. Y. Li & K. M. Devos. 1995. Genetic maps of hexaploid wheat. pp29–40 in: Proceedings 8th International Wheat Genetics Symposium, Eds Z. S. Li & Z. Y. Xin, China Agricultural Scientech Press, Beijing] and homologous taVp1 loci were assigned to the interval between loci Xwg110 and Xpsr549 on the consensus map (see FIG. 7).

Interestingly it was found that the taVp1 genes are linked to the R (colour genes) only at a distance of about 25 centiMorgans. This is clear evidence that taVp1 and R genes are different, so that both marker systems can be used for manipulating dormancy, either in concert or independently. Both markers have direct effects, so loss of effect due to recombination is not a problem. The linkage interval between the two loci on each chromosome is large enough to allow a practicably high frequency of recovery of taVp1/R recombinants should these be required (eg. any existing linkage between a "good" taVp1 allele and a "red" colour allele could realistically be broken for introduction of the taVp1-based dormancy into white wheats).

Apart from the option for breeding dormant white/amber wheats, taVp1 offers advantages over use of the colour marker arising from the availability of clones of wheat alleles. The problems with the colour marker are that it cannot be scored until the grain is ripe, and that no information is available about which of the R genes is present without lengthy and large-scale breeding experiments. Knowledge of the taVp1 DNA, RNA, and/or protein sequences allows the identification of individual alleles present in a sample of tissue, e.g. DNA from the first seedling leaf, or even taken from a seed prior to sowing.

Polymorphisms can be manifest in a number of ways. Structurally they will alter the characteristics of the DNA to bind probes and primers at particular sites, or its properties as a substrate for restriction analysis. Functionally they may affect the quality or quantity of mRNA or protein product which derives from the DNA. Thus, for instance, the presence of absence of a lesion in a promoter or other regulatory sequence may be assessed by determining the level of mRNA production by transcription or the level of polypeptide production by translation from the mRNA. The level of mRNA or protein will be affected not only by its rate of production, but also by its stability and rate of degradation.

Thus the sequence information (nucleic and/or protein product) disclosed herein enables the use of specific amplification, probing or other techniques, to carry out allele identification and hence germplasm classification.

"Nucleic acid sequence" in this context embraces the coding sequences, introns, and promoters of the relevant allele, plus also post-transcriptional modifications of RNA. Thus tests may be carried out on preparations containing genomic DNA, cDNA and/or mRNA. Testing cDNA or mRNA has the advantage of the complexity of the nucleic acid being reduced by the absence of intron sequences, but the possible disadvantage of extra time and effort being required in making the preparations. RNA may be more difficult to manipulate than DNA because of the wide-spread occurrence of RN'ases.

"Protein sequence" in this context covers both the primary structure, plus post-translational protein modifications. Under certain circumstances the total absence of a detectable protein product will be indicative of alterations in the encoded protein sequence.

Generally the methods may make use of biological samples from one or more plants or cells (e.g. in a seed)that are suspected to contain the nucleic acid sequences or polypeptide.

The following method are exemplary only. Those skilled in the art will appreciate that other methods which may be devised without burden on the basis of the information made available by the present inventors also form part of the present invention. For instance a number of methods for determining the presence and identity of polymorphic molecular markers (in the context of biodiversity analysis) are disclosed by Karp et al (1997) Biotechnology 15: 625–628. Such methods may have analagous utility in carrying out the present invention.

1) At the nucleic acid level, identification may involve hybridisation of a suitable specific oligo- or poly-nucleotide probe, such as a fragment of those disclosed herein, or further allelic sequences established using the information disclosed herein. Where the nucleic acid target is double-stranded DNA, hybridisation will generally be preceded by denaturation to produce single-stranded DNA. Such methods include Southern and Northern hybridisations, which can be used both qualitatively or quantitatively (e.g. to assess mRNA level). A screening procedure, chosen from the many available to those skilled in the art, may be used to identify successful hybridisation events and isolate hybridised nucleic acid. For instance, probes may be radioactively, fluorescently or enzymatically labelled.

Preferably the screening is carried out with a variant—or allele-specific probe—this is particular useful for DAS. Such a probe corresponds in sequence to a region of the gene, or its complement, containing a sequence alteration known to be associated with the trait of interest. Under suitably stringent conditions, specific hybridisation of such a probe to test nucleic acid is indicative of the presence of the sequence alteration in the test nucleic acid. For efficient screening purposes, more than one probe may be used on the same test sample.

When screening for particular alleles, the nucleic acid in the sample may initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques Approaches which rely on hybridisation between a probe and test nucleic acid and subsequent detection of a mismatch may be employed. Under appropriate conditions (temperature, pH etc.), an oligonucleotide probe will hybridise with a sequence which is not entirely complementary. The degree of base-pairing between the two molecules will be sufficient for them to anneal despite a mis-match. Various approaches are well known in the art for detecting the presence of a mis-match between two annealing nucleic acid molecules. For instance, RN'ase A cleaves at the site of a mis-match. Cleavage can be detected by electrophoresing test nucleic acid to which the relevant probe or probe has annealed and looking for smaller molecules (i.e. molecules with higher electrophoretic mobility) than the full length probe/test hybrid. Other approaches rely on the use of enzymes such as resolvases or endonucleases. Thus, an oligonucleotide probe that has the sequence of a region of the normal gene (either sense or anti-sense strand) in which polymorphisms associated with the trait of interest are known to occur may be annealed to test nucleic acid and the presence or absence of a mis-match determined. Detection of the presence of a mis-match may indicate the presence in the test nucleic acid of a mutation associated with the trait. On the other hand, an oligonucleotide probe that has the sequence of a region of the gene including a mutation associated with disease resistance may be annealed to test nucleic acid and the presence or absence of a mis-match determined. The presence of a mis-match may indicate that the nucleic acid in the test sample has the normal sequence, or a different mutant or allele sequence. In either case, a battery of probes to different regions of the gene may be employed.

(ii) Allele- or variant- (or even genome-) specific oligonucleotides may similarly be used in PCR to specifically amplify particular sequences if present in a test sample. Assessment of whether a PCR band contains a gene variant may be carried out in a number of ways familiar to those skilled in the art.

The PCR product may for instance be treated in a way that enables one to display the mutation or polymorphism on a denaturing polyacrylamide DNA sequencing gel, with specific bands that are linked to the gene variants being selected. It may also be desirable to analyse DNA fragment size, restriction site variation (e.g. CAPS—cleaved amplified polymorphic sites) and so on. Sequence Tagged Site (STS) Polymerase Chain Reaction (PCR) is rapid, specific, and does not require use of radiosotopes/autoradiography.

Figure 8B:
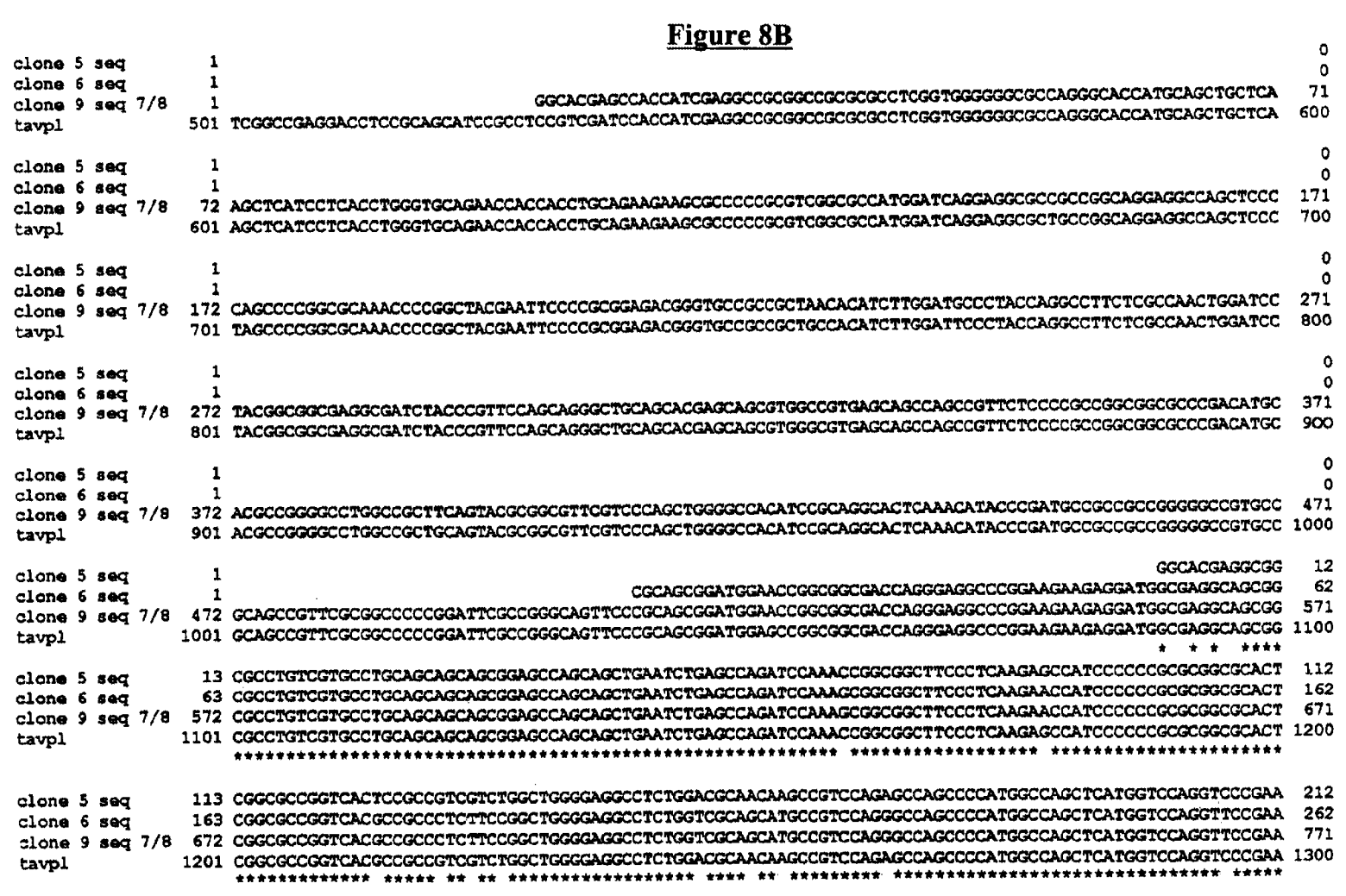

By way of Examples, the following primers could be used to distinguish the certain alleles disclosed in FIGS. 6 and 8. Further primer combinations can be devised without burden by those skilled in the art for new taVP1 alleles if and when they are identified (for instance by use of the materials and methods disclosed herein).

Non specific primer (reverse compliment):

Position 2210/clone 10: CGT CAC ATC TGA CCG ATA GC

Primers to differentiate clones 6+9 from 5+10:

6+9 specific: position 1696: CAT CTC AGG TGT GGA GCA TGC

5+10 specific: position 1691: CGG CAC ATC TCA GAT TTT GGC CC

Primers to differentiate clones 5+6 from 9+10:

5+6 specific: position 1432: GCG GCA GCA GGG TGC GAG G

9+10 specific: position 1432: GCG GCA GCA GGT GCA TGC ATG

Further primers which are specific for the A- B- and D-genomes are discussed in the Examples hereinafter.

(iii) RFLP, hybridized to homologous or heterologous probes based on the sequences disclosed herein. The presence of differences in sequence of nucleic acid molecules may be detected by means of restriction enzyme digestion, such as in a method of DNA fingerprinting where the restriction pattern produced when one or more restriction enzymes (chosen on the basis of the sequences disclosed herein) are used to cut a sample of nucleic acid is compared with the pattern obtained when a sample containing the desired allele or a variant digested with the same enzyme or enzymes. Amplified Fragment Length Polymorphism (AFLP) can be carried out using primers devised on the basis of the sequences disclosed herein. The strength of AFLP is the ability to screen a large number of different marker molecules in a single test. Analysis of the products can be carried out using e.g. by gel electrophoresis, capillary electrophoresis.

(iv) RT-PCR is based on the amplification of RNA, which may be qualitative or quantitative. Essentially this method uses reverse transcriptase to generate a DNA copy of plant mRNA.

(v) Variations in antibody/antigen complexes between plant protein extracts and antibodies targeted to protein epitopes. This is particular useful for distinguishing functional from non-functional proteins (e.g. truncated forms, wherein a particular allele contains a premature stop codon). Thus a sample may be tested for the presence of a binding partner for an antibody (or mixture of antibodies), specific for one or more allelic variants. Binding is assessed by any means commonly known to those skilled in the art. Where a panel of antibodies is used, different reporting labels may be employed for each antibody so that binding of each can be determined.

A specific binding member such as an antibody may be used to isolate and/or purify its binding partner polypeptide from a test sample, to allow for sequence and/or biochemical analysis of the polypeptide to determine whether it has the sequence and/or properties of the wild-type polypeptide or a particular mutant, variant or allele thereof. Amino acid sequence is routine in the art using automated sequencing machines.

Thus the work of the present inventors offers a completely novel approach for manipulating seed dormancy in breeding programmes, exploiting the taVp1 gene sequence which was previously unknown for direct selection of alleles controlling a QT for which currently available techniques are laborious, slow, and inefficient.

Various aspects of the invention will now be discussed in more detail:

In one aspect of the invention there is disclosed a method for assessing the PHS and/or other dormancy related properties of a wheat plant, the method comprising use of the molecular marker taVP1 which occurs in the interval between loci Xwg110 and Xpsr549 on the wheat group 3 consensus map.

In a further aspect of the invention these is disclosed of producing a cultivar comprising the steps of selecting a parent line having desired PHS and/or other dormancy related properties, breeding with that line, and selecting progeny on the basis of the molecular marker taVP1 described above.

Preferably the selection of the parent line(s) and/or progeny is done on the basis of specific superior alleles (i.e. DAS). This allows precise manipulation of variation of PHS via selection of progenies with appropriate, desired functional activity of characterised alleles. Thus PHS may be improved by selection for high levels of expression of fully-functional alleles, firstly by selecting parents carrying desirable genomic copies of taVp1 gene(s), then by selecting progeny which express these alleles strongly at appropriate stages of seed development and maturation.

The assessment can be on the basis of analysing taVP1 DNA, RNA or protein as described above, and then correlating the result of the analysis with the expected PHS phenotype.

Parent plants possessing favoured alleles may be obtained from within an existing variety genepool, or prepared mutants from within an elite genepool.

Alternatively desirable alleles or may also be detected and transferred from one or more of the many wild or cultivated relatives of the plant, for which established methods are available for the introduction of "alien" variation into the plant genome. The correlation of the PHS trait with the afVP1 sequence greatly facilitates the identification and selection of desirable alleles in exotic germplasm. This is especially useful for species in which genetic variation in cultivated germplasm is limited (e.g. wheat *T aestivum*—see Chao et al (1989) Theor Appl Genet 88:717–721).

In the past, using traditional methods, problems with using exotic germplasm have included the low frequency of desirable alleles, and difficulties with linkage drag and polygenic inheritance. Such problems will be minimised by use of the present invention.

Lines may be produced by breeding from selected lines in accordance with standard techniques well known to those skilled in the art.

Clearly the PHS phenotype can be manipulated up or down; for applications in which dormancy is undesirable, e.g. malting, the same information and techniques could be employed to select in the reverse direction, i.e. to fix defective or poorly expressed copies of taVP1.

The demonstration by the present inventors that the afVP1 and seed colour gene alleles are linked but separate demonstrates that both marker systems can be used for manipulating dormancy, either in concert or independently. Thus methods of selection based on taVP1 alone (e.g. in white/ amber grained wheats) or both taVP1 and red grain colour (e.g. in red wheats) also form part of the present invention.

Methods in which the taVP1 allele in particular plant or line is assessed and the result of the assessment is correlated directly with expected PHS phenotype, e.g. for the purposes of timing harvest, form a further part of the invention.

The taVP1 assessment may also be used to assess pedigree or phylogenetic origin if desired.

Nucleic acid-based determination of the identity of a particular taVP1 allele (e.g. as in the methods described above) may be combined with determination of the genotype of the flanking linked genomic DNA and other unlinked genomic DNA using established sets of markers such as RFLPs, microsatellites or SSRS, AFLPS, RAPDs etc. This enables the researcher or plant breeder to select for not only the presence of the desirable taVP1 allele but also for individual plant or families of plants which have the most desirable combinations of linked and unlinked genetic background. Such recombinations of desirable material may occur only rarely within a given segregating breeding population or backcross progeny. Direct assay of the taVP1 locus as afforded by the present invention allows the researcher to make a stepwise approach to fixing (making homozygous) the desired combination of flanking markers and taVP1 alleles, by first identifying individuals fixed for one flanking marker and then identifying progeny fixed on the other side of the locus all the time knowing with confidence that the desirable taVP1 allele is still present.

The sequence information provided herein also allows the design of diagnostic tests and kits for determination of the presence of particular taVP1 and afVP1 alleles, in any given plant, cultivar, variety, population, landrace, part of a family or other selection in a breeding programme or other such genotype. A diagnostic test may be based on determination of the presence or absence of a particular allele by means of nucleic acid or polypeptide determination.

Plants which are generated (or assessed and or approved) using the taVP1-allele assessment methods of the present invention form a further aspect of the invention. Plants in this context embraces cultivars, and seeds, microspores, protoplasts, cotyledons, zygotes (ovules, pollen) and vegetative parts derived therefrom. It further embraces any clone of such a plant, selfed or hybrid progeny and descendants, and any part of any of these, such as cuttings and seed. Products made from such plants e.g. milled or malted grains, flour etc. are also embraced by the invention.

The invention will now be further illustrated with reference to the following non-limiting Figures and Examples. Other embodiments falling within the scope of the invention will occur to those skilled in the art in the light of these.

SEQUENCE ID NOS

Seq ID No 1: (see FIG. 4(*a*)) "afVP1" CDNA sequence.
Seq ID No 2: (See FIG. 10(*a*)): "taVP1" CDNA sequence.

FIGURES

FIGS. 1A–1C. Germination behaviour of seed from inbred lines of Avena fatua.

FIGS. 2A–2D. Northern blot analysis of gene expression patterns of imbibed seed from inbred lines subjected to different environmental conditions. a. Freshly harvested seed, b. Freshly harvested and after-ripened seed, c. Seed stored at 4° C. or 24° C. for one year, d. Seed following induction of secondary dormancy (Treated) or Untreated. In each case RNA was extracted from seed following 48 h imbibition. RNA loadings for each sample were 3 µg and 0.5 µg polyA containing RNA per lane. % germination (G%) of seed at the time of RNA extraction is indicated.

Figure 3:
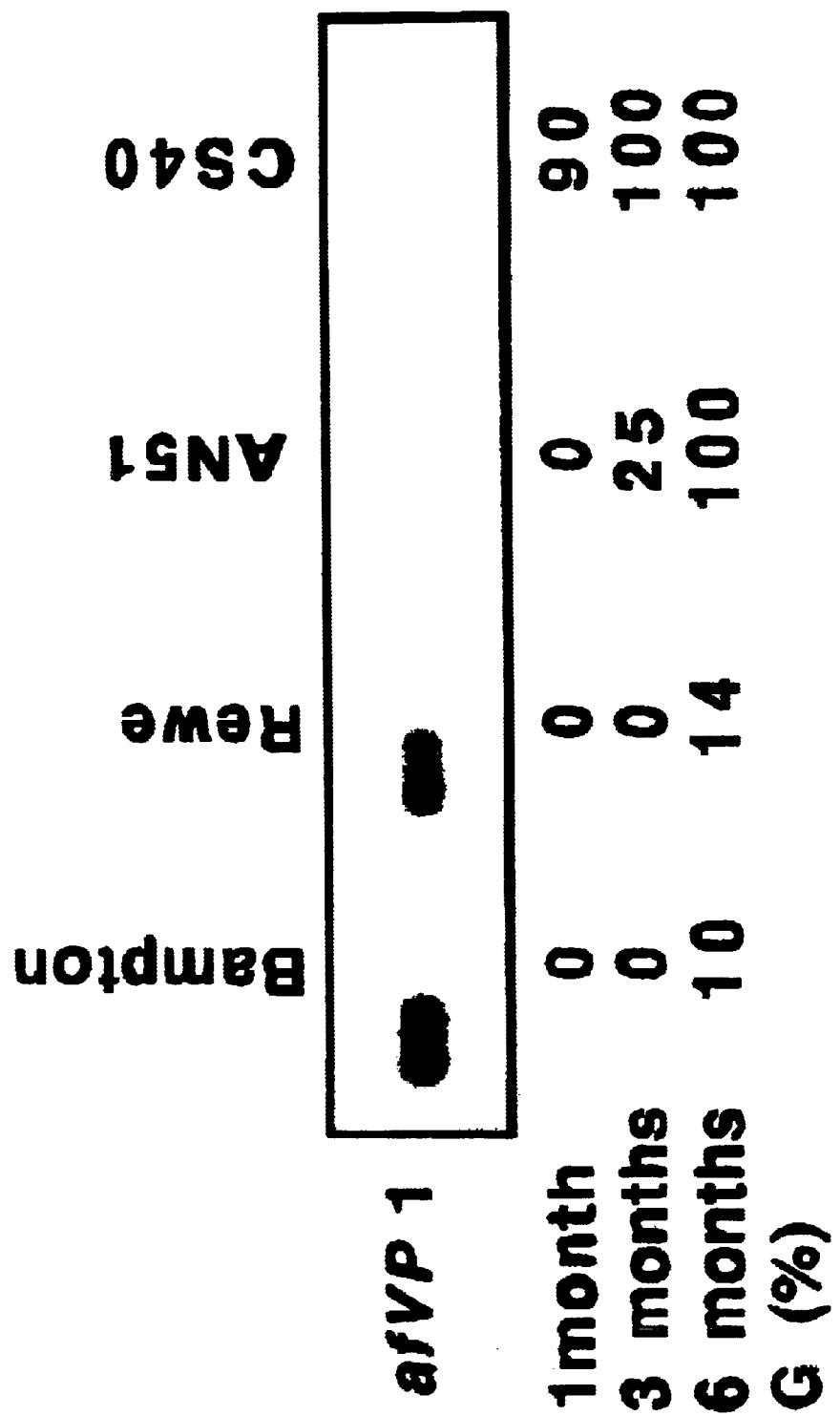

FIG. 3. Northern blot analysis shows afVP 1 expression in the dry seed is positively correlated to length of after-ripening time required to break dormancy. Germination percentages [G(%)] are shown for four inbred lines 1, 3 and 6 months after harvest. RNA loadings for each sample were 3 μg and 0.5 μg polyA containing RNA per lane.

FIG. 4(a): Seq ID No 1, "afVP1" cDNA sequence.

Figure 4B:
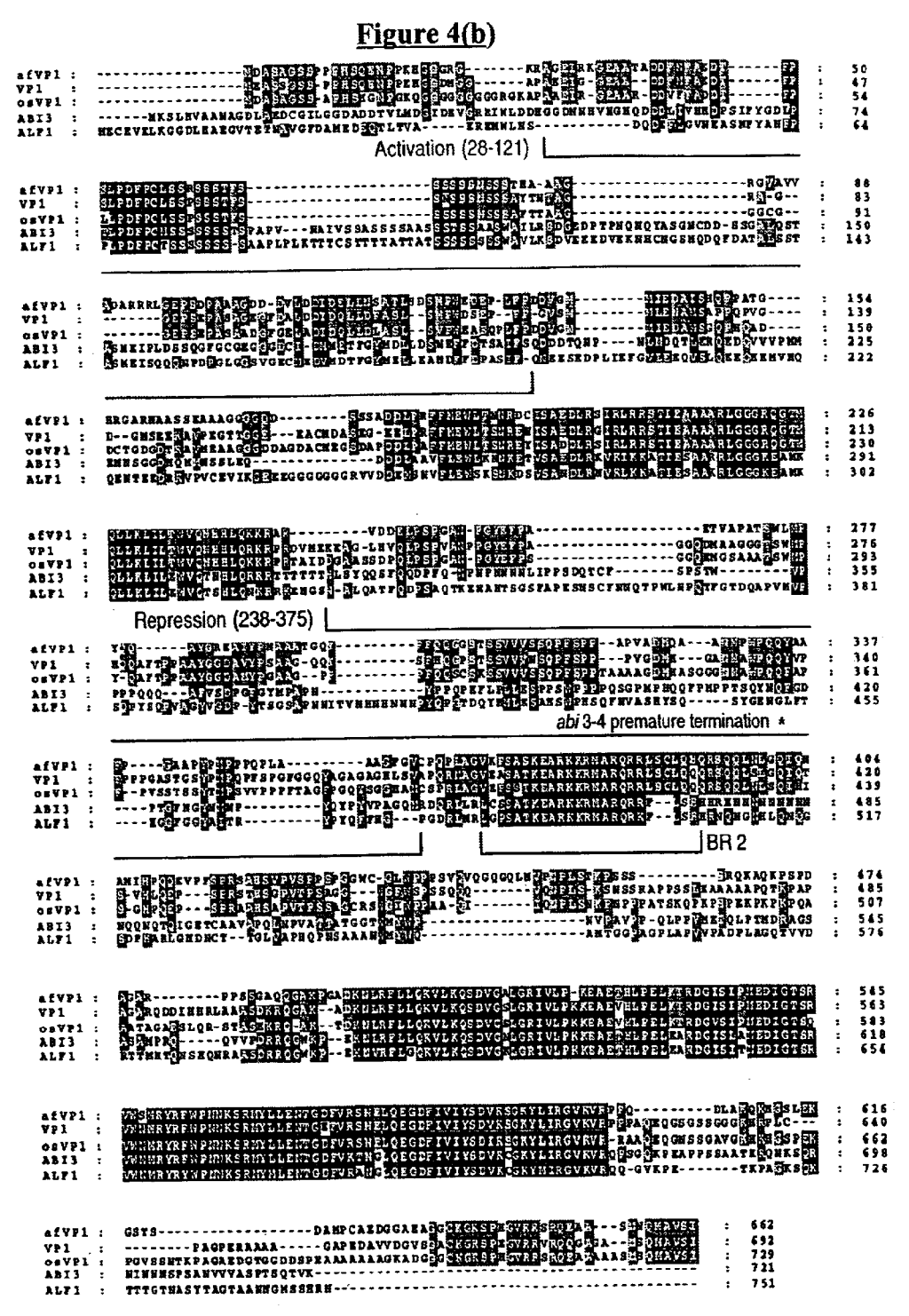

FIG. 4(b): Comparison of afVP 1 predicted protein sequence with other VP 1 like transcription factors.

Comparison of the protein sequences from Avena fatua (afVP 1), maize (VP 1), rice (osVP 1), bean (ALF 1), Arabidopsis (ABI 3).

Figure 5:
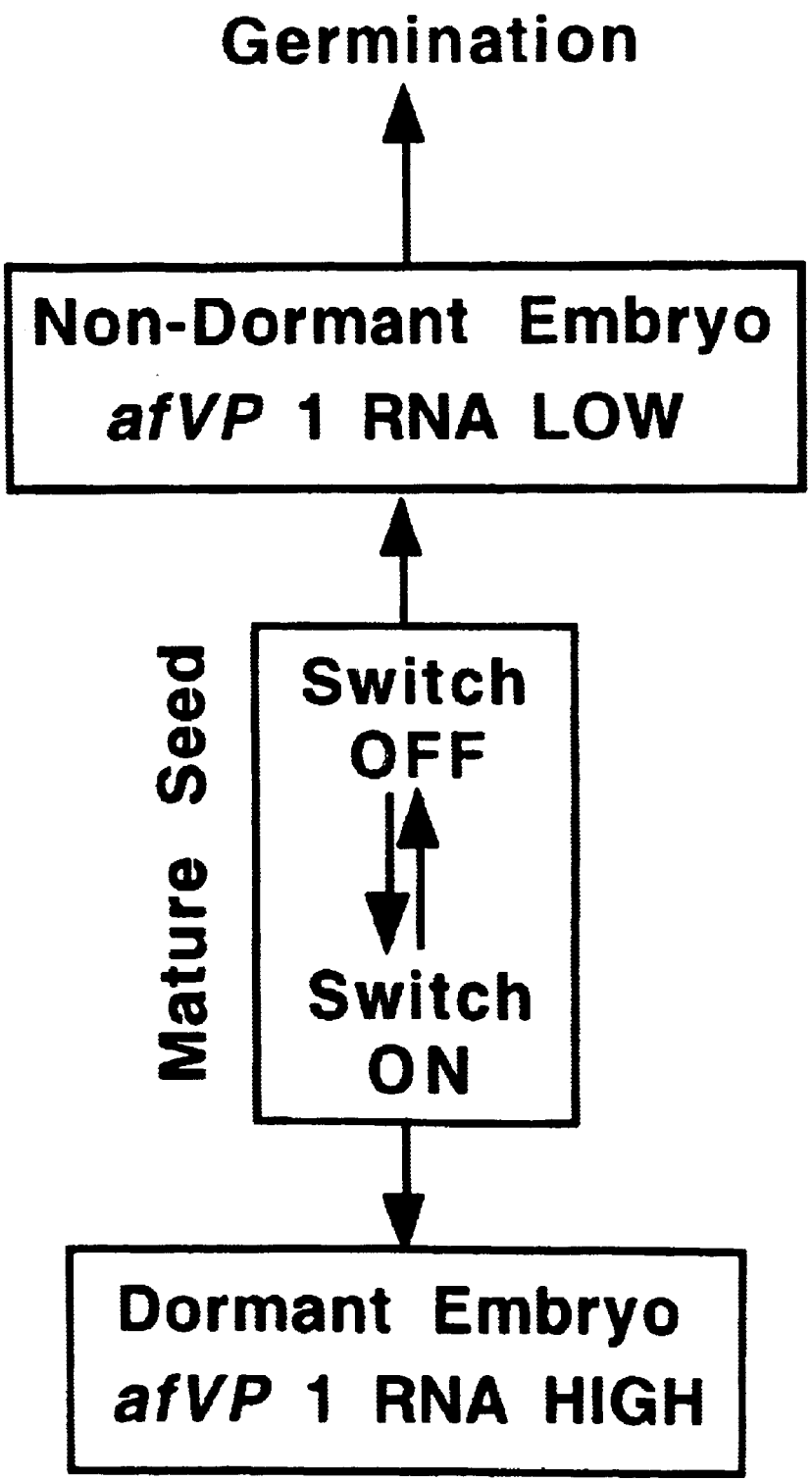

FIG. 5. Model for the control of embryo dormancy and afVP 1 RNA levels by a switch that shows properties of reversibility.

FIGS. 6A–6B. taVP1 allele (clone 4).

Figure 7:
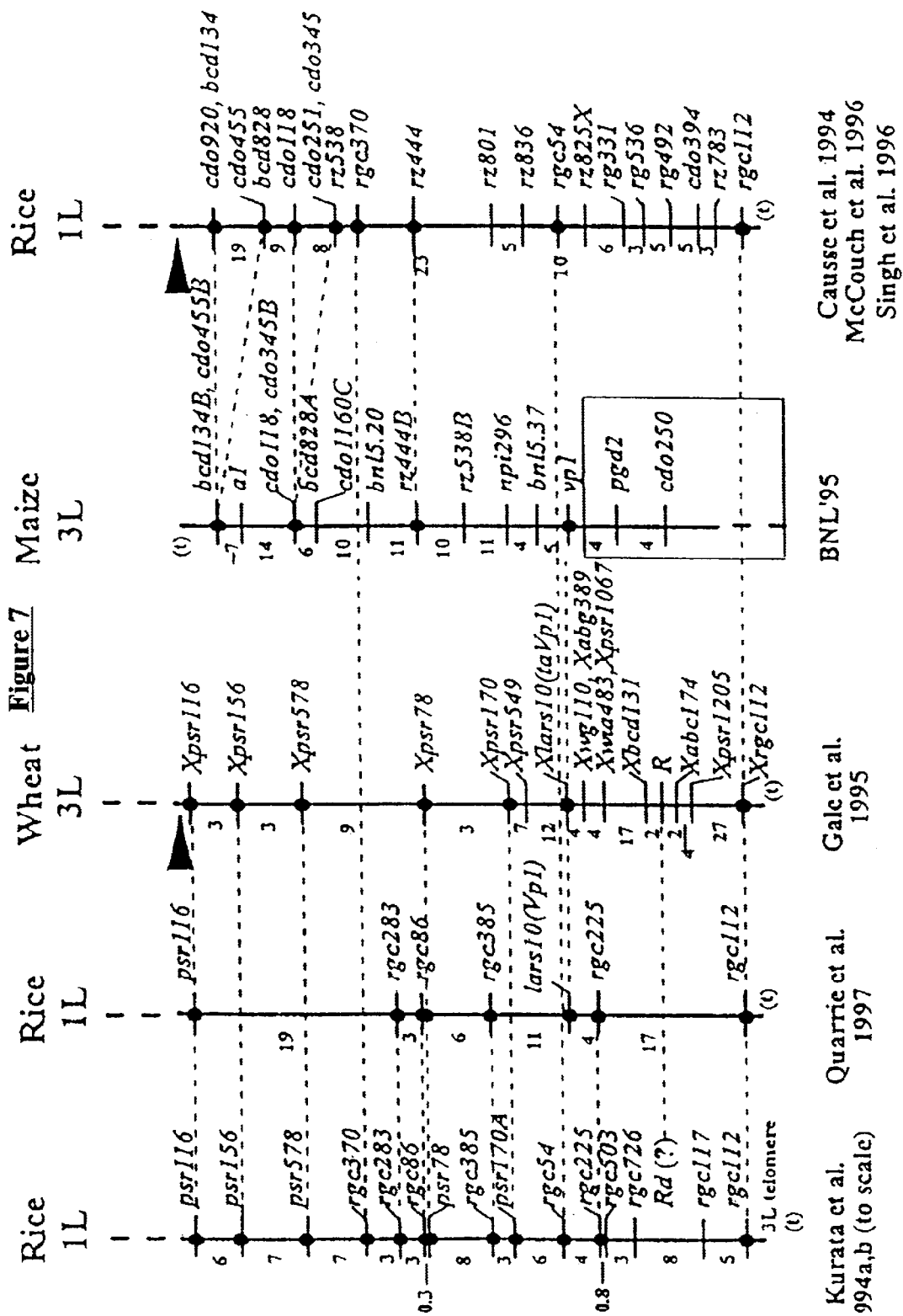

FIG. 7: Locations of orthologues in wheat (taVp1), rice (osVP1) and maize (VP1). From left to right the rice maps are based on Kurata et al (1994a,b) and Quarrie et al (1997), wheat on the concensus map of Gale et al (1995), maize (inverted relative to wheat and rice) on the BNL'95 (Anon, 1995) and rice on the map of Causse et al (1994) with additional markers mapped by McCough et al (1996) and the centromeres positioned proximal to cdo920 as demonstrated by Singh et al (1996). Homeologous marker loci present on two or more maps are joined by dotted lines. Arrows indicate centromeres. Figures to the left of each map denote intervals in centiMorgans.

FIGS. 8A–8D. Clone 10, representing the taVP1 cDNA sequence. Also shown are further taVP1 alleles (clones 5, 6 and 9) which have been sequenced to various degrees.

Figure 9:
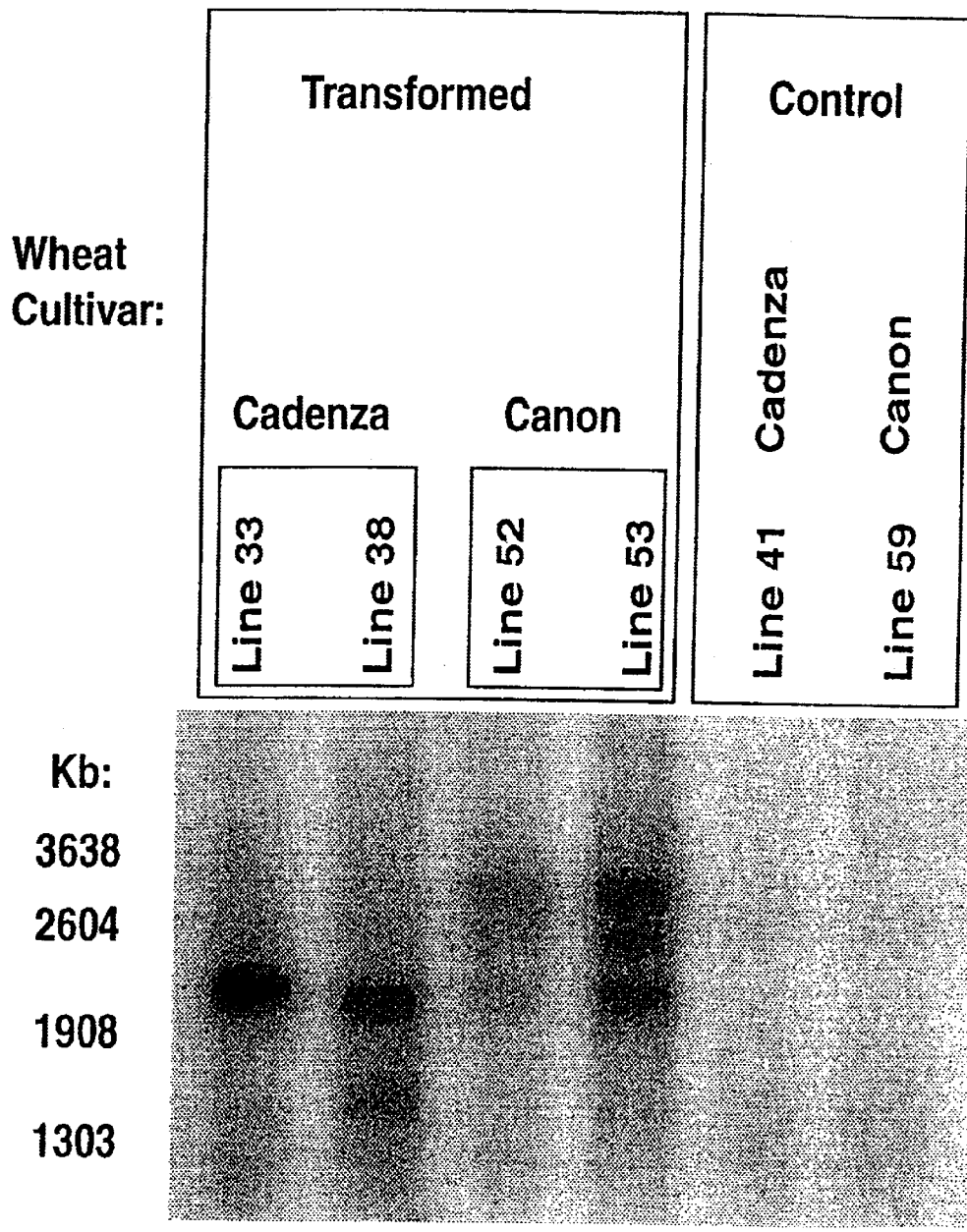

FIG. 9. Northern blot analysis of transgenic wheat plants containing afVP1 sequence.

FIG. 10(a): Seq ID No 2, "taVP1" cDNA (clone 10)

FIG. 10(b): clone 2

FIG. 10(c): clone 3

FIG. 10(d): clone 4

FIG. 10(e): clone 5

FIG. 10(f): clone 6

FIG. 10(g): clone 9

Figure 11:
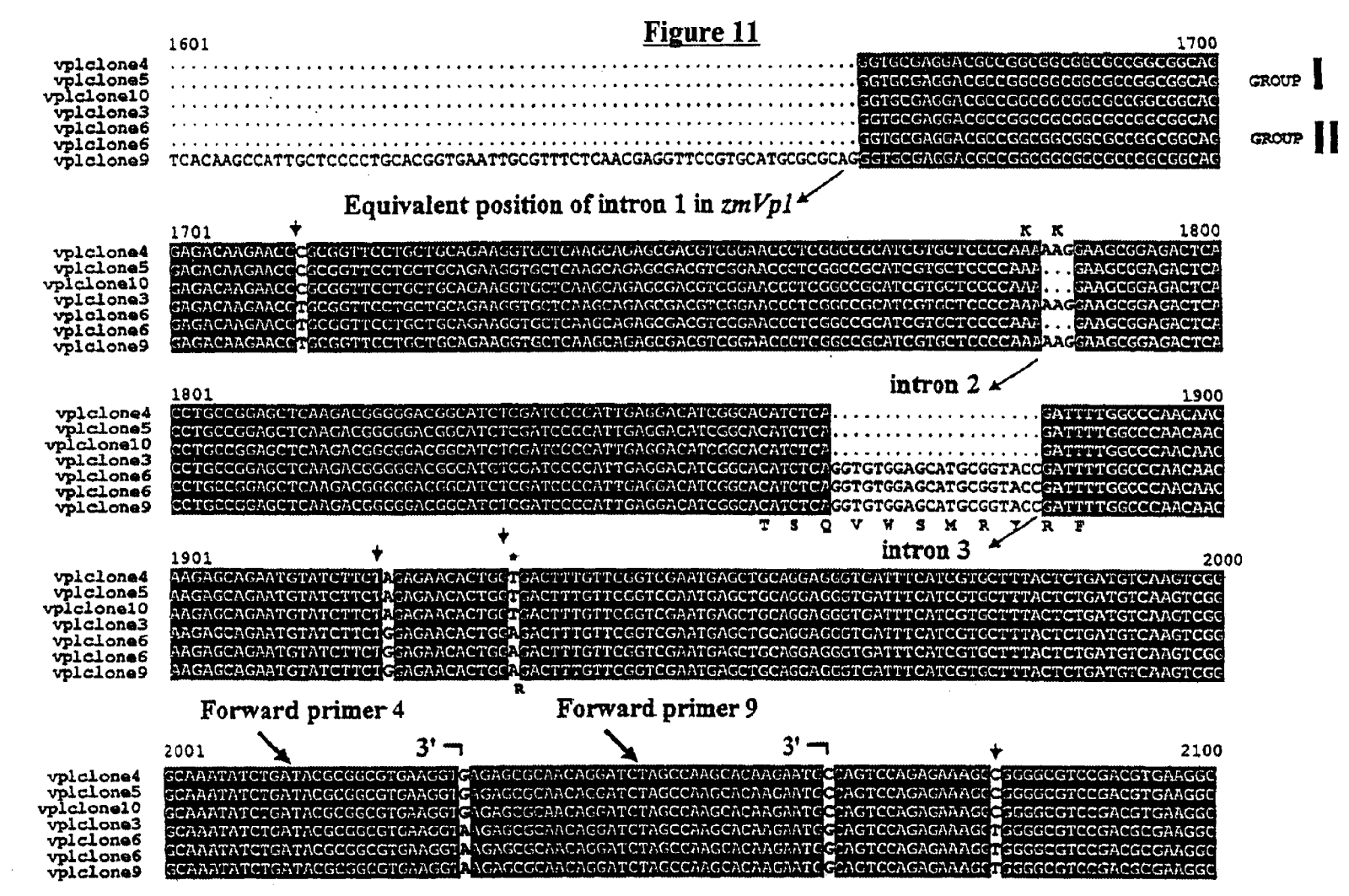

FIG. 11. Alignment of sections of six taVP1 clones demonstrating that they fall into two groups (group I=4, 5, 10; group II=3, 6, 9).

Figure 12:
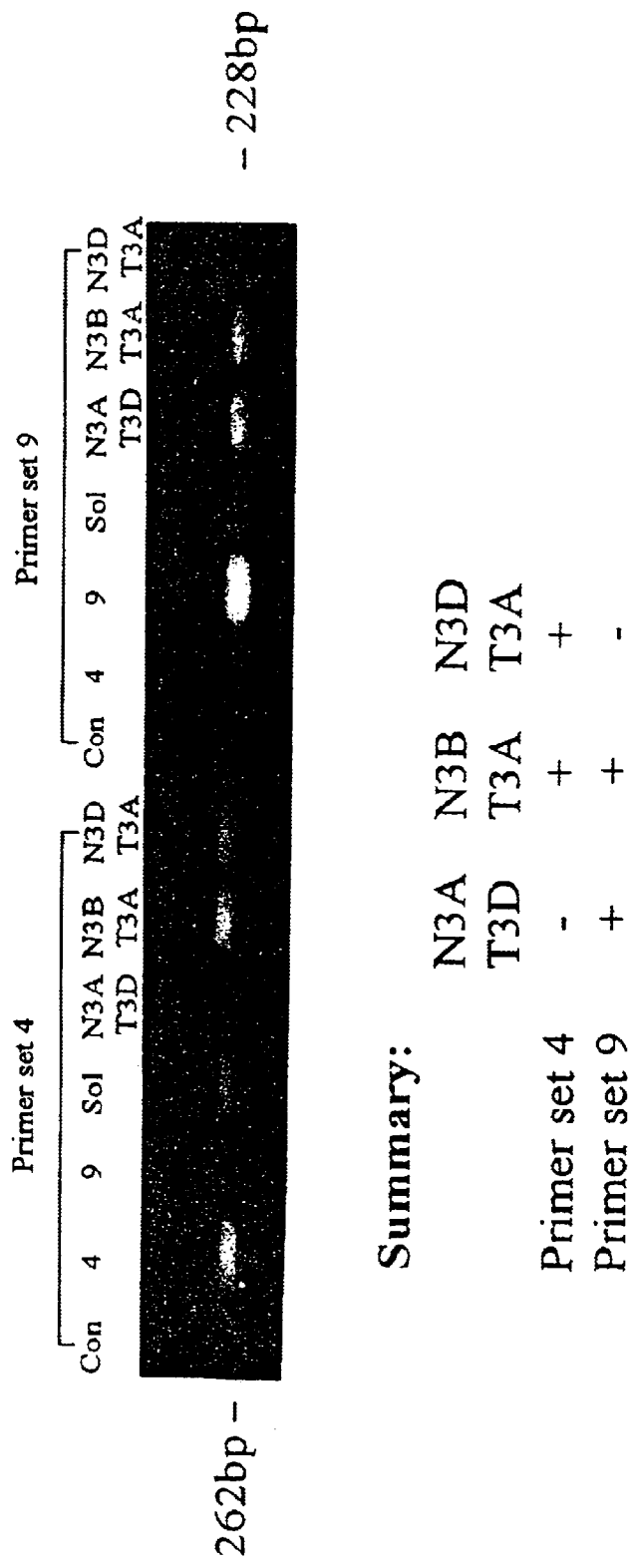

FIG. 12. Results of PCR using templates specific for the two groups. The results using primer set 4 suggest that clone 4 is found on chromosome 3A. The results using primer set 9 suggest that clone 9 is found on chromosome 3D.

EXAMPLES

Example 1

Analysis of Role of afVP1 in Dormancy and After-ripening

Plant Material;

A. fatua inbred lines CS40, AN127, AN51 SH99 used in this study were obtained from Professor G Simpson (Univ. Of Saskatchewan, Canada). The lines were derived from single seeds selfed for six generations and grown in controlled environment rooms (Jana et al. 1988). Inbred line Bampton has been described previously (Hooley et al. 1991, Rushton et al. 1992) derived from single seed selfed for at least 10 generations, inbred line Rewe (Peters 1991) was derived from single seed selfed for 3 generations. Mature seeds were obtained from plants grown outdoors during the summer each year. Air dry seeds were stored in the dark in constant environment chambers at 15° C. unless otherwise stated. After-ripening and dormancy levels were monitored every three months by a germination assay.

Germination Assays;

Germination assays were conducted at 22° C. in the dark. Seeds were first de-husked, surface-sterilized with 10% (v/v) Parozone (Jeyes Ltd, Norfolk, UK) for 10 minutes, washed with sterile water, and then incubated embryo-side up on moist sterile glass fibre paper for the times indicated in individual figures.

Results:

Six inbred lines of A. fatua were used to study the relationship between genetics and environment in the control of embryo dormancy. Dormancy/germination potential of seeds from these lines was assessed over a twelve month period from harvest, following storage at 24° C. The inbred line CS40 showed an extremely non-dormant phenotype. Dry seeds stored at 24° C. after-ripened within 1 month and embryos germinated within 48 h of imbibition (FIG. 1a). Lines AN51 and SH99 showed higher levels of primary dormancy than CS40, although this dormancy rapidly diminished with after-ripening. Line AN127, Rewe and Bampton showed a greater degree of dormancy. Embryos from these lines after-ripened slowly, taking between 6 months to 1 year to lose dormancy when stored at 24° C. During the period of after-ripening the time taken between initiation of imbibition and germination was much longer in lines showing dormancy, than in CS40. However this lag time decreased as after-ripening time increased and dormancy was lost.

Primary dormancy in Bampton was high (FIG. 1a), but after 3 years storage at 24° C. dormancy was lost (indicating that after-ripening was completed). However, embryos from seeds stored at 4° C. for the same period were still completely dormant (FIG. 1b), showing that temperature is an important determinant of the time required for after-ripening. Dormancy of Bampton seeds stored at 4° C. could only be broken following imbibition at 24° C. by a combination of GA treatment and mechanical rupture (data not shown).

The effects of conditions that induce secondary dormancy were investigated in three lines, CS40 (non-dormant, ND), AN127 and Bampton (both dormant, D) following complete after-ripening of the embryos (FIG. 1c). Secondary dormancy was induced by immersing seeds in de-gassed water for 70 h at 24° C. in the dark. Embryos were then tested for dormancy potential in the normal germination assay. Final germination levels of seeds of the line CS40 were unaffected by the inductive treatment, although germination was slightly delayed. However seeds of AN127 and Bampton were highly susceptible to the treatment, showing reversion to a dormant phenotype following imbibition.

Extraction and Analysis of RNA;

Poly-A containing RNA was extracted from seeds as described previously (Grierson 1992). RNA was size fractionated on 1.5% agarose MOPS-formaldehyde gels and transferred to a nitrocellulose membrane (Sambrook et al. 1989). Specific mRNAs were detected by hybridisation to maize VP1 cDNA clones from McCarty et al (1989) The Plant Cell 1, 523–532, labelled with $\alpha$-$^{32}$P[dCTP] by random-priming using the Stratagene Prime-it II kit according to the manufacturers recommendations. Hybridisation conditions were 50% formamide, 6×SSPE, 5×Denhardts, 0.5% SDS, 100 μg/ml denatured calf thymus DNA, at 42° C. for 16 h. Filters were washed once for 10 min at room temperature in 1×SSPE, 0.1% SDS, once for 30 min at room temperature in 1×SSPE, 0.1% SDS, and finally 30 min at 55° C. in 1×SSPE, 0.1% SDS (Sambrook et al. 1989). Prior to autoradiography X-ray film was pre-flashed to ensure detected signals were within the linear range of detection for the film.

Results:

We analysed gene expression patterns in seeds to determine whether the expression of specific genes was regulated, by genetic background and environment, in the same way as dormancy/germination phenotypes in the inbred lines of *A. fatua*. Two marker genes were chosen that have previously been linked to particular developmental states of embryos (AMY 2/1 and Em) (table 1) Other genes analysed were af 10 (expressed throughout development), and the *A. fatua* homologue of the maize transcription factor gene VP 1 (afVP 1).

TABLE 1

| Gene Name: | Function: | Developmental Expression: |
|---|---|---|
| α-amylase (AMY 2/1) (*Avena fatua*)[1] | Starch hydrolysis | Germination Specific: Expression is repressed by VP 1 in maize.[5] |
| Em (wheat)[2] | | Embryo Maturation: Expression is activated by VP 1 in maize.[6] |
| af 10 (*Avena fatua*)[3] | ? | General. |
| afVP 1 (*Avena fatua*) | Embryo Transcription Factor[4] | Embryo Maturation in maize.[4] |

Function and expression patterns of genes used in this study.
[1]Hooley et al. 1991,
[2]Williamson et al. 1985,
[3]Jones 1996,
[4]McCarty et al. 1991,
[5]Hoecker et al. 1995,
[6]Vasil et al. 1995.

We were particularly interested in analysing the expression of the *A. fatua* VP 1 homologue under the conditions described. The VP 1 transcription factor has previously been shown to control embryo maturation in maize, and recent evidence suggests that ABI 3 represses post-germination developmental processes during embryogenesis (Nambara et al. 1995). Our initial hypothesis was that the *A. fatua* homologue of VP 1 (afVP 1) may regulate processes involved with embryo dormancy following imbibition of the mature seed, by maintaining embryos in the dormant state and inhibiting the dormancy/germination transition. If this was true, then expression of the *A. fatua* homologue of VP 1 should be linked to the dormant phenotype in imbibed mature seed, and not be limited to embryogenesis. We cloned the *A. fatua* homologue of VP 1 (afVP 1, see section below) and used this cDNA to study expression characteristics of the corresponding RNA. Experiments analyzing the expression of other genes in this study used homologous probes (AMY 2/1, af 10) and a heterologous probe from wheat (Em). Expression of Em related RNAs was studied because this gene has been shown to be transcriptionally activated by VP 1 in maize during embryogenesis (McCarty et al. 1991, Vasil et al. 1995). Transcription of the α-amylase gene AMY 6–4 has been shown to be specifically repressed by VP 1 in developing barley seeds, and this gene is a classic marker for germination (Hoecker et al. 1995).

PolyA-containing RNA was extracted from seeds and analysed by northern blot using radioactively labelled DNA probes. Initially we investigated the expression of all the genes in freshly harvested seeds left to imbibe for 48 h (FIG. 2*a*). Differences in primary dormancy due to genotype were most pronounced at this time (FIG. 1*a*). AMY-related gene expression was correlated with lines showing germination (ANS1 and CS40). The af 10 RNA was expressed in all inbred lines, regardless of phenotype (as were polyubiquitin-related RNAs, data not shown). Expression levels of afEm and afVP 1 RNAs were all increased in lines showing a dormant phenotype (AN51, AN127, SH99, Bampton and Rewe). Next we investigated expression levels of these RNAs in selected lines that had been allowed to after-ripen (FIG. 2*b*). There was no difference in expression of all the different transcripts between fresh and after-ripened seed of the non dormant line CS40 (ND). There was an increase in expression of AMY expression in after-ripened AN51 and Bampton (although the increase was much less in Bampton), and a large decrease in expression of the afVP 1 and afEm RNA's in after-ripened imbibed seed compared to fresh dormant seed.

The influence of temperature of dry seed storage on gene expression was analysed using seeds from the dormant inbred line Bampton (FIG. 2*c*). Seed was stored for 1 year at either 24° C. or 4° C., and then imbibed for 48 h before RNA extraction. Levels of AMY-related RNA were high in imbibed seeds that had been stored at 24° C. and fully after-ripened, but not in imbibed seed stored at 4° C. that were still dormant. Levels of RNA corresponding to the afVP 1 and afEm genes were higher in imbibed seeds that had been stored at 4° C. and were still dormant.

We analysed the influence of induction of secondary dormancy on gene expression using the lines CS40 and Bampton (FIG. 2*d*). The inductive conditions had little effect on the final CS40 seed germination phenotype (FIG. 1*c*) or on the expression patterns of RNAs analysed in this inbred line (FIG. 2*c*). Embryos showed high levels of germination, and high levels of AMY RNA, but low levels of afEm and afVP 1 RNAs. The same environmental conditions induced secondary dormancy in Bampton seeds (FIG. 1*c*), and associated changes in gene expression. AMY RNA was detected at very low levels in treated seeds, whereas afVP 1 and afEm RNAs were present at high levels in treated embryos (D) compared to untreated (ND) embryos.

We analysed whether the depth of dormancy (ie. the length of after-ripening time required to break dormancy) shown by seeds from the inbred lines was correlated to the expression levels of afVP 1 in the dry seed. Poly(A)-containing RNA was extracted from dry seeds of lines CS40, AN51 (both show very short after-ripening times, FIG. 1), Bampton and Rewe (both have long after-ripening requirements), and expression of afVP 1 RNA was analysed by northern blot (FIG. 3). RNA corresponding to afVP 1 was expressed at similar high levels in the seeds of lines Bampton and Rewe, whereas expression of afVP 1 RNA was much lower in seeds from lines CS40 and ANS1. Comparison of the after-ripening period and levels of afVP 1 expression (FIG. 3) demonstrated a positive correlation between the length of time required for after-ripening to occur and the level of expression of afVP 1 RNA in the dry seed.

Discussion

We have shown that genetic background and environment interact in the dry seed to control the subsequent developmental pathway, and gene expression programmes, of the embryo following imbibition. This study showed a strong correlation between the dormant phenotype and expression of afVP 1 RNA in both the dry and imbibed seed. The results obtained suggest two new features of the biology of VP 1/ABI 3-related transcription factor family. Firstly, the results indicate that a switching mechanism in the dry seed results in differential expression of afVP 1 following imbibition. This mechanism results in increased expression of afVP 1 in dormant imbibed embryos from mature seeds, and reduced expression during the initiation of germination. Secondly, the results suggest a new function for VP 1 related transcription factors during dormancy in addition to already described functions in embryogenesis, as regulators of post-imbibition dormancy-related processes.

The different inbred lines used in this study showed different degrees of primary dormancy and rates of after-ripening. In all cases, degree of dormancy and rate of after-ripening were positively correlated, indicating that the two processes were related. Temperature of storage also influenced after-ripening, a low temperature increasing the after-ripening period. This suggests that temperature effects the mechanism regulating after-ripening. Dormancy could be re-introduced (secondary dormancy) into embryos by a specific treatment, but only to embryos of those lines that originally showed primary dormancy. These results show that dormancy can only be is re-introduced into embryos that have the capacity for primary dormancy, ie. those that have a genotype conferring dormancy. The results also suggest that primary and secondary embryo dormancy are both controlled by the same genetic loci responsible for the maintenance of primary dormancy. Those embryos showing primary dormancy also had the capacity for secondary dormancy. These results suggest that the switch mechanism operating in mature seeds may show some features of reversibility (FIG. 5). This model predicts that the switch determines the degree of primary dormancy, but can also be reactivated (reversed) by environmental conditions to induce secondary dormancy following loss of primary dormancy. In mature seeds, the switch controls the developmental decision of whether the seed will become dormant or germinate on imbibition, and of gene expression programmes in imbibed embryos (see below). A bistable switch has previously been postulated to control dormancy (Trewavas 1987) by interactions between kinases and phosphatases. The product of the ABI 1 gene from Arabidopsis (mutant abi 1 effects include disruption of dormancy) is a calcium-modulated phosphatase and could possibly fulfil this role (Leung et al. 1994).

Our analysis of gene expression following imbibition of seeds shows that dormant and germinating embryos carry out very different expression programmes. Other studies have shown that several genes of unknown function are up regulated in dormant embryos (Johnson et al. 1995, Li and Foley 1995). We have shown that expression of the afVP 1 gene was positively correlated to the dormant phenotype under all the conditions we tested, in both the dry and imbibed seed. In addition, afEm RNA showed a similar pattern of regulation. These results suggest therefore that these RNA's are regulated by developmental decisions that occur in the mature seed (FIG. 5). In particular it is noteworthy that afVP 1 expression in the dry seed was shown to be correlated with the depth of dormancy shown by inbred lines. That is, those lines that take longest to after-ripen contained the most afVP 1 RNA the dry seed, whereas those lines that after-ripen very quickly contained very low levels (FIG. 3). Thus the amount of afVP 1 RNA in the seed at the very onset of imbibition may determine to some degree the dormancy/germination fate of the seed, and this RNA is laid down in the seed during the final stages of embryo maturation.

The observation of positive correlation between afVP 1 expression in the dry seed and after-ripening requirement shows that this gene could be used as a molecular marker for dormancy potential/after-ripening time.

High levels of expression in the dry seed would indicate a higher degree of dormancy/ longer after-ripening requirement. The relationship between afVP 1 expression in dry and imbibed seed, and embryo genotype indicates that this-gene may represent previously described *A. fatua* loci L1 or L2 (Jana et al. 1979, Jana et al. 1988), which influence the degree of dormancy.

Previous work has demonstrated that VP 1/ABI 3 act in the maturation stage of embryogenesis (Hattori et al., 1992, McCarty et al. 1991, Nambara et al. 1995, Parcy et al. 1994), and do not function following seed desiccation, (for example ABI 3 RNA expression is reduced rapidly on imbibition of mature Arabidopsis seed [Parcy et al. 1994]). The up-regulation of the afVP 1 RNA in dormant *A. fatua* embryos suggests that the encoded protein may play a role in maintaining the dormant state. Our results suggest that one function for afVP 1 in dormant embryos could be the transcriptional activation of the *A. fatua* Em gene. Maize VP 1 has previously been shown to regulate Em during embryo maturation by activation of Em transcription through specific cis-elements (Vasil et al. 1995), and afVP 1 could function in a similar way. It would be interesting to analyse the relationship between genes regulated by afVP 1 in dormant embryos and during embryogenesis to define if this transcription factor functions in a similar or different way in these two different developmental states. Recent results show that ABI 3 is also involved in repressing post-germination developmental processes during embryogenesis (Nambara et al. 1995). Another function of afVP 1 in imbibed dormant seeds may therefore be the inhibition of germination-related processes (and germination-related gene expression such as $\alpha$-amylase).

Example 2

Isolation of afVp1—cDNA Library Construction and Manipulation of Nucleic Acids cDNA library construction was carried out as previously described (Holdsworth et al. 1992) using poly-A containing RNA from mature embryos of inbred line Bampton. Oligo dT primed cDNA was ligated into the vector $\lambda$-MOSSlox (Palazzolo et al. 1990), and screened according to the manufacturers recommendations (Amersham International plc, UK). Five-prime RACE (rapid amplification of CDNA ends) was carried out using the Marathon cDNA amplification kit (Clontech Laboratories Inc, CA, USA). RACE-PCR was primed with a synthetic oligonucleotide corresponding to positions 878–898 of the full-length afVP 1 cDNA. Ligation and sub-cloning of DNA fragments were carried out as described in Sambrook et al. (1989). Sequencing of cloned RACE-PCR amplification products was performed manually by the dideoxy chain termination method (Sanger et al. 1977). Sequencing of $\lambda$MOSSlox subclones was done using a DuPont Genesis 2000 Automated Sequencer (Univ. of Bristol Molecular Recognition Centre, UK). DNA sequence analysis was carried out using the MacVector™ and AssemblyLine™ programmes (Oxford Molecular Group plc, UK) and GCG8 (University of Wisconsin Genetics Computer Group version 8 [Genetics Computer Group 1994]).

Results

The DNA sequence corresponding to the afVP 1 RNA was obtained by a combination of cDNA cloning and 5'RACE (rapid amplification of cDNA ends). The combined length predicted from these sequences is 2338 bases for the full-length RNA, which is similar to the size observed in Northern Blot analysis of afVP 1.

The predicted protein is 662 amino acids long, smaller than all other VP 1/ ABI 3 homologues. The protein sequence of afVP 1 derived from the cDNA was compared to predicted protein sequences of homologues from maize (VP 1, McCarty et al. 1991), rice (osVP 1, Hattori et al. 1994), Arabidopsis (ABI 3, Giruadat et al. 1992) and Phaseolus vulgaris (ALF 1, Bob et al. 1995) using the GCG8 programme Pileup (Genetics Computer Group 1994).

Analysis of the predicted protein sequence of afVP 1 shows that it is highly similar to other VP 1/ABI 3-related proteins, particularly in the four regions previously shown to be highly conserved. These regions may be involved in protein structure or be conserved functional domains. The region between amino acids 386 and 407, BR2 (Basic Region 2), in VP 1 has previously been shown to interact in-vitro with several different classes of transcription factor, including EmBP 1, previously shown to be involved in the regulation of the Em gene (Hill et al. 1996). The predicted protein sequence of afVP 1 shows high homology with VP 1/ABI 3 in this region, suggesting a similar functional role in A. fatua. The in-vivo importance of the BR2 region for the function of this transcription factor family is indicated by the observation that BR 2 occurs at position 439–475 in ABI 3, and the severe allele abi 3–4 contains a mutation that converts Gln 417 to a premature stop codon (Giraudat et al. 1992, FIG. 3). In addition, the fourth (and largest) highly conserved region lies downstream of the abi 3–4 premature stop codon, suggesting an important role for this region also, although no function has yet been proposed for this region. Other regions of the protein, including those shown in maize to regulate Em transcription and AMY repression show low homology, and may be responsible for different functions of the proteins or differences in efficiency of interaction with other proteins.

Example 3

Cloning taVP 1 Using afVP 1

Plant Material;

Wheat variety Soleil was obtained from Dr John Flintham (John Innes Centre, Norwich, UK). This variety was chosen because it has a high resistance to PHS. Mature seeds were obtained from plants grown outdoors during the summer. Air dry seeds were stored in the dark at −20° C. to maintain dormancy levels prior to RNA extractions.

Germination Assays

These were conducted as described for afVP1.

Extraction and Analysis of RNA From Wheat Seeds

Poly-A containing RNA was extracted from seeds as described previously (Rushton et al 1995). Otherwise the process was as for afVP1.

cDNA Library Construction Screening and Manipulation of Nucleic Acids cDNA library construction was carried out a previously described (Holdsworth et al 1992) using poly-A containing RNA from mature embryos of the wheat variety Soleil. 500 Soleil seeds (harvested 1996) were imbibed at 20° C. for 8 hours. Embryos were dissected out and poly(A)RNA extracted (approximately 65 μg). Northern analysis using a fragment of afVP 1 (bases 600–1892) as a probe confirmed the presence of wheat homologues in the RNA preparation. 5 μg poly(A)RNA was used to construct the cDNA library (Amersham plc cDNA synthesis kit). Oligo dT primed cDNA was ligated into the vector λXAP II (Stratagene). $10^6$ plaque-forming units from the primary library were amplified to obtain an amplified library with final titre of $10^7$ pfu/ml. This library was screened using the hybridisation and washing conditions described above for Northern analysis. Wheat VP 1 homologues were identified using as a probe either a fragment of the afVP 1 cDNA from the 5' end (basis 1–892 of afVP 1), or a fragment from the middle of afVP 1 (bases 600–1892). A total of 8 cDNA clones were purified and characterised, all showing specific hybridisation of the afVP 1 cDNA.

Sequencing of cloned cDNA products was performed manually by the dideoxy chain termination method (Sanger et al 1997), or for the longest cDNA clone (Clone 10, 2.3 kbp) via contracting out (Oswel, University of Southampton). DNA sequence analysis was carried out using the MacVector™ and AssemblyLine™ programmes (Oxford Molecular Group plc, UK) and GCG8 (University of Wisconsin Genetics Computer Group version 8 [Genetics Computer Group 1994]). The wheat cDNA clones shared 81% DNA sequence identity with the afVP 1 clone.

Example 4

Method for Reducing PHS in Wheat by use of afVP1 Sequence

Wheat transformation is conveniently carried out according to Barcelo & Lazzeri (1995) in Methods in Molecular Biology, Vol 49. Chapter 9, pp 113–124; Ed H Jones, Humana Press, Totowa, New Jersey. This employs microprojectile bombardment of immature inflorescence and scutellum tissues; the content of this paper is indicative of the ability of those skilled in the art to perform wheat transformation without burden. Other common methods for transforming wheat are discussed by Christou in Trends in Plant Science (1996)1, 12: 423–431, and by Chang et al in U. S. Pat. No. 5,610,042. For the avoidance of doubt any content of these documents not forming part of the common general knowledge is herein incorporated by reference. Briefly, the full-length afVP 1 cDNA (or a truncated derivative) is cloned into a wheat transformation vector downstream of the rice actin promoter, which confers constitutive expression of afVP 1, or the ubiquitin promoter. Immature embryos or inflorescences are bombarded with gold microcarriers coated with plasmid DNA. Explants are cultured, selected and plants are regenerated. Transgene expression is then assayed e.g. using a GUS marker.

More specifically transgenic wheat containing sense and antisense afVP1 constructs was produced and analysed as follows:

a. Description of afVP1 Constructions:

Sense and antisense versions of afVP1 were cloned into the plant transformation/expression vector pUPLN, that contains the ubiquitin promoter upstream of a multiple cloning region (MCR). This plant transformation vector was constructed in the laboratory of Dr. Paul Lazzeri (IACR-Rothamsted). It contains the Ubiquitin promoter and first intron and exon, and the NOS terminator DNA sequence from the plamid pAHC17 (Christensen and Quail, Transgenic Research 5, 213–218; 1996). These DNA sequences were introduced into the plamid pSP72 to create PUPLN.

A Notl DNA fragment containing only the complete afVP1 CDNA was introduced into pUPLN at the Not I site within the MCR. Subclone's were identified as containing the afVP 1 in the "sense" of "antisense" orientation with respect to the ubiquitin promoter, by digestion of plamid DNA with Spel (that distinguishes afVP 1 insert orientation because both the afVP 1 cDNA and pUPLN contain a single site each).

b. Transformation of Wheat

This was carried out as described above. pUPLN plamid DNA containing afVP 1 in either sense of antisense orientation were separately transformed into wheat (cultivars used were; Cadenza, Canon, Riband, lmp and Avans, information is shown for Cadenza and Canon).

C. Identification of Transgenic Plants:

i) Using PCR to Show Wheat Plants Contain afVP 1 DNA Sequence:

PCR was carried out as already described.

Oligonucleotide's specific to afVP 1 were used with wheat genomic DNA derived from putative transgenic plants to amplify a portion of the afVP 1 CDNA within the PUPLN plamid integrated into wheat genomic DNA.

The oligonucleotides were:

(5': 63967: bases 1410–1429 of EMBL deposited afVP 1 sequence):
5' CAA CTC ATG GTC CCG AAT CC 3'

(5': afVP1 EPRIME: bases 2285–2302 of EMBL deposited afVP 1 sequence):
5' GCT TGT TAG ACG AAT TGA C 3'

The results of this experiment demonstrated that transgenic plants have been identified that separately contain copies of sense and antisense afVP 1 cDNA.

ii) Northern Analysis of Transgenic Antisense Plants:

Total RNA was extracted from leaf material using a Qiagen™ kit.

N-blot production and analysis carried out as described in Sambrook et al (1989, supra). The probe used was a radio-labelled an afVP 1, 1.4 Kbp Not/Hind III DNA fragment, containing 1.4 kbp at the 3 prime end of the cDNA.

The results of this experiment are shown in FIG. 9. This shows that the transgenic plants analysed express antisense afVP 1 in leaf material to a very high level. One specific hybridising transcript is detected in leaf total RNA from transgenic line #33 (within cultivar Cadenza). Control RNA derived from untransformed leaf material of the same cultivar did not show hybridisation to the afVP 1 probe.

Example 5

Mapping taVP1 and OsVP1

Mapping in Wheat

An afVP1 CDNA clone ('lars10'—taVP1 ) was used to identify the chromosomal location of taVp1 loci in hexaploid wheat and identify a restriction fragment length polymorphism (RFLP) which was used for genetic mapping. Using nullisomic-tetrasomic lines of the wheat cultivar 'Chinese Spring' in genomic Southern analysis, the presence of taVp1 homologs on each group 3 chromosome was established. Two RFLPs were identified between the wheat cultivars 'Chinese Spring' and 'Synthetic' in an EcoR1 DNA digest. This enabled taVp1 to be mapped on chromosomes 3A and 3D using the $F_2$ population from 'ChineseSpring'× 'Synthetic' cross of Devos et al (1992).

The 3B orthologue was not polymorphic in digests with EcoRl, EcoRV, DraI or HindIII and was not mapped. Mapping data were incorporated into the existing linkage map for this cross using MAPMAKER version 3.0. On chromosome 3A, Xlars10 (taVp1) is positioned distal to marker Xpsr549 by 12.1 cM and proximal to marker Xabg389 by 3.9 cM. The 3D homoeolocus is distal by 12.1 cM to Xpsr 170 and proximal to Xpsr 1067 by 5.5 cM. These two gene locations are consistent with the location shown in FIG. 7, the the interval Xpsr549—Kwg110 on the wheat group 3 consensus map of Gale et al. (1995), about 30 cM from the centromere. Xlars10 (taVp1) shows clear recombination with *R loci* which map about 60 cM from the centromere. Thus, although Xlars10 (taVp1) and R are linked, they are clearly distinct genes.

Thus the results show that both wheat carries a Vp1 orthologue in loose genetic linkage with previously mapped genes controlling seedcoat pigments (*R loci* in wheat). It is proposed that this genetic separation between the two loci reflects separate roles for taVp1 and R respectively in zygotic and maternal dormancy mechanisms. To date no QTL mapping the proximity of Xlars10 had been detected in wheat (Anderson et al 1993). QTL for malting quality that map to the long arm of chromosome 3 in barley vary in position between genetic crosses and different environments, and it is not clear whether these QTL reflect effects on dormancy (compare for example, Hayes et al. 1993 c.f Oberthur et al. 1995).

Assigment of VP1 cDNA Clones to the A and D Genomes of Wheat

Background

An alignment of sequences from six Vp1 cDNA clones demonstrated that the clones fall into two main groups characterised by single base pair differences at a number of places along the sequence, illustrated in FIG. 11 for a section of cDNA (group 1: clones 4, 5 and 10; group 2: clones 3, 6 and 9). Each group appears to represent a single genomic copy gene (one set from a gene on a chromosome 3A, the other on 3D). The differences between the clones on each family may therefore have arisen by post-transcriptional modifications (e.g. differential splicing to form mature mRNA). This suggests that there may be advantages in tagging taVP1 mRNA and/or polypeptides (rather than genomic alleles) to assess taVP1 function (and hence PHS or other dormancy traits)

Methods

PCR primers were designed to specifically amplify each sequence group from genomic DNA. FIG. 11 illustrates the location of the 3' end of the forward primers, designed to coincide with the base pair differences existing between each group:

primer 4 forward: 5' AATATCTGATACGCGGCGT-GAAGGTG3' primer 9 forward: 5' AGGATCTAGCCAAGCACAA-GAATGG3'

The 3' end of the reverse primers were designed in a similar way:

primer 4 reverse: 5'GCCCATATGAACTCGATCGAT-TGAC 3' primer 9 reverse: 5'GTTGTCCATATGAACTCGATC-GATTC 3'

The reaction conditions are described below:

1X Taq buffer (Boehringer)

1.2 mM $MgCl_2$

200 $\mu$M of dGTP, DATP, dUTP and dCTP 0.4 $\mu$M of each primer 1.5 U/100 $\mu$l Taq polymerase (Boehringer)

50 ng genomic DNA

The total reaction volume was 50 $\mu$l. The PCR cycles were:

Five cycles of:
- 94° C. 1 minute
- 70° C. 1 minute
- 72° C. 1 minute

Thirty cycles of:
- 94° C. 45 seconds
- 65° C. 1 minute
- 72° C. 1 minute

Results

The result of the PCR on various templates is shown in FIG. 12. Plasmid DNA from clones four (4) and nine (9) represent the two sequence groups and act as control templates; primer set 4 is specific to one group and primer set nine is specific to the other. For genomic DNA from a nullisomic-tetrasomic line of Chinese Spring in which the 3A chromosome is absent (N3A/T3D), amplification does not occur. However, when the 3B chromosome (in N3B/T3A lines) or 3D chromosome (in N3D/T3A lines) is absent amplification can still occur. This demonstrates that clone 4 represents the gene located on chromosome 3A.

For the primer set designed to the other sequence group, amplification occurs using DNA from nulli-tetra lines in which the 3A and 3B chromosomes are missing but amplification is abolished in lines missing 3D. This demonstrates that clone 9 represents the gene located on chromosome 3D.

Genomic clones for all three genome copies have been identified in a Soleil genomic library. Genome-specific primers will be useful for targetting each copy of Vp1 and studying correlations of particular Vp1 alleles with dormancy/preharvest sprouting. They may also have particular utility in assessing introgression into specific wheat genomes, for instance from wild relatives.

Example 6

Use of the taVP1 as a Marker for Dormancy in Breeding Programmes

Superior alleles of taVp1 may be identified by cloning (e.g. using probes/primers based on the sequences disclosed herein e.g. in FIG. 10) and sequencing alleles from a variety of lines, and correlating the sequence with the PHS properties of those plants. PCR primers which are specific for "superior" alleles can then be used to select preferred genotypes. This allows early-generation selection against PHS using a rapid, small-scale method, in contrast with current practise of delaying selection until late generations and using extremely cumbersome and rather unreliable empirical dormancy tests.

Dormancy may be improved by selection for high levels of expression of fully-functional alleles, firstly by selecting parents carrying desirable genomic copies of taVp1 gene(s), then by selecting progeny which express these alleles strongly at appropriate stages of seed development and maturation.

Desirable alleles may be obtained from within the existent wheat (*Triticum aestivum*) genepool, but may also be detected and transferred from one or more of the many wild or cultivated relatives of wheat, for which established methods are available for the introduction of "alien" variation into the hexaploid. The recombining of wheat/alien chromosomes is a standard technique, see e.g. M. D. Gale & T. E. Miller. 1987. The introduction of alien genetic variation into wheat. pp173–210 in: Wheat Breeding Its Scientific Basis. Ed. F. G. H. Lupton. Chapman & Hall. Wheats carrying such alleles could then be crossed into a commercial breeding programme and varieties resistant to PHS due to the presence of superior alleles could be identified eg. by PCR using allele-specific primers.

For applications in which dormancy is undesirable, eg. grain for brewing, the same information and techniques could be employed to select in the reverse direction, i.e. to fix defective or poorly expressed copies of taVp1 (malting wheat).

Example 7

Use of the taVP1 for Predicting the Susceptibility to PHS

A taVP1 based test for predicting the onset of PHS in commercial crops would enable farmers to prioritise harvesting of high-quality varieties. Present attempts to do this only use weather data (P. S. Kettlewell, G. D. Lunn, B. J. Major, R. K. Scott, P. Gate & F. Couvreur, 1995. A possible scheme for pre-harvest prediction of Hagberg Falling Number and sprouting of wheat in the U.K. and France. p35–41 in: Pre-Harvest Sprouting in Cereals 1995. Eds. K. Noda & D. J. Mares. Centre for Academic Societies Japan). The level of effective taVp1 activity in the seed may be measured e.g. using a PCR-based or antibody assays in order to predict susceptibility to PHS.

References:

Bob, A. J. Eiben, H. G. Bustos, M. M. (1995) PvAlf, an embryo-specific acidic transcriptional activator enhances gene expression from phaseolin and phytohemagglutinin promoters. *The Plant Journal* 8, 331–343.

Cuming, A. C. and Osborne, D. J. (1978) Membrane turnover in imbibed and dormant embryos of the wild oat (*Avena fatua L.*) *Planta* 139, 209–217.

Elder, R. H. and Osborne, D. J. (1993) Function of DNA synthesis and repair in the survival of embryos during early germination and in dormancy. *Seed Science Research* 3, 43–53.

Foley, M. E. (1994) Temperature and water status of seed affect after-ripening in wild oat (*Avena fatua*) *Weed Science* 42, no.2, 200–204.

Gale, M. D. Lenton, J. R. (1987) Preharvest sprouting in wheat- a complex genetic and physiological problem affecting breadmaking quality in UK wheats. *Aspects of Applied Biology* 15, 115–124.

Genetics Computer Group (1994). The Wisconsin Sequence Analysis Package, Version 8.0, University Research Park, 575 Science Drive, Madison, Wis. 53711, USA.

Giraudat, J. Hauge, B. M. Valon, C. Smalle, J. Parcy, F. Goodman, H. M. (1992) Isolation of the Arabidopsis ABI 3 gene by positional cloning. *The Plant Cell* 4, 1251–1261.

Grierson, C. S. (1992) Transcriptional regulators of patatin gene expression. PhD Thesis, University of Cambridge, Cambridge, UK.

Hattori, T. Terada, T. Hamasuna, S. (1994) Sequence and functional analyses of the rice gene homologous to the maize Vp 1. *Plant Mol. Biol.* 24, 805–810.

Hattori, T. Vasil, V. Rosenkrans, L. Hannah, L. C. McCarty, D. R. Vasil, I. K. (1992) The Viviparous-1 gene and abscisic acid activate the C1 regulatory gene for anthocyanin biosynthesis during seed maturation in maize. *Genes and Dev.* 6, 609–618.

Hilhorst, H. W. M. and Karssen, C. M. (1992) Seed dormancy and germination: The role of abscisic acid and gibberellins and the importance of hormone mutants. *Plant Growth Regulation* 11, 225–238.

Hill, A. Nantel, A. Rock, C. D. Quatrano, R. S. (1996) A conserved domain of the Viviparous-1 gene product enhances the DNA binding activity of the bZIP protein EmBP-1 and other transcription factors. *J. Biol. Chem.* 271, 3366–3374.

Hoecker, U. Vasil, I. K. McCarty, D. R. (1995) Integrated control of seed maturation and germination programs by activator and repressor functions of Viviparous-1 of maize. *Genes and Development* 9, 2459–2469.

Holdsworth, M. J. Grierson, C. S. Schuch, W. Bevan, M. (1992) DNA-binding properties of cloned TATA-binding protein from potato tubers. *Plant Mol. Biol.* 19, 455–464.

Hooley, R. Beale, M. H Smith, S. J. (1991) Gibberellin perception at the plasma-membrane of *Avena-fatua* aleurone protoplasts. *Planta* 183, no.2, 274–280.

Jana, S. Acharya, S. N. Naylor, J. M. (1979) Dormancy studies in seed of *Avena fatua*. 10. On the inheritance of germination behaviour. *Can. J. Bot.* 57, 1663–1667.

Jana, S. Upadhyana, M. K. Acharya, S. N. (1988) Genetic basis of dormancy and differential response to sodium azide in *Avena fatua* seeds. *Can. J. Bot.* 66, 635–641.

Johnson, R. R. Cranston, H. J. Chaverra, M. E. Dyer, W. E. (1995) Characterisation of CDNA clones for differentially expressed genes in embryos of dormant and nondormant *Avena fatua L. caryopses. Plant Mol. Biol.* 28, 113–122.

Jones, H. D. (1996) The role of G-proteins in intracellular signalling mechanisms of wild oat (*Avena fatua*) aleurone. PhD Thesis, University of Bristol, Bristol, UK.

Koornneef, M and Karssen, C. M. (1994) Seed dormancy and germination. In Arabidopsis (Meyerowitz, E. M. and Somerville, C. R. eds) Cold Spring Harbor Laboratory Press, 313–334.

Leung, J. Bouvier-Durand, M. Morris, P-C. Guerrier, D. Chefdor, F. Giraudat, J. (1994) Arabidopsis ABA response gene ABI 1: Features of a calcium-modulated protein phosphatase. *Science* 264, 1448–1455.

Li, B. and Foley, M. E. (1995) Cloning and characterisation of differentially expressed genes in imbibed dormant and after-ripened *Avena fatua* embryos. *Plant Mol. Biol.* 29, 823–831.

Mayer, A. M. Poljakoff-Mayber, A. (1989) The germination of seeds. Fourth edition. Pergamon Press, Oxford U. K.

McCarty, D. R. Hattori, T. Carson, C. B. Vasil, V. Lazar, M. Vasil, I. K. (1991) The Viviparous 1 developmental gene of maize encodes a novel transcription activator. *Cell* 66, 895–905.

Nambara, E. Keith, K. McCourt, P. Naito, S. (1995) A regulatory role for the ABI 3 gene in the establishment of embryo maturation in *Arabidopsis thaliana*. Development 121, 629–636.

Ooms, J. J. Leon-Kloosterziel, K. M. Bartels, D. Koornneef, M. Karssen, C. M (1993) Acquisition of desiccation tolerance and longevity in seeds of *Arabidopsis thaliana*. *Plant Physiol.* 102, 1185–1191.

Palazzolo, M. J. Hamilton, B. A. Ding, D. Martin, C. H. Mead, D. A. Mierendorf, R. C. Raghavan, K. V. Meyerowitz, E. M. Lipshitz, H. D. (1990) Phage lambda cDNA cloning vectors for subtractive hybridisation, fusion-protein synthesis and cre-loxP automatic plasmid subcloning. *Gene* 88, 25–36.

Parcy, F. Valon, C. Raynal, M. Gaubier-Comella, P. Delseny, M. Giraudat, J. (1994) Regulation of gene expression programs during Arabidopsis seed development: Roles of the ABI 3 locus and of endogenous abscisic acid. *The Plant Cell* 6, 1567–1582.

Peters, N. C. B. (1991) Seed dormancy and seedling emergence studies in *Avena fatua* L. *Weed Research* 31, 107–116.

Rushton, P. J. Hooley, R. Lazarus, C. M. (1992) Aleurone nuclear proteins bind to similar elements in the promoter regions of 2 gibberellin-regulated alpha-amylase genes. *Plant Molecular Biology*. 19, 891–901.

Sambrook, J. Fritsch, E. F. Maniatis, T. (1989) *Molecular Cloning; a laboratory manual*. Cold Spring Harbor Laboratory Press.

Sanger, F. Nicklen,S. Coulson, A. R. (1977) DNA sequencing with chain-terminating inhibitors. *Proc. Natl.Acad. Sci.* (*USA*). 74, 5463–5467.

Simpson, G. (1978) Dormancy in *Avena fatua*: A case history. In *Dormancy and Developmental Arrest* (Clutter, M. ed). Academic Press, New York. 141–191.

Trewavas, A. J. (1987) Timing and memory processes in seed embryo dormancy-A conceptual paradigm for plant development questions. *Bioessays* 6, 87–91.

Vasil, V. Marcotte, W. R. Rosenkrans, L. Cocciolone, S. M. Vasil, I. K. Quatrano, R. S. McCarty, D. R. (1995) Overlap of Viviparous 1 (VP 1) and abscisic acid response elements in the Em promoter: G-box elements are sufficient but not necessary for VP 1 transactivation. *The Plant Cell* 7, 1511–1518.

Williamson, J. D. Quatrano, R. S. Cuming, A. C. (1985) Em polypeptide and its messenger-RNA levels are modulated by abscisic-acid during embryogenesis in wheat. *European Journal of Biochem.* 152, 501–507.

Additional References:

Ahn S, Tanksley S D (1993) Comparative linkage maps of the rice and maize genomes. Proc. Natl. Acad. Sci. USA 90:7980–7984.

Bobb A J, Eiben H G, Bustos M M (1995) PvAlf, an embryo-specific acidic transcriptional activator enhances gene expression from phaseolin and phytohemagglutinin promoters. Plant J. 8:331–343.

Cadle M M, Rayfuse L M, Walker-Simmons M K, Jones S S (1994) Mapping of abscisic acid responsive genes and Vp1 to chromosomes in wheat and *Lophopyrum elongatum*. Genome 37:129–132.

Derera N F (1989) The effects of preharvest rain. In: Preharvest field sprouting in cereals. Ed Derera N F. CRC Press Inc.

Devos K M, Atkinson M D, Chinoy C N, Liu C J, Gale M D (1992) RFLP-based genetic map of the homeologous group 3 chromosomes of wheat and rye. Theor Appl Genet 83:931–939.

Devos K M, Atkinson M D, Chinoy C N, Francis H A, Harcourt R L, Koebner R M D, Liu C J, Masojćp, Xie D X, Gale M D (1993) Chromosomal rearrangements in the rye genome relative to that of wheat. Theor. Appl. Genet. 85:673–680.

Flintham J E, Humphrey S J (1993) Red coat genes and wheat dormancy. Aspects of Applied Biology 36.

Flintham J E, Gale M D (1995) Dormancy gene maps in homoeologous cereal genomes. pp143–149 in: Pre-Harvest Sprouting in Cereals 1995. Eds Noda K, Mares D J. Center for Academic Societies Japan.

Gale M D, Atkinson M D, Chinoy C N, Harcourt R L, Jia J, Li Q Y, Devos K M (1995) Genetic maps of hexaploid wheat. pp29–40 in: Proceedings of the 8th International Wheat Genetics Symposium. Eds Li ZS, Xin ZY. China Agricultural Scientech Press, Beijing.

Giraudat J, Hauge B M, Valon C, Smalle J, Parcy F (1992) Isolation of the Arabidopsis Abi3 gene by positional cloning. Plant Cell 4:1251–1261.

Hattori T, Terada T, Hamasuna S T (1994) Sequence and functional analyses of the rice gene homologous to the maize Vp1. Plant Mol. Biol. 24:805–810.

Jones H D, Peters NCB, Holdsworth M J (1997) Genotype and environment interact to control dormancy and differential expression of the VIVIPAROUS 1 homologue in embryos of *Avena fatua*. Plant J. in press.

Kurata N, Moore G, Nagamura Y, Foote T, Yano M, Minobe Y, Gale M (1994) Conservation of genome structure between rice and wheat. Bio/Technol. 12:276–278.

McCarty D R, Hattori T, Carson C B, Vasil V, Lazar M, Vasil IK (1991) The viviparous-1 developmental gene of maize encodes a novel transcriptional activator. Cell 66:895–905.

Moore G, Devos K M, Wang Z, Gale M D (1995) Grasses line up and form a circle. Current Biology 5:737–739.

Phillips J, Conrad U (1994) Genomic sequences from *Nicotiana tabacum* homologous to the maize transcriptional activator gene Viviparous-1. J. Plant Physiology 144:760–761.

Quarrie (1997) PMB submitted Saghai Maroof M A, Yang G P, Biyashev R M, Maughan P J, Zhang Q (1996) Analysis of the barley and rice genomes by comparative RFLP linkage mapping. Theor Appl Genet 92:541–551.

Van Deynze A E, Nelson J C, O'Donoughue L S, Ahn S N, Siripoonwiwat W, Harrington S E, Yglesias E S, Braga D P, McCouch S R, Sorrells M E (1995a) Comparative mapping in grasses. Oat relationships. Mol. Gen. Genet. 249:349–356. Van Deynze A E, Nelson J C, Yglesias E S, Harrington S E, Braga D P, McCouch S R, Sorrells M E (1995b) Comparative mapping in grasses. Wheat relationships. Mol Gen Genet 248:744–754.

Further References

Anderson et al (1993): Crop Sci 33:453–459

Hayes et al (1993): Barley Genet Newsl 23:98–142

Oberthur et al (1995): J Quant Trait Loci (8pp, online http://probe.nalusda.gov:8000/otherdocs/jqtll1995–05/dormancy.html)

What is claimed is:

1. An isolated nucleic acid molecule encoding *Avena fatua* viviparous 1 (afVP1) comprising a nucleotide sequence identical to SEQ ID NO: 1 or degeneratively equivalent thereto.

2. A nucleic acid which is the complement of the nucleic acid of claim 1.

3. A recombinant vector comprising the nucleic acid of claim 1.

4. A host cell comprising the vector as claimed in claimed 3.

5. A method for transforming a plant cell, comprising the step of introducing the vector as claimed in claim 3 into a cell, and causing or allowing recombination between the vector and the plant cell genome to introduce the nucleic acid into the genome.

6. A method for producing the transgenic plant comprising a method as claimed in claim 5 and further comprising the step of regenerating a plant from the transformed cell.

7. A method of producing a polypeptide comprising the step of causing or allowing the expression of the nucleic acid of claim 1 in a suitable host.

8. A method for increasing the dormancy of a seed or grain, the method comprising the step of causing for allowing expression of the nucleic acid according to claim 1 within the seed or grain.

9. A wheat plant comprising the cell of claim 4.

* * * * *

SEQUENCE LISTING

<160> NUMBER OF SEQ ID NOS: 34

<210> SEQ ID NO 1
<211> LENGTH: 2324
<212> TYPE: DNA
<213> ORGANISM: Avena fatua

<400> SEQUENCE: 1

```
gcacaccct  tcttccctcc  ttccctccct  cctcctcct  gccttcctt  tgcatggacg      60
cctccgccgg  ctcctcgccg  ccgccgcact  cgcaggagaa  cccgcccaag  cacggtggag   120
gccgcgggaa  gcgtgcgggg  gagatccgga  agggagaggc  ggccacggcg  gatgactta   180
tgttcgcgga  agataccttc  ccgtccctcc  cggatttccc  ttgcctctcc  tcccgttcaa   240
gctccacctt  ctcctcctca  tcctcctcca  actcatccag  cacccacgcc  gccgcgggac   300
gcggcgtggc  cgttgtcgcg  gacgcccgaa  ggcgcctcgg  ggagccctcc  gatcctgctg   360
ccgcggggga  cgatgacgtg  ctcgacgaca  tcgacgagct  gctcaactct  gccacgctct   420
ccgactccat  gccctgggag  gacgagccgc  tcttccccga  cgacgttggc  atgatgatag   480
aggacgccat  ctcccaccag  ccgcccgcca  cgggccaccg  cggagccagg  aacgctgcat   540
catcggaggc  ggctgctggt  ggtggtggac  aggattcctc  gtcggcggac  gacctgccgc   600
ggttcttcat  ggagtggctg  acgaacaacc  gcgactgcat  ctccgccgag  gacctccgca   660
gcatccgcct  ccgccgctcg  accatcgagg  ccgcggcggc  gcggctcggt  ggagggcggc   720
agggcaccat  gcagctgctc  aagctcatcc  tcacatgggt  gcagaaccac  catctgcaga   780
agaagcgcgc  ccgcgtcgac  gacgagctcc  ccagcccccg  cgcaaacccg  ggttacgagt   840
tccccgcgga  gacagttgcc  cccgccacat  cctggctcat  gccctaccaa  caagcttatg   900
gaagagaggc  gatctacccg  aacgccgccg  ccaccgggca  gtacccattc  cagcaggcg   960
gcagcacgag  cagcgtggtg  gtgagcagcc  agccgttctc  cccgccggcg  ccggtggccg  1020
acatgcaggc  ggcgaacatg  ccctggccgc  agcagtacgc  ggcgttcccc  ggcgctgcgc  1080
catcccgat   gccgccgccg  cagccgttgg  cggcggccgg  attcggcgtg  tgcccgcagc  1140
ccttggccgg  ggtgaagccg  tcggcgagca  aggaggcccg  gaagaagcgt  atggcgaggc  1200
agcgccgcct  ctcctgcctg  cagcatcagc  ggagccagca  gctgaatctg  ggccagatcc  1260
agaacgccat  gatccatccg  cagcaggagg  tgccgttctc  tccccgctcc  gcgcactcgg  1320
tgcctgtctc  accgccgtcg  cccggcggct  ggtgcgggct  ctggccgccg  ccctccgtcc  1380
aagtccaggg  ccagggccaa  ctcatggtcc  cgaatccgct  gtcgacaaag  cccagttcct  1440
cctcgaggca  gaaggcgcag  aaaccctcgc  cggacgcagg  agcaagaccg  ccgtcgtccg  1500
gcgcgcagca  gggtgcgaag  ccgggggcgg  acaagaatct  gcggttcctg  ctgcagaagg  1560
tgctgaagca  gagcgacgtc  ggcgccctcg  gccgcatcgt  gctccccaaa  gaagcggaga  1620
cgcacctgcc  ggagctcaag  acgagggacg  gcatctccat  cccatggag  gacatcggca   1680
```

-continued

```
cctctcgggt ctggagcatg cggtaccggt tttggcctaa caacaagagc agaatgtatc     1740
tccttgagaa cactggggac tttgttcgct caaacgagct gcaggagggc gacttcatcg     1800
tgatttactc agatgtcaag tcgggcaaat atctgatacg tggtgtgaag gtaagaccgc     1860
cgcaggatct agcgaagcag aagcatggca gtctagagaa aggcagcacc tcagatgcga     1920
tgccctgcgc tgaagacggt ggcgccgagg caggcggctg caaggggaag tctccgcacg     1980
gcgttaggcg gtctcgccag gaggctgcgt ccatgaacca gatggcggtg agcatctgaa     2040
agaacagccc tagacgatcc accattgaag acttagctag ctcgtgtata catgatgttg     2100
atgatcaaat cgatctctgg caccgttgta ttatccgtag tactctagcc ctagggatgg     2160
ttatatatta aagtagctat cagtccgatg tgacgactaa agaatgcatg gtttggttcg     2220
ttaaaaccct gtaaccctgt acatgcatga acataataac ttatttgtcg tgtcaattcg     2280
tctaacaagc agactagttc ctgccgtaaa aaaaaaaaaa aaaa                     2324
```

<210> SEQ ID NO 2
<211> LENGTH: 2332
<212> TYPE: DNA
<213> ORGANISM: Triticum aestivum

<400> SEQUENCE: 2

```
ggcacgagga cgacttcatg ttcgcgcacg ataccttccc ggccctcccg gacttcccctt      60 gcctctcctc gccgtcgagc tccaccttct cctcctcgtc gtcttccaac tcctccagcg     120
ccttcacccg cgccgtgggg gcaggcgggc gcggggggcga gagtgcgcgc ggcgagccgt     180
ccgagcctgc cgcggccggg gacgggatgg acgacctctc cgacatcgac cacctgctcg     240
acttcgcatc catcaacgag gacgtcccctt ggacgacga gccgctcttc cccgacgtcg     300
ggatgatgct ggaggacgtc atctccgagc agcagcagtt gcaacctccg gcgggccacg     360
gcacggccgg gagaacggcg tcgcatgcgg ctgctggtgg aggagaggat gccttcatgg     420
gtggcggcgg cacggggagc gcggcggacg acctgccgcg cttcttcatg gagtggctca     480
agaacaaccg cgactgcatc tcggccgagg acctccgcag catccgcctc cgtcgatcca     540
ccatcgaggc cgcggccgcg cgcctcggtg ggggcgcca gggcaccatg cagctgctca     600
agctcatcct cacctgggtg cagaaccacc acctgcagaa gaagcgcccc cgcgtcggcg     660
ccatggatca ggaggcgctg ccggcaggag gccagctccc tagccccggc gcaaaccccg     720
gctacgaatt ccccgcggag acgggtgccg ccgctgccac atcttggatt ccctaccagg     780
ccttctcgcc aactggatcc tacggcggcg aggcgatcta cccgttccag cagggctgca     840
gcacgagcag cgtgggcgtg agcagccagc cgttctcccc gccggcggcg cccgacatgc     900 acgccgggggc ctggccgctg cagtacgcgg cgttcgtccc agctggggcc acatccgcag     960
gcactcaaac ataccgatg ccgccgccgg gggccgtgcc gcagccgttc gcggccccccg     1020 gattcgccgg gcagttcccg cagcggatgg agccggcggc gaccagggag gcccggaaga     1080
agaggatggc gaggcagcgg cgcctgtcgt gcctgcagca gcagcggagc cagcagctga     1140
atctgagcca gatccaaacc ggcggcttcc ctcaagagcc atcccccgc gcggcgcact     1200 cggcgccggt cacgccgccg tcgtctggct ggggaggcct ctggacgcaa caagccgtcc     1260
agagccagcc ccatggccag ctcatggtcc aggtcccgaa tccgctgtcg acgaagtcca     1320
attcctcaag gcagaagcag caaaaaccct cgcggacgc agcagcgagg ccgccctccg     1380
gcggcgccgc cacgccgcag cgcccgggc aggcggcggc ttccgacaag cagcggcagc     1440
aggtgcatgc atgcacgaac acctcttgcc atccatccat cgatcgccat cccgcataga     1500
```

```
atcacaagcc attgctcccc aaataagtgg tgcgaggacg ccggcggcgg cgccggcggc    1560
aggagacaag aacccgcggt tcctgctgca gaaggtgctc aagcagagcg acgtcggaac    1620
cctcggccgc atcgtgctcc ccaaagaagc ggagactcac ctgccggagc tcaagacggg    1680
ggacggcatc tcgatcccca ttgaggacat cggcacatct cagattttgg cccaacaaca    1740
agagcagaat gtatcttcta gagaacactg gtgactttgt tcggtcgaat gagctgcagg    1800
agggtgattt catcgtgctt tactctgatg tcaagtcggg caaatatctg atacgcggcg    1860
tgaaggtgag agcgcaacag gatctagcca agcacaagaa tgccagtcca gagaaggcg     1920 gggcgtccga cgtgaaggcg ggcggagaag acggcggctg caaggagaag ccccccacg     1980 gcgtccggcg atctcgccag gaggccgcct ccatgaacca gatggcggtg agcatctgaa    2040
atgagcaggc tcgccgtccg atccaccatt gaagactcag ttagctagct caagtatacc    2100
cgttgatgat gatcaaatcg atctctcgtt ctatgatccg tgcttccgtg tactgctgta    2160
gccctagtta gggatgatga tactaaagta gctatcggtc agatgtgacg ctgaagaatg    2220
catggtccgt gctgttaaac ctgtataaag gctgtaaccc ttctgtacat gcatgaacat    2280
acccttattt gttgtgtgtt gtcctcctaa aaaaaaaaaa aaaaaaaaa aa             2332
```

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
cgtcacatct gaccgatagc                                                  20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 4
catctcaggt gtggagcatg c                                                21

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 5
cggcacatct cagattttgg ccc                                              23

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 6
gcggcagcag ggtgcgagg                                                   19

<210> SEQ ID NO 7
```

-continued

```
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 7
gcggcagcag gtgcatgcat g                                              21

<210> SEQ ID NO 8
<211> LENGTH: 661
<212> TYPE: PRT
<213> ORGANISM: Avena fatua

<400> SEQUENCE: 8
```

| | | | | | | | | | | | | | | |
|---|---|---|---|---|---|---|---|---|---|---|---|---|---|---|
| Met | Asp | Ala | Ser | Ala | Gly | Ser | Ser | Pro | Pro | His | Ser | Gln | Glu | Asn |
| 1 | | | | 5 | | | | | 10 | | | | | 15 |
| Pro | Pro | Lys | His | Gly | Gly | Gly | Arg | Gly | Lys | Arg | Ala | Gly | Glu | Ile | Arg |
| | | | 20 | | | | | 25 | | | | | 30 | | |
| Lys | Gly | Glu | Ala | Ala | Thr | Ala | Asp | Asp | Phe | Met | Phe | Ala | Glu | Asp | Thr |
| | | 35 | | | | | 40 | | | | | 45 | | | |
| Phe | Pro | Ser | Leu | Pro | Asp | Phe | Pro | Cys | Leu | Ser | Ser | Arg | Ser | Ser | Ser |
| 50 | | | | | 55 | | | | | 60 | | | | | |
| Thr | Phe | Ser | Ser | Ser | Ser | Ser | Asn | Ser | Ser | Ser | Thr | His | Ala | Ala |
| 65 | | | | | 70 | | | | | 75 | | | | | 80 |
| Ala | Gly | Arg | Gly | Val | Ala | Val | Val | Ala | Asp | Ala | Arg | Arg | Leu | Gly |
| | | | | 85 | | | | | 90 | | | | | 95 |
| Glu | Pro | Ser | Asp | Pro | Ala | Ala | Ala | Gly | Asp | Asp | Val | Leu | Asp | Asp |
| | | | 100 | | | | | 105 | | | | | 110 | |
| Ile | Asp | Glu | Leu | Leu | Asn | Ser | Ala | Thr | Leu | Ser | Asp | Ser | Met | Pro | Trp |
| | | | 115 | | | | | 120 | | | | | 125 | | |
| Glu | Asp | Glu | Pro | Leu | Phe | Pro | Asp | Asp | Val | Gly | Met | Met | Ile | Glu | Asp |
| | | 130 | | | | | 135 | | | | | 140 | | | |
| Ala | Ile | Ser | His | Gln | Pro | Pro | Ala | Thr | Gly | His | Arg | Gly | Ala | Arg | Asn |
| 145 | | | | | 150 | | | | | 155 | | | | | 160 |
| Ala | Ala | Ser | Ser | Glu | Ala | Ala | Ala | Gly | Gly | Gly | Gln | Asp | Ser | Ser |
| | | | | 165 | | | | | 170 | | | | | 175 |
| Ser | Ala | Asp | Asp | Leu | Pro | Arg | Phe | Phe | Met | Glu | Trp | Leu | Thr | Asn | Asn |
| | | | 180 | | | | | 185 | | | | | 190 | | |
| Arg | Asp | Cys | Ile | Ser | Ala | Glu | Asp | Leu | Arg | Ser | Ile | Arg | Leu | Arg | Arg |
| | | | 195 | | | | | 200 | | | | | 205 | | |
| Ser | Thr | Ile | Glu | Ala | Ala | Ala | Arg | Leu | Gly | Gly | Arg | Gln | Gly |
| | 210 | | | | | 215 | | | | | 220 | | | |
| Thr | Met | Gln | Leu | Leu | Lys | Leu | Ile | Leu | Thr | Trp | Val | Gln | Asn | His | His |
| 225 | | | | | 230 | | | | | 235 | | | | | 240 |
| Leu | Gln | Lys | Lys | Arg | Ala | Arg | Val | Asp | Asp | Glu | Leu | Pro | Ser | Pro | Gly |
| | | | | 245 | | | | | 250 | | | | | 255 |
| Ala | Asn | Pro | Gly | Tyr | Glu | Phe | Pro | Ala | Glu | Thr | Val | Ala | Pro | Ala | Thr |
| | | | 260 | | | | | 265 | | | | | 270 | | |
| Ser | Trp | Leu | Met | Pro | Tyr | Gln | Gln | Ala | Tyr | Gly | Arg | Glu | Ala | Ile | Tyr |
| | | 275 | | | | | 280 | | | | | 285 | | | |
| Pro | Asn | Ala | Ala | Ala | Thr | Gly | Gln | Tyr | Pro | Phe | Gln | Gln | Gly | Gly | Ser |
| | | 290 | | | | | 295 | | | | | 300 | | | |
| Thr | Ser | Ser | Val | Val | Ser | Ser | Gln | Pro | Phe | Ser | Pro | Ala | Pro |
| 305 | | | | | 310 | | | | | 315 | | | | | 320 |
| Val | Ala | Asp | Met | Gln | Ala | Ala | Asn | Met | Pro | Trp | Pro | Gln | Gln | Tyr | Ala |

-continued

```
                    325                 330                 335
Ala Phe Pro Gly Ala Ala Pro Tyr Pro Met Pro Pro Gln Pro Leu
                340                 345                 350
Ala Ala Ala Gly Phe Gly Val Cys Pro Gln Pro Leu Ala Gly Val Lys
                355                 360                 365
Pro Ser Ala Ser Lys Glu Ala Arg Lys Arg Met Ala Arg Gln Arg
            370                 375                 380
Arg Leu Ser Cys Leu Gln His Gln Arg Ser Gln Gln Leu Asn Leu Gly
385                 390                 395                 400
Gln Ile Gln Asn Ala Met Ile His Pro Gln Gln Glu Val Pro Phe Ser
                405                 410                 415
Pro Arg Ser Ala His Ser Val Pro Val Ser Pro Ser Pro Gly Gly
            420                 425                 430
Trp Cys Gly Leu Trp Pro Pro Ser Val Gln Val Gln Gly Gln Gly
            435                 440                 445
Gln Leu Met Val Pro Asn Pro Leu Ser Thr Lys Pro Ser Ser Ser Ser
    450                 455                 460
Arg Gln Lys Ala Gln Lys Pro Ser Pro Asp Ala Gly Ala Arg Pro Pro
465                 470                 475                 480
Ser Ser Gly Ala Gln Gln Gly Ala Lys Pro Gly Ala Asp Lys Asn Leu
                485                 490                 495
Arg Phe Leu Leu Gln Lys Val Leu Lys Gln Ser Asp Val Gly Ala Leu
                500                 505                 510
Gly Arg Ile Val Leu Pro Lys Glu Ala Glu Thr His Leu Pro Glu Leu
            515                 520                 525
Lys Thr Arg Asp Gly Ile Ser Ile Pro Met Glu Asp Ile Gly Thr Ser
    530                 535                 540
Arg Val Trp Ser Met Arg Tyr Arg Phe Trp Pro Asn Asn Lys Ser Arg
545                 550                 555                 560
Met Tyr Leu Leu Glu Asn Thr Gly Asp Phe Val Arg Ser Asn Glu Leu
                565                 570                 575
Gln Glu Gly Asp Phe Ile Val Ile Tyr Ser Asp Val Lys Ser Gly Lys
                580                 585                 590
Tyr Leu Ile Arg Gly Val Lys Val Arg Pro Pro Gln Asp Leu Ala Lys
            595                 600                 605
Gln Lys His Gly Ser Leu Glu Lys Gly Ser Thr Ser Asp Ala Met Pro
    610                 615                 620
Cys Ala Glu Asp Gly Gly Ala Glu Ala Gly Gly Cys Lys Gly Lys Ser
625                 630                 635                 640
Pro His Gly Val Arg Arg Ser Arg Gln Glu Ala Ala Ser Met Asn Gln
                645                 650                 655
Met Ala Val Ser Ile
            660

<210> SEQ ID NO 9
<211> LENGTH: 691
<212> TYPE: PRT
<213> ORGANISM: Zea mays

<400> SEQUENCE: 9

Met Glu Ala Ser Ser Gly Ser Ser Pro Pro His Ser Gln Glu Asn Pro
  1               5                  10                  15
Pro Glu His Gly Gly Asp Met Gly Gly Ala Pro Ala Glu Glu Ile Gly
                 20                  25                  30
```

```
Gly Glu Ala Ala Asp Asp Phe Met Phe Ala Glu Asp Thr Phe Pro Ser
         35                  40                  45

Leu Pro Asp Phe Pro Cys Leu Ser Ser Pro Ser Ser Ser Thr Phe Ser
         50                  55                  60

Ser Asn Ser Ser Ser Asn Ser Ser Ser Ala Tyr Thr Asn Thr Ala Gly
 65                  70                  75                  80

Arg Ala Gly Gly Glu Pro Ser Glu Pro Ala Ser Ala Gly Glu Gly Phe
                 85                  90                  95

Asp Ala Leu Asp Asp Ile Asp Gln Leu Leu Asp Phe Ala Ser Leu Ser
                100                 105                 110

Met Pro Trp Asp Ser Glu Pro Phe Pro Gly Val Ser Met Met Leu Glu
            115                 120                 125

Asn Ala Met Ser Ala Pro Pro Gln Pro Val Gly Asp Gly Met Ser Glu
            130                 135                 140

Glu Lys Ala Val Pro Glu Gly Thr Thr Gly Gly Glu Glu Ala Cys Met
145                 150                 155                 160

Asp Ala Ser Glu Gly Glu Glu Leu Pro Arg Phe Phe Met Glu Trp Leu
                165                 170                 175

Thr Ser Asn Arg Glu Asn Ile Ser Ala Glu Asp Leu Arg Gly Ile Arg
                180                 185                 190

Leu Arg Arg Ser Thr Ile Glu Ala Ala Ala Arg Leu Gly Gly Gly
            195                 200                 205

Arg Gln Gly Thr Met Gln Leu Leu Lys Leu Ile Leu Thr Trp Val Gln
            210                 215                 220

Asn His His Leu Gln Arg Lys Arg Pro Arg Asp Val Met Glu Glu Glu
225                 230                 235                 240

Ala Gly Leu His Val Gln Leu Pro Ser Pro Val Ala Asn Pro Pro Gly
                245                 250                 255

Tyr Glu Phe Pro Ala Gly Gly Gln Asp Met Ala Ala Gly Gly Gly Thr
                260                 265                 270

Ser Trp Met Pro His Gln Gln Ala Phe Thr Pro Pro Ala Ala Tyr Gly
            275                 280                 285

Gly Asp Ala Val Tyr Pro Ser Ala Ala Gly Gln Gln Tyr Ser Phe His
            290                 295                 300

Gln Gly Pro Ser Thr Ser Ser Val Val Val Asn Ser Gln Pro Phe Ser
305                 310                 315                 320

Pro Pro Pro Val Gly Asp Met His Gly Ala Asn Met Ala Trp Pro Gln
                325                 330                 335

Gln Tyr Val Pro Phe Pro Pro Gly Ala Ser Thr Gly Ser Tyr Pro
                340                 345                 350

Met Pro Gln Pro Phe Ser Pro Gly Phe Gly Gln Tyr Ala Gly Ala
            355                 360                 365

Gly Ala Gly His Leu Ser Val Ala Pro Gln Arg Met Ala Gly Val Glu
            370                 375                 380

Ala Ser Ala Thr Lys Glu Ala Arg Lys Lys Arg Met Ala Arg Gln Arg
385                 390                 395                 400

Arg Leu Ser Cys Leu Gln Gln Gln Arg Ser Gln Gln Leu Ser Leu Gly
                405                 410                 415

Gln Ile Gln Thr Ser Val His Leu Gln Glu Pro Ser Pro Arg Ser Thr
            420                 425                 430

His Ser Gly Pro Val Thr Pro Ser Ala Gly Gly Trp Gly Phe Trp Ser
            435                 440                 445

Pro Ser Ser Gln Gln Gln Val Gln Asn Pro Leu Ser Lys Ser Asn Ser
```

-continued

```
                    450                 455                 460
Ser Arg Ala Pro Pro Ser Ser Leu Glu Ala Ala Ala Ala Pro Gln
465                 470                 475                 480

Thr Lys Pro Ala Pro Ala Gly Ala Arg Gln Asp Asp Ile His His Arg
                485                 490                 495

Leu Ala Ala Ala Ser Asp Lys Arg Gln Gly Ala Lys Ala Asp Lys Asn
            500                 505                 510

Leu Arg Phe Leu Leu Gln Lys Val Leu Lys Gln Ser Asp Val Gly Ser
        515                 520                 525

Leu Gly Arg Ile Val Leu Pro Lys Lys Glu Ala Glu Val His Leu Pro
    530                 535                 540

Glu Leu Lys Thr Arg Asp Gly Ile Ser Ile Pro Met Glu Asp Ile Gly
545                 550                 555                 560

Thr Ser Arg Val Trp Asn Met Arg Tyr Arg Phe Trp Pro Asn Asn Lys
                565                 570                 575

Ser Arg Met Tyr Leu Leu Glu Asn Thr Gly Glu Phe Val Arg Ser Asn
            580                 585                 590

Glu Leu Gln Glu Gly Asp Phe Ile Val Ile Tyr Ser Asp Val Lys Ser
        595                 600                 605

Gly Lys Tyr Leu Ile Arg Gly Val Lys Val Arg Pro Pro Ala Gln
    610                 615                 620

Glu Gln Gly Ser Gly Ser Ser Gly Gly Lys His Arg Pro Leu Cys
625                 630                 635                 640

Pro Ala Gly Pro Glu Arg Ala Ala Ala Gly Ala Pro Glu Asp Ala
                645                 650                 655

Val Val Asp Gly Val Ser Gly Ala Cys Lys Gly Arg Ser Pro Glu Gly
            660                 665                 670

Val Arg Arg Val Arg Gln Gln Gly Ala Gly Ala Met Ser Gln Met Ala
        675                 680                 685

Val Ser Ile
    690

<210> SEQ ID NO 10
<211> LENGTH: 728
<212> TYPE: PRT
<213> ORGANISM: Oryza sativa

<400> SEQUENCE: 10

Met Asp Ala Ser Ala Gly Ser Ser Ala Pro His Ser His Gly Asn Pro
1               5                   10                  15

Gly Lys Gln Gly Gly Gly Gly Gly Gly Gly Gly Arg Gly Lys Ala
            20                  25                  30

Pro Ala Ala Glu Ile Arg Gly Glu Ala Ala Arg Asp Asp Val Phe Phe
        35                  40                  45

Ala Asp Asp Thr Phe Pro Leu Leu Pro Asp Phe Pro Cys Leu Ser Ser
    50                  55                  60

Pro Ser Ser Ser Thr Phe Ser Ser Ser Ser Asn Ser Ser Ser
65                  70                  75                  80

Ala Phe Thr Thr Ala Ala Gly Gly Cys Gly Gly Glu Pro Ser Glu
                85                  90                  95

Pro Ala Ser Ala Ala Asp Gly Phe Gly Glu Leu Ala Asp Ile Asp Gln
            100                 105                 110

Leu Leu Asp Leu Ala Ser Leu Ser Val Pro Trp Glu Ala Glu Gln Pro
        115                 120                 125
```

```
Leu Phe Pro Asp Asp Val Gly Met Met Ile Glu Asp Ala Met Ser Gly
    130                 135                 140

Gln Pro His Gln Ala Asp Asp Cys Thr Gly Asp Gly Asp Thr Lys Ala
145                 150                 155                 160

Val Met Glu Ala Ala Gly Gly Asp Asp Ala Gly Asp Ala Cys Met
                165                 170                 175

Glu Gly Ser Asp Ala Pro Asp Asp Leu Pro Ala Phe Phe Met Glu Trp
                180                 185                 190

Leu Thr Ser Asn Arg Glu Tyr Ile Ser Ala Asp Asp Leu Arg Ser Ile
            195                 200                 205

Arg Leu Arg Arg Ser Thr Ile Glu Ala Ala Ala Arg Leu Gly Gly
210                 215                 220

Gly Arg Gln Gly Thr Met Gln Leu Leu Lys Leu Ile Leu Thr Trp Val
225                 230                 235                 240

Gln Asn His His Leu Gln Lys Lys Arg Pro Arg Thr Ala Ile Asp Asp
                245                 250                 255

Gly Ala Ala Ser Ser Asp Pro Gln Leu Pro Ser Pro Gly Ala Asn Pro
            260                 265                 270

Gly Tyr Glu Phe Pro Ser Gly Gly Gln Glu Met Gly Ser Ala Ala Ala
            275                 280                 285

Thr Ser Trp Met Pro Tyr Gln Ala Phe Thr Pro Pro Ala Ala Tyr Gly
            290                 295                 300

Gly Asp Ala Met Tyr Pro Gly Ala Ala Gly Pro Phe Pro Phe Gln Gln
305                 310                 315                 320

Ser Cys Ser Lys Ser Ser Val Val Ser Ser Gln Pro Phe Ser Pro
                325                 330                 335

Pro Thr Ala Ala Ala Gly Asp Met His Ala Ser Gly Gly Gly Asn
                340                 345                 350

Met Ala Trp Pro Gln Gln Phe Ala Pro Phe Pro Val Ser Ser Thr Ser
            355                 360                 365

Ser Tyr Thr Met Pro Ser Val Val Pro Pro Pro Phe Thr Ala Gly Phe
    370                 375                 380

Pro Gly Gln Tyr Ser Gly Gly His Ala Met Cys Ser Pro Arg Leu Ala
385                 390                 395                 400

Gly Val Glu Pro Ser Ser Thr Lys Glu Ala Arg Lys Lys Arg Met Ala
                405                 410                 415

Arg Gln Arg Arg Leu Ser Cys Leu Gln Gln Gln Arg Ser Gln Gln Leu
            420                 425                 430

Asn Leu Ser Gln Ile His Ile Ser Gly His Pro Gln Glu Pro Ser Pro
            435                 440                 445

Arg Ala Ala His Ser Ala Pro Val Thr Pro Ser Ser Ala Gly Cys Arg
    450                 455                 460

Ser Trp Gly Ile Trp Pro Pro Ala Ala Gln Ile Ile Gln Asn Pro Leu
465                 470                 475                 480

Ser Asn Lys Pro Asn Pro Pro Ala Thr Ser Lys Gln Pro Lys Pro
                485                 490                 495

Ser Pro Glu Lys Pro Lys Pro Lys Pro Gln Ala Ala Thr Ala Gly
                500                 505                 510

Ala Glu Ser Leu Gln Arg Ser Thr Ala Ser Glu Lys Arg Gln Ala Lys
            515                 520                 525

Thr Asp Lys Asn Leu Arg Phe Leu Leu Gln Lys Val Leu Lys Gln Ser
    530                 535                 540

Asp Val Gly Ser Leu Gly Arg Ile Val Leu Pro Lys Lys Glu Ala Glu
```

```
545                 550                 555                 560

Val His Leu Pro Glu Leu Lys Thr Arg Asp Gly Val Ser Ile Pro Met
                565                 570                 575

Glu Asp Ile Gly Thr Ser Gln Val Trp Asn Met Arg Tyr Arg Phe Trp
                580                 585                 590

Pro Asn Asn Lys Ser Arg Met Tyr Leu Leu Glu Asn Thr Gly Asp Phe
                595                 600                 605

Val Arg Ser Asn Glu Leu Gln Glu Gly Asp Phe Ile Val Ile Tyr Ser
            610                 615                 620

Asp Ile Lys Ser Gly Lys Tyr Leu Ile Arg Gly Val Lys Val Arg Arg
625                 630                 635                 640

Ala Ala Gln Glu Gln Gly Asn Ser Ser Gly Ala Val Gly Lys His Lys
                645                 650                 655

His Gly Ser Pro Glu Lys Pro Gly Val Ser Ser Asn Thr Lys Ala Ala
                660                 665                 670

Gly Ala Glu Asp Gly Thr Gly Gly Asp Asp Ser Ala Glu Ala Ala Ala
            675                 680                 685

Ala Ala Ala Ala Gly Lys Ala Asp Gly Gly Cys Lys Gly Lys Ser
                690                 695                 700

Pro His Gly Val Arg Arg Ser Arg Gln Glu Ala Ala Ala Ala Ser
705                 710                 715                 720

Met Ser Gln Met Ala Val Ser Ile
                725

<210> SEQ ID NO 11
<211> LENGTH: 720
<212> TYPE: PRT
<213> ORGANISM: Arabidopsis thaliana

<400> SEQUENCE: 11

Met Lys Ser Leu His Val Ala Ala Asn Ala Gly Asp Leu Ala Glu Asp
  1               5                  10                  15

Cys Gly Ile Leu Gly Gly Asp Ala Asp Asp Thr Val Leu Met Asp Gly
                 20                  25                  30

Ile Asp Glu Val Gly Arg Glu Ile Trp Leu Asp Asp His Gly Gly Asp
             35                  40                  45

Asn Asn His Val His Gly His Gln Asp Asp Asp Leu Ile Val His His
         50                  55                  60

Asp Pro Ser Ile Phe Tyr Gly Asp Leu Pro Thr Leu Pro Asp Phe Pro
 65                  70                  75                  80

Cys Met Ser Ser Ser Ser Ser Ser Thr Ser Pro Ala Pro Val Asn
                 85                  90                  95

Ala Ile Val Ser Ser Ala Ser Ser Ser Ala Ala Ser Ser Ser Thr
                100                 105                 110

Ser Ser Ala Ala Ser Trp Ala Ile Leu Arg Ser Asp Gly Glu Asp Pro
            115                 120                 125

Thr Pro Asn Gln Asn Gln Tyr Ala Ser Gly Asn Cys Asp Asp Ser Ser
        130                 135                 140

Gly Ala Leu Gln Ser Thr Ala Ser Met Glu Ile Pro Leu Asp Ser Ser
145                 150                 155                 160

Gln Gly Phe Gly Cys Gly Glu Gly Gly Asp Cys Ile Asp Met Met
                165                 170                 175

Glu Thr Phe Gly Tyr Met Asp Leu Leu Asp Ser Asn Glu Phe Phe Asp
            180                 185                 190
```

```
Thr Ser Ala Ile Phe Ser Gln Asp Asp Thr Gln Asn Pro Asn Leu
        195                 200                 205

Met Asp Gln Thr Leu Glu Arg Gln Glu Asp Gln Val Val Pro Met
210                 215                 220

Met Glu Asn Asn Ser Gly Gly Asp Met Gln Met Met Asn Ser Ser Leu
225                 230                 235                 240

Glu Gln Asp Asp Leu Ala Ala Val Phe Leu Glu Trp Leu Lys Asn
        245                 250                 255

Asn Lys Glu Thr Val Ser Ala Glu Asp Leu Arg Lys Val Lys Ile Lys
            260                 265                 270

Lys Ala Thr Ile Glu Ser Ala Ala Arg Arg Leu Gly Gly Lys Glu
        275                 280                 285

Ala Met Lys Gln Leu Leu Lys Leu Ile Leu Glu Trp Val Gln Thr Asn
        290                 295                 300

His Leu Gln Arg Arg Thr Thr Thr Thr Thr Asn Leu Ser Tyr
305                 310                 315                 320

Gln Gln Ser Phe Gln Gln Asp Pro Phe Gln Asn Pro Asn Pro Asn Asn
                325                 330                 335

Asn Asn Leu Ile Pro Pro Ser Asp Gln Thr Cys Phe Ser Pro Ser Thr
            340                 345                 350

Trp Val Pro Pro Pro Gln Gln Ala Phe Val Ser Asp Pro Gly
        355                 360                 365

Phe Gly Tyr Met Pro Ala Pro Asn Tyr Pro Pro Gln Pro Glu Phe Leu
370                 375                 380

Pro Leu Leu Glu Ser Pro Pro Ser Trp Pro Pro Pro Gln Ser Gly
385                 390                 395                 400

Pro Met Pro His Gln Gln Phe Pro Met Pro Pro Thr Ser Gln Tyr Asn
                405                 410                 415

Gln Phe Gly Asp Pro Thr Gly Phe Asn Gly Tyr Asn Met Asn Pro Tyr
                420                 425                 430

Gln Tyr Pro Tyr Val Pro Ala Gly Gln Met Arg Asp Gln Arg Leu Leu
        435                 440                 445

Arg Leu Cys Ser Ser Ala Thr Lys Glu Ala Arg Lys Lys Arg Met Ala
450                 455                 460

Arg Gln Arg Arg Phe Leu Ser His His His Arg His Asn Asn Asn Asn
465                 470                 475                 480

Asn Asn Asn Asn Asn Asn Gln Gln Asn Gln Thr Gln Ile Gly Glu Thr
                485                 490                 495

Cys Ala Ala Val Ala Pro Gln Leu Asn Pro Val Ala Thr Thr Ala Thr
            500                 505                 510

Gly Gly Thr Trp Met Tyr Trp Pro Asn Val Pro Ala Val Pro Pro Gln
        515                 520                 525

Leu Pro Pro Val Met Glu Thr Gln Leu Pro Thr Met Asp Arg Ala Gly
        530                 535                 540

Ser Ala Ser Ala Met Pro Arg Gln Gln Val Val Pro Asp Arg Arg Gln
545                 550                 555                 560

Gly Trp Lys Pro Glu Lys Asn Leu Arg Phe Leu Leu Gln Lys Val Leu
                565                 570                 575

Lys Gln Ser Asp Val Gly Asn Leu Gly Arg Ile Val Leu Pro Lys Lys
            580                 585                 590

Glu Ala Glu Thr His Leu Pro Glu Leu Glu Ala Arg Asp Gly Ile Ser
        595                 600                 605

Leu Ala Met Glu Asp Ile Gly Thr Ser Arg Val Trp Asn Met Arg Tyr
```

-continued

```
            610                 615                 620
Arg Phe Trp Pro Asn Asn Lys Ser Arg Met Tyr Leu Leu Glu Asn Thr
625                 630                 635                 640

Gly Asp Phe Val Lys Thr Asn Gly Leu Gln Glu Gly Asp Phe Ile Val
                645                 650                 655

Ile Tyr Ser Asp Val Lys Cys Gly Lys Tyr Leu Ile Arg Gly Val Lys
                660                 665                 670

Val Arg Gln Pro Ser Gly Gln Lys Pro Glu Ala Pro Pro Ser Ser Ala
                675                 680                 685

Ala Thr Lys Arg Gln Asn Lys Ser Gln Arg Asn Ile Asn Asn Asn Ser
                690                 695                 700

Pro Ser Ala Asn Val Val Val Ala Ser Pro Thr Ser Gln Thr Val Lys
705                 710                 715                 720

<210> SEQ ID NO 12
<211> LENGTH: 750
<212> TYPE: PRT
<213> ORGANISM: Phaseolus vulgaris

<400> SEQUENCE: 12

Met Glu Cys Glu Val Lys Leu Lys Gly Gly Asp Leu His Ala Glu Gly
 1               5                  10                  15

Val Thr Glu Thr Asn Ala Val Gly Phe Asp Ala Met Glu Asp Glu Gln
                20                  25                  30

Thr Leu Thr Val Ala Glu Arg Glu Met Trp Leu Asn Ser Asp Gln Asp
             35                  40                  45

Glu Phe Leu Gly Val Asn Glu Ala Ser Met Phe Tyr Ala Asn Phe Pro
     50                  55                  60

Pro Leu Pro Asp Phe Pro Cys Thr Ser Ser Ser Ser Ser Ser Ser Ser
 65                  70                  75                  80

Ala Ala Pro Leu Pro Leu Lys Thr Thr Thr Cys Ser Thr Thr Thr Thr
                 85                  90                  95

Ala Thr Thr Ala Thr Ser Ser Ser Ser Ser Ser Ser Trp Ala Val
            100                 105                 110

Leu Lys Ser Asp Val Glu Glu Asp Val Glu Lys Asn His Cys Asn
            115                 120                 125

Gly Ser Met Gln Asp Gln Phe Asp Ala Thr Ala Leu Ser Ser Thr Ala
            130                 135                 140

Ser Met Glu Ile Ser Gln Gln Gln Asn Pro Asp Pro Gly Leu Gly Gly
145                 150                 155                 160

Ser Val Gly Glu Cys Met Glu Asp Val Met Asp Thr Phe Gly Tyr Met
                165                 170                 175

Glu Leu Leu Glu Ala Asn Asp Phe Phe Asp Pro Ala Ser Ile Phe Gln
            180                 185                 190

Asn Glu Glu Ser Glu Asp Pro Leu Ile Glu Phe Gly Val Leu Glu Glu
            195                 200                 205

Gln Val Ser Leu Gln Glu Glu Gln His Glu Met Val His Gln Gln Glu
            210                 215                 220

Asn Thr Glu Glu Asp Arg Lys Val Pro Val Cys Glu Val Ile Lys Gly
225                 230                 235                 240

Glu Glu Glu Gly Gly Gly Gly Gly Gly Arg Val Val Asp Asp Glu
                245                 250                 255

Met Ser Asn Val Phe Leu Glu Trp Ser Lys Ser Asn Lys Asp Ser Val
                260                 265                 270
```

-continued

```
Ser Ala Asn Asp Leu Arg Asn Val Lys Leu Lys Lys Ala Thr Ile Glu
        275                 280                 285

Ser Ala Ala Lys Arg Leu Gly Gly Lys Glu Ala Met Lys Gln Leu
        290                 295                 300

Leu Lys Leu Ile Leu Glu Trp Val Gln Thr Ser His Leu Gln Asn Lys
305                 310                 315                 320

Arg Arg Lys Glu Asn Gly Ser Asn Ala Leu Gln Ala Thr Phe Gln Asp
                325                 330                 335

Pro Ser Ala Gln Thr Lys Glu Asn Ala His Thr Ser Gly Ser Phe Ala
                340                 345                 350

Pro Glu Ser Asn Ser Cys Phe Asn Asn Gln Thr Pro Trp Leu Asn Pro
                355                 360                 365

Gln Thr Phe Gly Thr Asp Gln Ala Pro Val Met Val Pro Ser Gln Pro
        370                 375                 380

Tyr Ser Gln Pro Val Ala Gly Tyr Val Gly Asp Pro Tyr Thr Ser Gly
385                 390                 395                 400

Ser Ala Pro Asn Asn Ile Thr Val Asn His Asn His Asn Asn Asn Pro
                405                 410                 415

Tyr Gln Pro Gly Thr Asp Gln Tyr His Met Leu Glu Ser Ala His Ser
                420                 425                 430

Trp Pro His Ser Gln Phe Asn Val Ala Ser His Tyr Ser Gln Ser Tyr
        435                 440                 445

Gly Glu Asn Gly Leu Phe Thr His Gly Gly Phe Gly Gly Tyr Ala Ile
        450                 455                 460

Thr Arg Tyr Pro Tyr Gln Phe His Gly Pro Gly Asp Arg Leu Met
465                 470                 475                 480

Arg Leu Gly Pro Ser Ala Thr Lys Glu Ala Arg Lys Lys Arg Met Ala
                485                 490                 495

Arg Gln Arg Lys Phe Leu Ser His His Arg Asn Gln Asn Gly Asn His
                500                 505                 510

Leu Gln Asn Gln Gly Ser Asp Pro His Ala Arg Leu Gly Asn Asp Asn
        515                 520                 525

Cys Thr Thr Gly Leu Val Ala Pro His Gln Pro Asn Ser Ala Ala Ala
        530                 535                 540

Asn Trp Met Tyr Trp Gln Ala Met Thr Gly Gly Pro Ala Gly Pro Leu
545                 550                 555                 560

Ala Pro Val Val Pro Ala Asp Pro Leu Ala Gly Gln Thr Val Val Asp
                565                 570                 575

Arg Thr Thr Met His Thr Gln Asn Ser His Gln Asn Arg Ala Ala Ser
                580                 585                 590

Asp Arg Arg Gln Gly Trp Lys Pro Glu Lys Asn Val Arg Phe Leu Gly
        595                 600                 605

Gln Lys Val Leu Lys Gln Ser Asp Val Gly Lys Leu Gly Arg Ile Val
        610                 615                 620

Leu Pro Lys Lys Glu Ala Glu Thr His Leu Pro Glu Leu Glu Ala Arg
625                 630                 635                 640

Asp Gly Ile Ser Ile Thr Met Glu Asp Ile Gly Thr Ser Arg Val Trp
                645                 650                 655

Asn Met Arg Tyr Arg Tyr Trp Pro Asn Asn Lys Ser Arg Met Tyr Met
                660                 665                 670

Leu Glu Asn Thr Gly Asp Phe Val Arg Ala Asn Gly Leu Gln Glu Gly
        675                 680                 685

Asp Phe Ile Val Ile Tyr Ser Asp Val Lys Cys Gly Lys Tyr Met Ile
```

|     | 690 |     |     | 695 |     |     | 700 |     |     |
| --- | --- | --- | --- | --- | --- | --- | --- | --- | --- |
| Arg | Gly | Val | Lys | Val | Arg | Gln | Gln | Gly | Val | Lys | Pro | Glu | Thr | Lys | Pro |
| 705 |     |     |     | 710 |     |     |     | 715 |     |     |     | 720 |

Ala Gly Lys Ser Gln Lys Thr Thr Thr Gly Thr Asn Ala Ser Tyr Thr
            725                 730                 735

Ala Gly Thr Ala Ala Asn Asn Gly Met Ser Ser His Arg Asn
            740                 745                 750

<210> SEQ ID NO 13
<211> LENGTH: 817
<212> TYPE: DNA
<213> ORGANISM: Triticum aestivum

<400> SEQUENCE: 13

```
attctcggga ccccgagcc agaggcgcct cggcgggccc cacgccgcag cgcccggggc      60
aggcggcggc ttccgacaag cagcggcagc agggtgcgag gacccggcgg cggcgccggc    120
ggcaggagac aagaacccgc ggttcctgct gcagaaggtg ctcaagcaga gcgacgtcgg    180
aacctcggcc gcatcgtgct ccccaaaaag gaagcggaga ctcacctgcc ggagctcaag    240
acggggacg gcatctcgat ccccattgag gacatcggca catctcagat tttggcccaa    300
caacaagagc agaatgtatc ttctagagaa cactggtgac tttgttcggt cgaatagctg    360
caggagggtg atttcatcgt gctttactct gatgtcaagt cggcaaatat ctatccggcg    420
tgaaggtgag agcgcaacag gatctagcca agcacaaaat gccagtccag agaaaggcgg    480
ggcttcctga agcgggcgga aagacggcg gctgcaggag aagcccccc acggcgtccg    540
gcgatctcgc caggaggccg cctccatgaa ccagatggcg gtgagcatct gaaatgagca    600
gctcgccgtc cgatccacca ttgaagatca gttagctagc tcaagtatac ccttgatgat    660
gatcaaatcg atctctcgtt tagatccgtg cttcggtatg ctgtagccct agttagggat    720
gatgatacta aagtactatc ggtcagatgt gacctaaaat gcatggtccg tgctgttaac    780
cgtataagct gtaacccttt taaaaaaaaa aaaaaaa                             817
```

<210> SEQ ID NO 14
<211> LENGTH: 1133
<212> TYPE: DNA
<213> ORGANISM: Triticum aestivum

<400> SEQUENCE: 14

```
ggcacgaggc ggcgcctgtc gtgcctgcag cagcagcgga gccagcagct gaatctgagc      60
cagatccaaa ccggcggctt ccctcaagag ccatccccc gcgcggcgca ctcggcgccg    120
gtcactccgc cgtcgtctgg ctggggaggc ctctggacgc aacaagccgt ccagagccag    180
ccccatggcc agctcatggt ccaggtcccg aatccgctgt cgacgaagtc caattcctca    240
aggcagaagc agcaaaaacc ctcgccggac gcagcagcga ggccgccctc cggcggcgcc    300
gccacgccgc agcgcccggg gcaggcggcg gcttccgaca gcagcggca gcagggtgcg    360
aggacgccgc cggcggcgcc ggcggcagga gacaagaacc cgcggttcct gctgcagaag    420
gtgctcaagc agagcgacgt cggaaccctc ggccgcatcg tgctccccaa agaagcggag    480
actcacctgc cggagctcaa gacggggac ggcatctcga tccccattga ggacatcggc    540
acatctcaga ttttggccca acaacaagag cagaatgtat cttctagaga acactggtga    600
ctttgttcgg tcgaatgagc tgcaggaggg tgatttcatc gtgctttact ctgatgtcaa    660
gtcgggcaaa tatctgatac gcggcgtgaa ggtgagagcg caacaggatc tagccaagca    720
```

```
caagaatgcc agtccagaga aaggcggggc gtccgacgtg aaggcgggcg gagaagacgg      780
cggctgcaag gagaagcccc cccactgcgt ccggcgatct cgccaggagg ccgcctccat      840
gaaccagatg gcggtgagca tctgaaatga gcaggctcgc cgtccgatcc acattgaaga      900
ctcagttagc tagctcaagt atcccgttg atgatgatca aatcgatctc tcgttctatg       960
atccgtgctt ccgtgtactg ctgtagcccc agttagggat gatgatacta aagtagctat     1020
cggtcagatg tgacgctgaa gaatgcatgg tccgtgctgt taaacctgta taaaggctgt     1080 aaccccttctg tacatgcatg aacataccct taaaaaaaaa aaaaaaaaaa aaa           1133
```

<210> SEQ ID NO 15
<211> LENGTH: 1185
<212> TYPE: DNA
<213> ORGANISM: Triticum aestivum

<400> SEQUENCE: 15

```
cgcagcggat ggaaccggcg gcgaccaggg aggcccggaa gaagaggatg gcgaggcagc       60
ggcgcctgtc gtgcctgcag cagcagcgga gccagcagct gaatctgagc cagatccaaa      120
gcggcggctt ccctcaagaa ccatcccccc gcgcggcgca ctcggcgccg gtcacgccgc      180
cctcttccgg ctggggaggc ctctggtcgc agcatgccgt ccaggccag ccccatggcc       240 agctcatggt ccaggttccg aatccgctgt cgacgaagtc caattcctcg aggcagaagc      300
agcaaaaacc ctcgccggat gcagcagcga ggccgccctc cggcggcgcc gccacgcagc      360
agcgcccggg gcaggcggcg gcttccgaca gcagcggca gcagggtgcg aggacgccgg      420
cggcggcgcc ggcggcagga gacaagaacc tgcggttcct gctgcagaag gtgctcaagc     480
agagcgacgt cggaaccctc ggccgcatcg tgctccccaa agaagcggag actcacctgc      540
cggagctcaa gacggggggac ggcatctcga tccccattga ggacatcggc acatctcagg    600
tgtggagcat gcgtaccga ttttggccca acaacaagag cagaatgtat ctttctggag       660
aacactggag actttgttcg gtcgaatgag ctgcaggagg gtgatttcat cgtgctttac      720
tctgatgtca agtcgggcaa atatctgata cgcggcgtga aggtaagagc gcaacaggat      780
ctagccaagc acaagaatgg cagtccagag aaaggtgggg cgtccgacgc gaaggcgggc      840
gcagaagacg gtggttgcaa agagaagtct ccgcacggtg tccggcgatc tcgccaggag      900
gccgcctcca tgaaccagat ggccgtgagc atctgaaatg agcaggctcg cgcggtccga      960
tcccccattg aagactactt agctagctca agtatacctg ttgatgatga tcaaatcgat     1020
ctcccgttct atgatccgtg cttccgtgta ctgctgtagc cctagttagg gatggtgata     1080
ctaaagtagc tatcggtcag atgtgacgct gaagaatgca tggtccgtgc tgttaaacct    1140
gtataaaagt gtaaccttct gttaaaaaaa aaaaaaaaaa aaaaa                     1185
```

<210> SEQ ID NO 16
<211> LENGTH: 1916
<212> TYPE: DNA
<213> ORGANISM: Triticum aestivum

<400> SEQUENCE: 16

```
ggcacgagcc accatcgagg ccgcggccgc gcgcctcggt ggggggcgcc agggcaccat       60
gcagctgctc aagctcatcc tcacctgggt gcagaaccac cacctgcaga agaagcgccc      120
ccgcgtcggc gccatggatc aggaggcgcc gccggcagga ggccagctcc cagccccgg      180 cgcaaacccc ggctacgaat tccccgcgga gacgggtgcc gccgctaaca catcttggat     240
gccctaccag gccttctcgc caactggatc ctacggcggc gaggcgatct acccgttcca     300
```

-continued

```
gcagggctgc agcacgagca gcgtggccgt gagcagccag ccgttctccc cgccggcggc    360
gcccgacatg cacgccgggg cctggccgct tcagtacgcg cgttcgtcc cagctggggc    420 cacatccgca ggcactcaaa catacccgat gccgccgccg ggggccgtgc cgcagccgtt   480
cgcggccccc ggattcgccg ggcagttccc gcagcggatg gaaccggcgg cgaccaggga   540
ggcccggaag aagaggatgg cgaggcagcg cgcgcctgtc tgcctgcagc agcagcggag   600
ccagcagctg aatctgagcc agatccaaag cggcggcttc cctcaagaac catcccccg    660 cgcggcgcac tcgcgccgg tcacgccgcc ctcttccggc tggggaggcc tctggtcgca    720
gcatgccgtc cagggccagc ccatggcca gctcatggtc caggttccga atccgctgtc    780
gacgaagtcc aattcctcga ggcagaagca gcaaaaaccc tcgccggatg cagcagcgag   840
gccgccctcc ggccggccgc cacgcagcag cgcccggggc aggcggcggc ttccgacaag   900
cagcggcagc aggtgcatgc atgcacgaac acctcttgcc atccatccat cgatcgccat   960
cccgcataga atcacaagcc attgctcccc aaataagtgt gcgtacatcg taagagacgc  1020
acatcgctgt ccagcgatag gatatccccg catcgccatc ccgcatagaa tcacaagcca  1080
ttgctcccct gcacggtgaa ttgcgtttct caacgaggtt ccgtgcatgc gcgcagggtg  1140
cgaggacgcc ggcggcggcg ccggcggcag gagacaagaa cctgcggttc ctgctgcaga  1200
aggtgctcaa gcagagcgac gtcggaaccc tcggccgcat cgtgctcccc aaaaaggaag  1260
cggagactca cctgccggag ctcaagacgg gggacggcat ctcgatcccc attgaggaca  1320
tcggcacatc tcaggtgtgg agcatgcggt accgattttg gcccaacaac aagagcagaa  1380
tgtatgttgt ggagaacact ggagactttg ttcggtcgaa tgagctgcag gagggtgatt  1440
tcatcgtgct ttactctgat gtcaagtcgg gcaaatatct gatacgcggc gtgaaggtaa  1500
gagcgcaaca ggatctagcc aagcacaaga atggcagtcc agagaaaggt ggggcgtccg  1560
acgcgaaggc gggcgcagaa gacggtggtt gcaaagagaa gtctccgcac ggtgtccggc  1620
gatctcgcca ggaggccgcc tccatgaacc agatggccgt gagcatctga atgagcagg   1680 ctcgcgcggt ccgatccccc attgaagact acttagctag ctcaagtata cctgttgatg  1740
atgatcaaat cgatctcccg ttctatgatc cgtgcttccg tgtactgctg tagccctagt  1800
tagggatggt gatactaaag tagctatcgg tcagatgtga cgctgaagaa tgcatggtcc  1860
gtgctgttaa acctgtataa aggctgtaac ccttctgtaa aaaaaaaaa aaaaaa       1916
```

<210> SEQ ID NO 17
<211> LENGTH: 953
<212> TYPE: DNA
<213> ORGANISM: Triticum aestivum

<400> SEQUENCE: 17

```
gtccagagcc agccccatgg ccagctcatg gtccaggtcc cgaatccgct gtcgacgaag    60
tccaattcct caaggcagaa gcagcaaaaa ccctcgccgg acgcagcagc gaggccgccc   120
tccggcggcg ccgccacgcc gcagcgcccg gggcaggcgc cggcttccga caagcagcgg   180
cagcagggtg cgaggacgcc ggcggcggcg ccggcggcag gagacaagaa cccgcggttc   240
ctgctgcaga aggtgctcaa gcagagcgac gtcggaaccc tcggccgcat cgtgctcccc   300
aaagaagcgg agactcacct gccggagctc aagacggggg acggcatctc gatccccatt   360
gaggacatcg gcacatctca ggtgtggagc atgcgatttt ggcccaacaa caagagcaga   420
atgtatcttc tagagaacac tggtgacttt gttcggtcga atgagctgca ggagggtgat   480
```

-continued

| | |
|---|---:|
| ttcatcgtgc tttactctga tgtcaagtcg ggcaaatatc tgatacgcgg cgtgaaggtg | 540 |
| agagcgcaac aggatctagc caagcacaag aatgccagtc cagagaaagg cggggcgtcc | 600 |
| gacgtgaagg cgggcggaga agacggcggc tgcaaggaga agccccccca cggcgtccgg | 660 |
| cgatctcgcc aggaggccgc ctccatgaac cagatggcgg tgagcatctg aaatgagcag | 720 |
| gctcgccgtc cgatccacca ttgaagactc agttagctag ctcaagtata cccgttgatg | 780 |
| atgatcaaat cgatctctcg ttctatgatc cgtgcttccg tgtactgctg tagccctagt | 840 |
| tagggatgat gatactaaag tagctatcgg tcagatgtga cgctgaagaa tgcatggtcc | 900 |
| gtgctgttaa acctgtaaaa gaaaaaaaaa aaaaagaaa agaaaaaaa aaa | 953 |

<210> SEQ ID NO 18
<211> LENGTH: 1001
<212> TYPE: DNA
<213> ORGANISM: Triticum aestivum

<400> SEQUENCE: 18

| | |
|---|---:|
| tggtcgcagc atgccgtcca gggccagccc catggccagc tcatggtcca ggttccgaat | 60 |
| ccgctgtcga cgaagtccaa ttcctcgagg cagaagcagc aaaaaccctc gccggatgca | 120 |
| gcagcgaggc cgccctccgg cggcgccgcc acgcagcagc gcccggggca ggcggcgget | 180 |
| tccgacaagc agcggcagca gggtgcgagg acgccggcgg cggcgccggc ggcaggagac | 240 |
| aagaacctgc ggttcctgct gcagaaggtg ctcaagcaga gcgacgtcgg aaccctcggc | 300 |
| cgcatcgtgc tcccccaaaaa ggaagcggag actcacctgc cggagctcaa gacgggggac | 360 |
| ggcatctcga tccccattga ggacatcggc acatctcagg tgtggagcat gcggtaccga | 420 |
| ttttggccca acaacaagag cagaatgtat cttctggaga acactggaga ctttgttcgg | 480 |
| tcgaatgagc tgcaggaggg tgatttcatc gtgctttact ctgatgtcaa gtcgggcaaa | 540 |
| tatctgatac gcgcgtgaa ggtaagagcg caacaggatc tagccaagca caagaatggc | 600 |
| agtccagaga aggtggggc gtccgacgcg aaggcgggcg cagaagacgg tggttgcaaa | 660 |
| gagaagtctc cgcacggtgt ccggcgatct cgccaggagg ccgcctccat gaaccagatg | 720 |
| gccgtgagca tctgaaatga gcaggctcgc gcggtccgat ccccattga agactactta | 780 |
| gctagctcaa gtatacctgt tgatgatgat caaatcgatc tcccgttcta tgatccgtgc | 840 |
| ttccgtgtac tgctgtagcc ctagttaggg atggtgatac taaagtagct atcggtcaga | 900 |
| tgtgacgctg aagaatgcat ggtccgtgct gttaaacctg tataaaggct gtaacccttc | 960 |
| tgtaaaaaaa aaaaaaaaaa aaaaaaaaaa aaaaaaaaa a | 1001 |

<210> SEQ ID NO 19
<211> LENGTH: 1173
<212> TYPE: DNA
<213> ORGANISM: Triticum aestivum

<400> SEQUENCE: 19

| | |
|---|---:|
| ggcacgagcc gcagcggatg gagccggcgg cgaccaggga ggcccggaag aagaggatgg | 60 |
| cgaggcagcg gcgcctgtcg tgcctgcagc agcagcggag ccagcagctg aatctgagcc | 120 |
| agatccaaac cggcggcttc cctcaagagc catcccccg cgcggcgcac tcggcgccgg | 180 |
| tcacgccgcc gtcgtctggc tggggaggcc tctggacgca acaagccgtc cagagccagc | 240 |
| cccatggcca gctcatggtc caggtcccga atccgctgtc gacgaagtcc aattcctcaa | 300 |
| ggcagaagca gcaaaaaccc tcgccggacg cagcagcgag gccgccctcc ggcggcgccg | 360 |
| ccacgccgca gcgcccgggg caggcggcgg cttccgacaa gcagcggcag cagggtgcga | 420 |

```
ggacgccggc ggcggcgccg gcggcaggag acaagaaccc gcggttcctg ctgcagaagg    480
tgctcaagca gagcgacgtc ggaaccctcg ccgcatcgt gctccccaaa aaggaagcgg     540
agactcacct gccggagctc aagacggggg acggcatctc gatccccatt gaggacatcg    600
gcacatctca gattttggcc caacaacaag agcagaatgt atcttctaga gaacactggt    660
gactttgttc ggtcgaatga gctgcaggag ggtgatttca tcgtgctttta ctctgatgtc    720 aagtcgggca aatatctgat acgcggcgtg aaggtgagag cgcaacagga tctagccaag    780
cacaagaatg ccagtccaga gaaaggcggg gcgtccgacg tgaaggcggg cggagaagac    840
ggcggctgca aggagaagcc cccccacggc gtccggcgat ctcgccagga ggccgcctcc    900
atgaaccaga tggcggtgag catctgaaat gagcaggctc gccgtccgat ccaccattga    960
agactcagtt agctagctca agtatacccg ttgatgatga tcaaatcgat ctctcgttct   1020
atgatccgtg cttccgtgta ctgctgtagc cctagttagg gatgatgata ctaaagtagc   1080
tatcggtcag atgtgacgct gaagaatgca tggtccgtgc tgttaaacct gtataaaggc   1140 tgtaacccctt ctgtaaaaaa aaaaaaaaaa aaa                                1173

<210> SEQ ID NO 20
<211> LENGTH: 1134
<212> TYPE: DNA
<213> ORGANISM: Triticum aestivum

<400> SEQUENCE: 20
ggcacgaggc ggcgcctgtc gtgcctgcag cagcagcgga gccagcagct gaatctgagc    60
cagatccaaa ccgcggcctt ccctcaagag ccatcccccc gcgcggcgca ctcggcgccg   120
gtcactccgc cgtcgtctgg ctggggaggc ctctggacgc aacaagccgt ccagagccag   180
ccccatggcc agctcatggt ccaggtcccg aatccgctgt cgacgaagtc caattcctca    240
aggcagaagc agcaaaaacc ctcgccggac gcagcagcga ggccgccctc cggcggcgcc    300
gccacgccgc agcgcccggg gcaggcgcg gcttccgaca gcagcggca gcagggtgcg     360 aggacgccgg cggcggcgcc ggcggcagga acaagaaccc gcggttcct gctgcagaag    420 gtgctcaagc agagcgacgt cggaaccctc ggccgcatcg tgctccccaa agaagcggag    480
actcacctgc cggagctcaa gacgggggac ggcatctcga tccccattga ggacatcggc   540
acatctcaga ttttggccca acaacaagag cagaatgtat cttctagaga acactggtga    600
ctttgttcgg tcgaatgagc tgcaggaggg tgatttcatc gtgctttact ctgatgtcaa    660
gtcgggcaaa tatctgatac gcggcgtgaa ggtgagagcg caacaggatc tagccaagca    720
caagaatgcc agtccagaga aaggcgggc gtccgacgtg aaggcgggcg agaagacgg    780 cggctgcaag gagaagcccc ccacggcgt ccggcgatct cgccaggagg ccgcctccat    840
gaaccagatg gcggtgagca tctgaaatga gcaggctcgc cgtccgatcc accattgaag   900
actcagttag ctagctcaag tatacccgtt gatgatgatc aaatcgatct ctcgttctat    960
gatccgtgct tccgtgtact gctgtagccc tagttaggga tgatgatact aaagtagcta   1020
tcggtcagat gtgacgctga agaatgcatg gtccgtgctg ttaaacctgt ataaaggctg   1080
taacccttct gtacatgcat gaacataccc ttaaaaaaaa aaaaaaaaaa aaaa          1134

<210> SEQ ID NO 21
<211> LENGTH: 1186
<212> TYPE: DNA
<213> ORGANISM: Triticum aestivum
```

```
<400> SEQUENCE: 21
cgcagcggat ggaaccggcg gcgaccaggg aggcccggaa gaagaggatg gcgaggcagc      60
ggcgcctgtc gtgcctgcag cagcagcgga gccagcagct gaatctgagc cagatccaaa     120
gcggcggctt ccctcaagaa ccatcccccc gcgcggcgca ctcggcgccg gtcacgccgc     180
cctcttccgg ctggggaggc ctctggtcgc agcatgccgt ccagggccag ccccatggcc     240
agctcatggt ccaggttccg aatccgctgt cgacgaagtc caattcctcg aggcagaagc     300
agcaaaaacc ctcgccggat gcagcagcga ggccgccctc cggcggcgcc gccacgcagc     360
agcgcccggg gcaggcggcg gcttccgaca gcagcggca gcagggtgcg aggacgccgg      420
cggcggcgcc ggcggcagga gacaagaacc tgcggttcct gctgcagaag gtgctcaagc     480
agagcgacgt cggaaccctc ggccgcatcg tgctccccaa gaagcggag actcacctgc      540
cggagctcaa gacgggggac ggcatctcga tccccattga ggacatcggc acatctcagg     600
tgtggagcat gcggtaccga ttttggccca acaacaagag cagaatgtat cttctggaga     660
acactggaga ctttgttcgg tcgaatgagc tgcaggaggg tgatttcatc gtgctttact     720
ctgatgtcaa gtcgggcaaa tatctgatac gcggcgtgaa ggtaagagcg caacaggatc     780
tagccaagca caagaatggc agtccagaga aggtggggc gtccgacgcg aaggcgggcg      840
cagaagacgg tggttgcaaa gagaagtctc cgcacgtgt ccggcgatct cgccaggagg      900
ccgcctccat gaaccagatg gccgtgagca tctgaaatga gcaggctcgc gcggtccgat     960
cccccattga agactactta gctagctcaa gtatacctgt tgatgatgat caaatcgatc    1020
tcccgttcta tgatccgtgc ttccgtgtac tgctgtagcc ctagttaggg atggtgatac    1080
taaagtagct atcggtcaga tgtgacgctg aagaatgcat ggtccgtgct gttaaacctg    1140
tataaaggct gtaacccttc tgttaaaaaa aaaaaaaaaa aaaaaa                   1186

<210> SEQ ID NO 22
<211> LENGTH: 1916
<212> TYPE: DNA
<213> ORGANISM: Triticum aestivum

<400> SEQUENCE: 22
ggcacgagcc accatcgagg ccgcggccgc gcgcctcggt gggggcgcc agggcaccat       60
gcagctgctc aagctcatcc tcacctgggt gcagaaccac cacctgcaga gaagcgccc     120
ccgcgtcggc gccatggatc aggaggcgcc gccggcagga ggccagctcc ccagccccgg    180
cgcaaacccc ggctacgaat tccccgcgga gacgggtgcc gccgctaaca catcttggat    240
gccctaccag gccttctcgc caactggatc ctacggcggc gaggcgatct acccgttcca    300
gcagggctgc agcacgagca gcgtggccgt gagcagccag ccgttctccc gccggcggc    360
gcccgacatg cacgccgggg cctggccgct tcagtacgcg gcgttcgtcc agctggggc    420
cacatccgca ggcactcaaa catacccgat gccgccgccg ggggccgtgc gcagccgtt    480
cgcggccccc ggattcgccg gcagttccc gcagcggatg gaaccggcgg cgaccaggga   540
ggcccggaag aagaggatgg cgaggcagcg gcgcctgtcg tgcctgcagc agcagcggag    600
ccagcagctg aatctgagcc agatccaaag cggcggcttc cctcaagaac catcccccg    660
cgcggcgcac tcggcgccgg tcacgccgcc ctcttccggc tggggaggcc tctggtcgca    720
gcatgccgtc cagggccagc ccatggcca gctcatggtc caggttccga atccgctgtc     780
gacgaagtcc aattcctcga ggcagaagca gcaaaaaccc tcgccggatg cagcagcgag    840
gccgccctcc ggcggcgccg ccacgcagca gcgcccgggg caggcggcgg cttccgacaa    900
```

-continued

```
gcagcggcag caggtgcatg catgcacgaa cacctcttgc catccatcca tcgatcgcca    960
tcccgcatag aatcacaagc cattgctccc caaataagtg tgcgtacatc gtaagagacg   1020
cacatcgctg tccagcgata ggatatcccc gcatcgccat cccgcataga atcacaagcc   1080
attgctcccc tgcacggtga attgcgtttc tcaacgaggt tccgtgcatg cgcgcagggt   1140
gcgaggacgc cggcggcggc gccggcggca ggagacaaga acctgcggtt cctgctgcag   1200
aaggtgctca agcagagcga cgtcggaacc ctcggccgca tcgtgctccc caaaaaggaa   1260
gcggagactc acctgccgga gctcaagacg ggggacggca tctcgatccc cattgaggac   1320
atcggcacat ctcaggtgtg gagcatgcgg taccgatttt ggcccaacaa caagagcaga   1380
atgtatcttc tggagaacac tggagacttt gttcggtcga atgagctgca ggagggtgat   1440
ttcatcgtgc tttactctga tgtcaagtcg ggcaaatatc tgatacgcgg cgtgaaggta   1500
agagcgcaac aggatctagc caagcacaag aatggcagtc cagagaaagg tggggcgtcc   1560
gacgcgaagg cgggcgcaga agacggtggt tgcaaagaga agtctccgca cggtgtccgg   1620
cgatctcgcc aggaggccgc ctccatgaac cagatggccg tgagcatctg aaatgagcag   1680
gctcgcgcgg tccgatcccc cattgaagac tacttagcta gctcaagtat acctgttgat   1740
gatgatcaaa tcgatctccc gttctatgat ccgtgcttcc gtgtactgct gtagccctag   1800
ttagggatgg tgatactaaa gtagctatcg gtcagatgtg acgctgaaga atgcatggtc   1860
cgtgctgtta aacctgtata aaggctgtaa cccttctgta aaaaaaaaaa aaaaaa       1916
```

<210> SEQ ID NO 23
<211> LENGTH: 414
<212> TYPE: DNA
<213> ORGANISM: Triticum aestivum

<400> SEQUENCE: 23

```
ggtgcgagga cgccggcggc ggcgccggcg gcaggagaca agaacccgcg gttcctgctg     60
cagaaggtgc tcaagcagag cgacgtcgga accctcggcc gcatcgtgct ccccaaaaag    120
gaagcggaga ctcacctgcc ggagctcaag acggggacg gcatctcgat ccccattgag    180
gacatcggca catctcagat tttggcccaa caacaagagc agaatgtatc ttctagagaa    240
cactggtgac tttgttcggt cgaatgagct gcaggagggt gatttcatcg tgctttactc    300
tgatgtcaag tcgggcaaat atctgatacg cggcgtgaag gtgagagcgc aacaggatct    360
agccaagcac aagaatgcca gtccagagaa aggcggggcg tccgacgtga aggc          414
```

<210> SEQ ID NO 24
<211> LENGTH: 411
<212> TYPE: DNA
<213> ORGANISM: Triticum aestivum

<400> SEQUENCE: 24

```
ggtgcgagga cgccggcggc ggcgccggcg gcaggagaca agaacccgcg gttcctgctg     60
cagaaggtgc tcaagcagag cgacgtcgga accctcggcc gcatcgtgct ccccaaagaa    120
gcggagactc acctgccgga gctcaagacg ggggacggca tctcgatccc cattgaggac    180
atcggcacat ctcagatttt ggcccaacaa caagagcaga atgtatcttc tagagaacac    240
tggtgacttt gttcggtcga atgagctgca ggagggtgat ttcatcgtgc tttactctga    300
tgtcaagtcg ggcaaatatc tgatacgcgg cgtgaaggtg agagcgcaac aggatctagc    360
caagcacaag aatgccagtc cagagaaagg cggggcgtcc gacgtgaagg c              411
```

<210> SEQ ID NO 25
<211> LENGTH: 434
<212> TYPE: DNA
<213> ORGANISM: Triticum aestivum

<400> SEQUENCE: 25

| | | | | | |
|---|---|---|---|---|---|
| ggtgcgagga | cgccggcggc | ggcgccggcg | gcaggagaca | agaacctgcg | gttcctgctg | 60 |
| cagaaggtgc | tcaagcagag | cgacgtcgga | accctcggcc | gcatcgtgct | ccccaaaaag | 120 |
| gaagcggaga | ctcacctgcc | ggagctcaag | acggggacg | gcatctcgat | ccccattgag | 180 |
| gacatcggca | catctcaggt | gtggagcatg | cggtaccgat | tttggcccaa | caacaagagc | 240 |
| agaatgtatc | ttctggagaa | cactggagac | tttgttcggt | cgaatgagct | gcaggagggt | 300 |
| gatttcatcg | tgctttactc | tgatgtcaag | tcgggcaaat | atctgatacg | cggcgtgaag | 360 |
| gtaagagcgc | aacaggatct | agccaagcac | aagaatggca | gtccagagaa | aggtggggcg | 420 |
| tccgacgcga | aggc | | | | | 434 |

<210> SEQ ID NO 26
<211> LENGTH: 431
<212> TYPE: DNA
<213> ORGANISM: Triticum aestivum

<400> SEQUENCE: 26

| | | | | | |
|---|---|---|---|---|---|
| ggtgcgagga | cgccggcggc | ggcgccggcg | gcaggagaca | agaacctgcg | gttcctgctg | 60 |
| cagaaggtgc | tcaagcagag | cgacgtcgga | accctcggcc | gcatcgtgct | ccccaaagaa | 120 |
| gcggagactc | acctgccgga | gctcaagacg | gggacggca | tctcgatccc | cattgaggac | 180 |
| atcggcacat | ctcaggtgtg | gagcatgcgg | taccgattt | ggcccaacaa | caagagcaga | 240 |
| atgtatcttc | tggagaacac | tggagactttt | gttcggtcga | atgagctgca | ggagggtgat | 300 |
| ttcatcgtgc | tttactctga | tgtcaagtcg | ggcaaatatc | tgatacgcgg | cgtgaaggta | 360 |
| agagcgcaac | aggatctagc | caagcacaag | aatggcagtc | cagagaaagg | tggggcgtcc | 420 |
| gacgcgaagg | c | | | | | 431 |

<210> SEQ ID NO 27
<211> LENGTH: 500
<212> TYPE: DNA
<213> ORGANISM: Triticum aestivum

<400> SEQUENCE: 27

| | | | | | |
|---|---|---|---|---|---|
| tcacaagcca | ttgctcccct | gcacggtgaa | ttgcgtttct | caacgaggtt | ccgtgcatgc | 60 |
| gcgcagggtg | cgaggacgcc | ggcggcggcg | ccggcggcag | gagacaagaa | cctgcggttc | 120 |
| ctgctgcaga | aggtgctcaa | gcagagcgac | gtcggaaccc | tcggccgcat | cgtgctcccc | 180 |
| aaaaaggaag | cggagactca | cctgccggag | ctcaagacgg | gggacggcat | ctcgatcccc | 240 |
| attgaggaca | tcggcacatc | tcaggtgtgg | agcatgcggt | accgattttg | cccaacaac | 300 |
| aagagcagaa | tgtatcttct | ggagaacact | ggagactttg | ttcggtcgaa | tgagctgcag | 360 |
| gagggtgatt | tcatcgtgct | ttactctgat | gtcaagtcgg | gcaaatatct | gatacgcggc | 420 |
| gtgaaggtaa | gagcgcaaca | ggatctagcc | aagcacaaga | atggcagtcc | agagaaaggt | 480 |
| ggggcgtccg | acgcgaaggc | | | | | 500 |

<210> SEQ ID NO 28
<211> LENGTH: 11
<212> TYPE: PRT
<213> ORGANISM: Triticum aestivum

<400> SEQUENCE: 28

Thr Ser Gln Val Trp Ser Met Arg Tyr Arg Phe
 1               5                  10

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 29
caactcatgg tcccgaatcc                                              20

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 30
gcttgttaga cgaattgac                                               19

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 31
aatatctgat acgcggcgtg aaggtg                                       26

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 32
aggatctagc caagcacaag aatgg                                        25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 33
gcccatatga actcgatcga ttgac                                        25

<210> SEQ ID NO 34
<211> LENGTH: 26
<212> TYPE: DNA
<213> ORGANISM: Artificial Sequence -continued

```
<220> FEATURE:
<223> OTHER INFORMATION: Description of Artificial Sequence: Primer

<400> SEQUENCE: 34
gttgtccata tgaactcgat cgattc                                              26
```